(12) United States Patent
Luo et al.

(10) Patent No.: US 11,345,956 B2
(45) Date of Patent: May 31, 2022

(54) METHODS AND COMPOSITIONS RELATED TO PROSTATE CANCER THERAPEUTICS

(71) Applicant: The Johns Hopkins University, Baltimore, MD (US)

(72) Inventors: Jun Luo, Clarksville, MD (US); Emmanuel S. Antonarakis, Silver Spring, MD (US); Changxue Lu, Ellicott City, MD (US); William Isaacs, Reisterstown, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 185 days.

(21) Appl. No.: 15/505,882

(22) PCT Filed: Aug. 25, 2015

(86) PCT No.: PCT/US2015/046806
§ 371 (c)(1),
(2) Date: Feb. 22, 2017

(87) PCT Pub. No.: WO2016/033114
PCT Pub. Date: Mar. 3, 2016

(65) Prior Publication Data
US 2017/0275673 A1    Sep. 28, 2017

Related U.S. Application Data

(60) Provisional application No. 62/149,408, filed on Apr. 17, 2015, provisional application No. 62/120,877, filed on Feb. 26, 2015, provisional application No. 62/041,368, filed on Aug. 25, 2014.

(51) Int. Cl.
| | | |
|---|---|---|
| *C12Q 1/68* | (2018.01) | |
| *C12Q 1/686* | (2018.01) | |
| *A61K 39/00* | (2006.01) | |
| *A61K 31/00* | (2006.01) | |
| *A61K 45/06* | (2006.01) | |
| *C12Q 1/6853* | (2018.01) | |

(52) U.S. Cl.
CPC ............ *C12Q 1/686* (2013.01); *A61K 31/00* (2013.01); *A61K 39/001102* (2018.08); *A61K 45/06* (2013.01); *C12Q 1/6853* (2013.01); *A61K 39/00* (2013.01); *A61K 2039/6056* (2013.01); *A61K 2300/00* (2013.01); *C12Q 2521/107* (2013.01); *C12Q 2539/103* (2013.01); *C12Q 2545/114* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,877,611 A | 10/1989 | Cantrell |
| 5,223,409 A | 6/1993 | Ladner et al. |
| 5,225,539 A | 7/1993 | Winter |
| 5,399,346 A | 3/1995 | Anderson et al. |
| 5,530,101 A | 6/1996 | Queen et al. |
| 5,556,752 A | 9/1996 | Lockhart et al. |
| 5,565,332 A | 10/1996 | Hoogenboom et al. |
| 5,578,832 A | 11/1996 | Trulson et al. |
| 5,585,089 A | 12/1996 | Queen et al. |
| 5,593,839 A | 1/1997 | Hubbell et al. |
| 5,599,695 A | 2/1997 | Pease et al. |
| 5,631,734 A | 5/1997 | Stern et al. |
| 5,693,762 A | 12/1997 | Queen et al. |
| 5,721,367 A | 2/1998 | Kay et al. |
| 5,837,243 A | 11/1998 | Deo et al. |
| 5,837,832 A | 11/1998 | Chee et al. |
| 5,843,708 A | 12/1998 | Hardman et al. |
| 5,859,205 A | 1/1999 | Adair et al. |
| 5,939,598 A | 8/1999 | Kucherlapati et al. |
| 6,113,898 A | 9/2000 | Anderson et al. |
| 6,130,364 A | 10/2000 | Jakobovits et al. |
| 6,180,377 B1 | 1/2001 | Morgan et al. |
| 6,423,511 B1 | 7/2002 | Nakamura et al. |
| 6,436,665 B1 | 8/2002 | Kuimelis |

(Continued)

FOREIGN PATENT DOCUMENTS

| | | |
|---|---|---|
| CA | 2721506 A1 | 10/2009 |
| EP | 0721016 A2 | 7/1996 |

(Continued)

OTHER PUBLICATIONS

Antonarakis et al. (J Clin Oncol., 2014, 32, p. 5001-5001, abstract) (Year: 2014).*

(Continued)

*Primary Examiner* — Stephanie K Mummert
(74) *Attorney, Agent, or Firm* — Ballard Spahr LLP

(57) ABSTRACT

Disclosed herein are compositions and methods for detecting biological molecules and biomarkers associated with prostate cancer. Disclosed herein are compositions and methods for detecting biological molecules and biomarkers associated with castration-resistant prostate cancer wherein such biological molecules and biomarkers comprise androgen-receptor splice variants that can be used to develop effective therapeutic regimens for prostate cancer patients. Disclosed herein are methods of using biological molecules and biomarkers related to androgen-receptor splice variants for assessing therapeutic resistance to drugs such as enzalutamide and abiraterone.

18 Claims, 36 Drawing Sheets

Specification includes a Sequence Listing.

(56) References Cited

U.S. PATENT DOCUMENTS

| | | | |
|---|---|---|---|
| 6,458,592 B1 | 10/2002 | Jakobovits et al. | |
| 9,146,238 B2 | 9/2015 | Luo et al. | |
| 9,671,405 B2* | 6/2017 | Giannakakou | A61K 31/337 |
| 2002/0165381 A1 | 11/2002 | Ahrens-Fath et al. | |
| 2007/0248535 A1 | 10/2007 | Buttyan et al. | |
| 2015/0233927 A1 | 8/2015 | Giannakakou et al. | |
| 2015/0344965 A1 | 12/2015 | Luo et al. | |

FOREIGN PATENT DOCUMENTS

| | | | |
|---|---|---|---|
| EP | 0728520 A1 | 8/1996 | |
| EP | 0785280 A2 | 7/1997 | |
| EP | 0799897 A1 | 10/1997 | |
| EP | 2300041 A2 | 3/2011 | |
| WO | WO-8601533 | 3/1986 | |
| WO | WO-95/22058 A1 | 8/1995 | |
| WO | WO-97/02357 A1 | 1/1997 | |
| WO | WO-97/27317 | 7/1997 | |
| WO | WO-97/29212 A1 | 8/1997 | |
| WO | WO-02/17904 | 3/2002 | |
| WO | WO-2009/128936 A2 | 10/2009 | |
| WO | WO-2011112581 A1 * | 9/2011 | C12Q 1/6876 |
| WO | WO-2012006241 | 1/2012 | |
| WO | WO-2014/018926 A1 | 1/2014 | |
| WO | WO-2014/047285 A1 | 3/2014 | |
| WO | WO-2014/066864 A2 | 5/2014 | |
| WO | WO-2015/023710 A1 | 2/2015 | |
| WO | WO-2015023710 A1 * | 2/2015 | A61K 31/58 |
| WO | WO-2015/179404 A1 | 11/2015 | |
| WO | WO-2015179404 A1 * | 11/2015 | C12Q 1/6886 |
| WO | WO-2016/033114 A1 | 3/2016 | |

OTHER PUBLICATIONS

Antonarakis et al. (Proceedings of AACR meeting, Abstract 2910, Apr. 5-9, 2014) (Year: 2014).*

Mostaghel et al. (Clin Cancer Res, 17(18):15913-25, 2011) (Year: 2011).*

Miyamoto et al. (Cancer Discovery, 2012, 2(11):995-1003) (Year: 2012).*

Hu et al. (Cancer Research, 2012, 72(14):3457-62) (Year: 2012).*

Hornberg et al. (PloS One, 2011, 6(4):e19059, p. 1-9) (Year: 2011).*

Abrahamsson, P.A., Neuroendocrine Cells in Tumor Growth of the Prostate, Endocrine-Related Cancer, 6:503-19 (1999).

Agoulnik, I.U. and N.L. Weigel, Androgen Receptor Action in Hormone-Dependent and Recurrent Prostate Cancer, J Cell BioChem, 99:362-72 (2006).

Anderson, W.F., Prospects for Human Gene Therapy, Science, 226(4673):401-9 (1984).

Armstrong, A.J. and M.A. Carducci, New Drugs in Prostate Cancer, Curr Opin Urol, 16:138-45 (2006).

Balic et al., Androgen Receptor Length Polymorphism Associated with Prostate Cancer Risk in Hispanic Men, J Urol, 168(5): 2245-8 (2002).

Barltrop, J.A. et al., 5-(3-Carboxymethoxyphenyl)-2-(4,5-Dimethylthiszolyl)-3-(4-Sulfophenyl)Tetrazolium, Inner salt (MTS) and Related Analogs of 3-(4,5-Dimethylthiazolyl)-2,5-Diphenyltetrazolium Bromide (MTT) Reducing to Purple Water-Soluble Formazans as Cell-Viability Indicators, Bioorg & Med Chem Lett, 1(11): 611-4 (1991).

Bendig, M.M., Humanization of Rodent Monoclonal Antibodies by CDR Grafting, Methods: A Companion Methods in Enzymology, 8:83-93 (1995).

Blömer, U. et al., Highly Efficient and Sustained Gene Transfer in Adult Neurons with a Lentivirus Vector, J Virology, 71(9): 6641-9 (1997).

Brigham, K.L. et al., In Vivo Transfection of Murine Lungs with a Functioning Prokaryotic Gene Using a Liposome Vehicle, Am J Med Sci, 298(4): 278-81 (1989).

Brinkmann, A.O. et al., Mechanisms of Androgen Receptor Activation and Function, J Steriod Biochem Mol Biol, 69(1-06): 307-13 (1999).

Brown et al., Deletion of the Steroid-Binding Domain of the Human Androgen Receptor Gene in One Family with Complete Androgen Insensitivity Syndrome: Evidence for Further Genetic Heterogeneity in this Syndrome, Proc Natl Acad Sci USA, 85(21): 8151-5 (1988).

Butler, L.M. et al., Suppression of Androgen Receptor Signaling in Prostate Cancer Cells by an Inhibitory Receptor Variant, Mol Endocrinol, 20(5): 1009-24 (2006).

Carell, T. et al., A Novel Procedure for the Synthesis of Libraries containing Small Organic Molecules, Angew Chem Int Ed Engl, 33(20): 2059-61 (1994).

Carell, T. et al., A Solution-Phase Screening Procedure for the Isolation of Active Compounds from a Library of Molecules, Angew Chem Int Ed Engl, 33(20): 2061-4 (1994).

Casset, F. et al., A Peptide Mimetic of an Anti-CD4 Monoclonal Antibody by Rational Design, Biochem Biophys Res Commun, 307(1): 198-205 (2003).

Catalano, M.G. et al., Altered Expression of Androgen-Receptor Isoforms in Human Colon-Cancer Tissues, Intl J Cancer, 86(3): 325-30 (2000).

Cayouette, M. and C. Gravel, Adenovirus-Mediated Gene Transfer of Ciliary Neurotrophic Factor Can Prevent Photoreceptor Degeneration in the Retinal Degeneration (rd) Mouse, Human Gene Therapy, 8:423-30 (1997).

Ceraline, J et al., Constitutive activation of the androgen receptor by a point mutation in the hinge region: A new mechanism for androgen-independent growth in prostate cancer, Int J Cancer, 108(1):152-7 (2004).

Chen, C.D. et al., Molecular Determinants of Resisteance to Antiandrogen Therapy, Nature Med, 10(1): 33-9 (2004).

Chen, Y. et al., Targeting the Androgen Receptor Pathway in Prostate Cancer, Curr Opin Pharm, 8: 440-8 (2008).

Chmelar, R. et al., Androgen Receptor Coregulators and Their Involvement in the Development and Progression of Prostate Cancer, Int J Cancer, 120: 719-33 (2006).

Cho, C.Y. et al., An Unnatural Biopolymer, Science, 261(5126): 13303-5 (1993).

Cordon-Cardo, C., Androgen Receptor Level in the Prostatectomy Specimen Predicts Time to Disease Progression Post Androgen Suppression Therapy, J Clin Oncol, 25(18S): 5065 (2007).

Cornetta, K. et al., Gene Transfer into Primates and Prospects for Gene Therapy in Humans, Prog Nucleic Acid Res Mol Biol, 36: 311-22 (1989).

Cory, A.H. et al., Use of an Aqueous Soluble Tetrazolium/Formazan Assay for Cell Growth Assays in Culture, Cancer Commun, 3(7): 207-12 (1991).

Cree, A.I. et al., Methotrexate Chemosensitivity by ATP Luminescence in Human Leukemia Cell Lines and in Breast Cancer Primary Cultures: Comparison of the TCA-100 Assay with a Clonogenic Assay, Anticancer Drugs, 6(3): 398-404 (1995).

Crouch, S.P.M., et al., The Use of ATP Bioluminescence as a Measure of Cell Proliferation and Cytotoxicity, J Immunol Meth, 160: 81-8 (1993).

Cull, M.G. et al., Screening for Receptor Ligands Using Large Libraries of Peptides Linked to the C Terminus of the lac Repressor, Proc Natl Acad Sci USA, 89: 1865-9 (1992).

Cwirla, S.E., et al., Peptides on Phage: A Vast Library of Peptides for Identifying Ligands, Proc Natl Acad Sci USA, 87: 6378-82 (1990).

Dehm, S.M. and D.J. Tindall, Androgen Receptor Structural and Functional Elements: Role and Regulation in Prostate Cancer, Mol Endocrinol, 21(12): 2855-63 (2007).

Dehm, S.M. et al., Splicing of a Novel Androgen Receptor Exon Generates a Constitutively Active Androgen Receptor that Mediates Prostate Cancer Therapy Resistance, Cancer Res, 68(13): 5469-77 (2008).

Devlin, J.J. et al., Random Peptide Libraries: A Source of Specific Protein Binding Molecules, Science, 249(4967): 404-6 (1990).

(56) References Cited

OTHER PUBLICATIONS

DeWitt, S.H. et al., Diversomers: An Approach to Nonpeptide, nonoligometric Chemical Diversity, Proc Natl Acad Sci USA, 90: 6909-13 (1993).
Dhanasekaran, S.M. et al., Delineation of Prognostic Biomarkers in Prostate Cancer, Nature, 412: 822-6 (2001).
Erb, E. et al., Recursive Deconvolution of Combinatorial Chemical Libraries, Proc Natl Acad Sci USA, 91: 11422-6 (1994).
Felgner, P.L. et al., Lipofection: A Highly Efficient, Lipid-Mediated DNA-Transfection Procedure, Proc Natl Acad Sci USA, 84: 7413-7 (1987).
Felici, F. et al., Selection of Antibody Ligands from a Large Library of Oligopeptides Expressed on a Multivalent Exposition Vector, J Mol Biol, 222: 301-10 (1991).
Fleming, M.T. et al., Post-Therapy Changes in PSA as an Outcome Measure in Prostate Cancer Clinical Trials, Nat Clin Pract Oncol, 3(12): 658-67 (2006).
Fodor, S.P.A. et al., Multiplexed Biochemical Assays with Bilogical Chips, Nature, 364: 555-6 (1993).
Friedmann, T., Progress Toward Human Gene Therapy, Science, 244(4910) 1275-81 (1989).
Gallop, M.A. et al., Applications of Combinatorial Technologies to Drug Discovery. 1. Background and Peptide Combinatorial Libraries, J Med Chem, 37(9): 1233-51 (1994).
Ge, H. UPA, a Universal Protein Array System for Quantitative Detection of Protein-Protein, Protein-DNA, Protein-RNA and Prtein-Ligand Interactions, Neucleic Acids Reseach, 28(2): e3i-vii (2000).
Gelmann, E.P., Molecular Biology of the Androgen Receptor, J Clin Oncol, 20(13): 3001-15 (2002).
Gu, Y. et al., Hematopoietic Cell Regulation by Rac1 and Rac2 Guanosine Triphosphatases, Science, 302: 445-9 (2003).
Haapala, K. et al., Androgen receptor alterations in prostate cancer relapsed during a combined androgen blockade byorchiectomy and bicalutamide, Lab Invest, 81(12):1647-51 (2001).
Hara Takahito et al., Novel mutations of androgen receptor: a possible mechanism of bicalutamide withdrawal syndrome, Cancer Res, vol. 63(1):149-53 (2003).
Heinlein, C.A. and Chawnshang Chang, Androgen Receptor in Prostate Cancer, Endocr Rev, 25(2): 276-308 (2004).
Heller, R.A. et al., Discovery and Analysis of Inflammatory Disease-Related Genes Using cDNA Microarrays, Proc Natl Acad Sci USA, 94:2150-5 (1997).
Hirata, S. et al., Isoform/Variant mRNAs for Sex Steroid Hormone Receptors in Humans, Trends Endocrin Met, 14(3): 124-9 (2003).
Houghten, R.A. et al., The Use of Synthetic Peptide Combinatorial Libraries for the Identification of Bioactive Peptides, Biotechniques, 13(3): 412-21 (1992).
Hu, R. et al., Ligand-Independent Androgen Receptor Variants Derived from Spicing of Cryptic Exons Signify Hormone-Refractory Protstate Cancer, Cancer Res, 69(1): 16-22 (2009).
Huggins, M.D., C. and C.V. Hodges, M.D., Studies on Prostatic Cancer: I. The Effect of Castration, of Estrogen and of Androgen Injection on Serum Phosphates in Metastatic Carcinoma of the Prostate, Cancer Res, 1: 293-7 (1941).
Jagla, M. et al., A Splicing Variant of the Androgen Receptor Detected in a Metastatic Prostate Cancer Exhibits Exclusively Cytoplasmic Actions, Endocrin, 148(9): 4334-4343 (2007).
Jenster, G. et al., Domains of the Human Androgen Receptor Involved in Steroid Binding Transriptional Activation and Subcellular Localization, Mol Endocrin, 5(10): 1396-1404 (1991).
Johnson, L.G., Gene Therapy for Cystic Fibrosis, Chest, 107: 77S-83S (1995).
Kaarbo, Mari et al., Androgen Signaling and Its Interactions with Other Signaling Pathways in Prostate Cancer, BioEssays, 29: 1227-38 (2007).
Kangas, L. et al., Bioluminescence of Cellular ATP: A New Method for Evaluating Cytotoxic Agents in Vitro, Med Biol, 62(6): 338-43 (1984).
Kido, M. et al., Use of a Retroviral Vector with an Internal Opsin Promoter to Direct Gene Expression to Retinal Photorecptor Cells, Curr Eye Res, 15(8): 833-44 (1996).
Kittler, R. et al., An Endoribonuclease-Prepared siRNA Screen in Human Cells Identifies Genes Essential for Cell Division, Nature, 432: 1036-40 (2004).
Ko et al., Androgen Receptor Down-Regulation in Prostate Cancer with Phosphorodiamidate Morpholino Antisense Oligomers, J Urol, 172(3): 1140-4 (2004).
Lam, K.S., Application of Combinatorial Library Methods in Cancer Research and Drug Discovery, Anticancer Drug Des, 12(3): 145-67 (1997).
Lam, K.S., et al., A New Type of Synthetic Peptide Library for Identifying Ligand-Binding Activity, Nature, 354:82-4 (1991).
Lapouge, Gaelle et al., Specific properties of a C-terminal truncated androgen receptor detected in hormone refractory prostate cancer, Adv Exp Med Biol, 617:529-53 (2017).
Le Gal La Salle, G. et al., An Adenovirus Vector for Gene Transfer into Neurons and Glia in the Brain, Science, 259(5097: 988-90 (1993).
Libertini, S.J. et al., Evidence for Calpain-Mediated Androgen Receptor Cleavage as a Mechanism for Androgen Independence, Cancer Res, 67(19): 9001-5 (2007).
Linja, M.J. and Tapio Visakorpi, Alterations of Androgen Receptor in Prostate Cancer, J Steriod Biochem, 92: 255-64 (2004).
Liu, W. et al., Copy number analysis indicates monoclonal origin of lethal metastatic prostate cancer. Nature Medicine. 15: 559-65 (2009).
Lockhart, D.J. et al., Expression Monitoring by Hybridization to High-Density Oligonucleotide Arrays, Nat Biotechnol, 14: 1675-80 (1996).
Luo, J. et al., Human Prostate Cancer and Benign Prostatic Hyperplasia: Molecular Dissection by Gene Expression Profiling, Cancer Res, 61: 4683-8 (2001).
MacBeath, G. and S.L. Schreiber, Printing Proteins as Microarrays for High-Throughput Function Determination, Science, 289: 1760-3 (2000).
MacCallum, R.M. et al., Antibody-Antigen Interactions: Contact Analysis and Binding Site Topography, J Mol Biol, 262(5): 732-45 (1996).
Maroni, M.D., P.D. and E.D. Crawford, M.D., The Benefits of Early Androgen Blockade, Best Pract Res Cl En, 22(2): 317-29 (2008).
Miller, A.D. and G.J. Rosman, Improved Retroviral Vectors for Gene Transfer and Expression, Biotechniques, 7(9): 980-990 (1989).
Miller, A.D., Retrovirus Packaging Cells, Human Gene Therapy, 1:5-14 (1990).
Miyamoto, A. et al., Increased Proliferation of B Cells and Auto-Immunity in Mice Lacking Protein Kinase Cd, Nature, 416: 865-9 (2002).
Miyoshi, H. et al., Stable and Efficient Gene Transfer into the Retina Using an HIV-Based Lentiviral Vector, Proc Natl Acad Sci USA, 94: 10319-23 (1997).
Moen, R.C., Directions in Gene Therapy, Blood Cells, 17(2): 407-16 (1991).
Montgomery, R.B. et al., Maintenance of Intratumoral Androgens in Metastatic Prostate Cancer: A Mechanism for Castration-Resistant Tumor Growth, Cancer Res, 68(11): 4447-54 (2008).
Mostaghel, E.A. and P.S. Nelson, Intracrine Androgen Metabolism in Prostate Cancer Progression: Mechanisms of Castration Resistance and Therapeutic Implications, Best Pract Res Cl En, 22(2): 243-58 (2008).
Naldini, L. et al., In Vivo Gene Delivery and Stable Transduction of Nondividing Cells by a Lentiviral Vector, Science, 272(5259): 263-7 (1996).
Ono, T. et al., Plasmid DNAs Directly Injected into Mouse Brain with Lipofectin can be Incorporated and Expressed by Brain Cells, Neurosci Lett, 117:259-63 (1990).
Otto, D. and K. Unsicker, Basic FGF Reverses Chemical and Morphological Deficits in the Nigrostriatal System of MPTP-Treated Mice, J Neurosci, 10(6): 1912-21 (1990).

(56) References Cited

OTHER PUBLICATIONS

Otto, D. et al., Basic Fibroblast Growth Factor and Nerve Growth Factor Administered in Gel Foam Rescue Medial Septal Neurons after Fimbria Fornix Transection, J Neurosci Res, 22(1): 83-91 (1989).
Pan, Q. et al., Quantitative Microarray Profiling Provides Evidence Against Widespread Coupling of Alternative Splicing with Nonsense-Mediated mRNA Decay to Control Gene Expression, Genes & Dev, 20:153-8 (2006).
Paul, W.E., Fundamental Immunology, 3rd Edition, New York: Raven Press, pp. 292-295 (1993).
Paull, K.D. et al., The Synthesis of XTT: A New Tetrazolium Reagent that is Bioreducible to a Water-Soluble Formazan, J Heterocyclic Chem, 25: 911-4 (1988).
Petty, R.D., Comparison of MTT and ATP-Based Assays for the Measurement of Viable Cell Number, J Biolumin Chemilumin, 10:29-34 (1995).
Quigley, C.A. et al., Complete Androgen Insensitiveity due to Deletion of Exon C of the Androgen Receptor Gene Highlights the Functional Importance of the Second Zinc Finger of the Androgen Receptor in Vivo, Mol Endocrinol, 6(7): 1103-12 (1992).
Rosenberg, S.A. et al., Gene Transfer into Humans—Immunotherapy of Patients with Advanced Melanoma, Using Tumor-Infiltrating Lymphocytes Modified by Retroviral Gene Transduction, New Engl J Med, 323(9): 570-8 (1990).
Ruefli-Brasse, A.A. et al., Regulation of NF-κB-Dependent Lymphocyte Activation and Development by Paracaspase, Science, 302: 1581-4 (2003).
Saramäki, O.R. et al., Genetic Aberrations in Prostate Cancer by Microarray Analysis, Int J Cancer, 119: 1322-9 (2006).
Schena, M. et al., Parallel Human Genome Analysis: Microarray-Based Expression Monitoring of 1000 Genes, Proc Natl Acad Sci USA, 93: 10614-9 (1996).
Scher, H. I., et al. Antitumour activity of MDV3100 in castration-resistant prostate cancer: a phase 1-2 study (2010) Lancet 375, 1437-1446.
Scher, H.I. and C.L. Sawyers, Biology of Progressive, Castration-Resistant Prostate Cancer: Directed Therapies Targeting the Androgen-Receptor Signaling Axis, J Clin Oncol, 23(32): 8253-61 (2005).
Scott, J.K. and G.P. Smith, Searching for Peptide Ligands with an Epitope Library, Science, 249(4967): 386-90 (1990).
Shang, Y. et al., Formation of the Androgen Receptor Transcription Complex, Mol Cell, 9: 601-10 (2002).
Sharp, D., Conference: Gene Therapy, The Lancet, 337: 1277-8 (1991).
Skolnick, J. and J.S. Fetrow, From Genes to Protein Structure and Function: Novel Applications of Computational Approaches in the Genomic Era, Trends Biotechnol, 18(1): 34-9 (2000).
Small, E.J. and C.J. Ryan, The Case for Secondary Hormonal Therapies in the Chemotherapy Age, J Urol, 176: S66-71 (2006).
Straubinger, R.M. and D. Papahadjopoulos, Liposomes as Carriers for Intracellular Delivery of Nucleic Acids, Method Enzymol, 101: 512-27 (1983).
Suzuki, H. et al., Interfocal Heterogeneity of PTEN/MMAC1 Gene Alterations in Multiple Metastatic Prostate Cancer Tissues, Cancer Res, 58: 204-9 (1998).
Tepper, C.G. et al., Characterization of a Novel Androgen Receptor Mutation in a Relapsed CWR22 Prostate Cancer Xenograft and Cell Line, Cancer Res, 62: 6606-14 (2002).
Tolstoshev, P. and W.F. Anderson, Gene Expression Using Retroviral Vectors, Curr Opin Biotech, 1: 55-61 (1990).
Tyagi, S. and F.R. Kramer, Molecular Beacons: Probes that Fluoresce Upon Hybridization, Nat Biotechnol, 14: 303-8 (1996).
Vajdos, F.F. et al., Comprehensive Functional Maps of the Antigen-Binding Site of an Anti-ErbB2 Antibody Obtained with Shotgun Scanning Mutagenesis, J Mol Biol, 320(2): 415-28 (2002).
Tilley, W.D. et al., Mutations in the Androgen Receptor Gene Are Associated with Progression of Human Prostate Cancer to Androgen Independence, Clin Cancer Res, 2:277-285 (1996).

Wahl, R.L. et al., Improved Radioimaging and Tumor Localization with Monoclonal F(ab')2, J Nucl Med, 24: 316-25 (1983).
Wolff, J.A. et al., Direct Gene Transfer into Mouse Muscle in Vivo, Science, 247(4949 pt. 1): 1465-8 (1990).
Wu, C.H. et al., Targeting Genes: Delivery and Persistent Expression of a Foreign Gene Driven by Mammalian Regulatory Elements in Vivo, J Biol Chem, 264(29): 16985-7 (1989).
Wu, G.Y. and C.H. Wu, Receptor-Mediated Gene Delivery and Expression in Vivo, J Biol Chem, 263(29): 14621-4 (1988).
Wu, H. et al., Humanization of a murine monoclonal antibody by simultaneous optimization of framework and CDR residues, J Mol Biol, 294(1): 151-62 (1999).
Zhou, Z. et al., A Ligand-Dependent Bipartite Nuclear Targeting Signal in the Human Androgen Receptor, J Biol Chem, 269(18): 13115-23 (1994).
Zhu, H. et al., Analysis of Yeast Protein Kinases Using Protein Chips, Nat Genet, 26: 283-9 (2000).
Zhu, X. et al., Identification of an Exon 3 Deletion Splice Variant Androgen Receptor mRNA in Human Breast Cancer, Intl J Cancer, 72(4): 574-80 (1997).
Zuckermann, R.N. et al., Discovery of Nanomolar Ligands for 7-Transmembrane G-Protein-Coupled Receptors from a Diverse N-(Substituted)glycine Peptoid Library, J Med Chem, 37: 2678-85 (1994).
Supplementary European Search Report and Written Opinion completed on Jul. 26, 2011 by the European Patent Office for European Patent Application No. 09733012.0, which was filed on Apr. 16, 2009 and published as 2300041 on Mar. 30, 2011 (Inventor—Luo et al.; Applicant—The Johns Hopkins University;) (10 pages).
Certificate of Patent issued on Jan. 27, 2016 by the European Patent Office for European Patent Application No. 0933012.0, which was filed on Nov. 15, 2010 and granted as 2300041 on Mar. 30, 2011 (Inventor—Luo et al.; Applicant—The Johns Hopkins University;) (1 page).
European Search Report and Written Opinion completed on Jun. 6, 2016 by the European Patent Office for European Patent Application No. 16152616.5, which was filed on Apr. 16, 2009 and published as 3062106 on Aug. 31, 2016, 2011 (Inventor—Luo et al.; Applicant—The Johns Hopkins University;) (9 pages).
International Search Report and Written Opinion dated Dec. 4, 2009 by the International Searching Authority for International Patent Application No. PCT/US2009/002392, which was filed on Apr. 6, 2009 and published as WO 2009/128936 on Oct. 22, 2009 (Inventor—Luo et al.; Applicant—The Johns Hopkins University;) (11 pages).
International Preliminary Report on Patentability dated Oct. 19, 2010 by the International Searching Authority for International Patent Application No. PCT/US2009/002392, which was filed on Apr. 6, 2009 and published as WO 2009/128936 on Oct. 22, 2009 (Inventor—Luo et al.; Applicant—The Johns Hopkins University;) (8 pages).
Preliminary Amendment filed on Oct. 15, 2010 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (11 pages).
Restriction Requirement dated Feb. 29, 2012 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (8 pages).
Response to Restriction Requirement filed on Mar. 29, 2012 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (4 pages).
Non-Final Office Action dated Jun. 20, 2012 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (5 pages).
Response to Non-Final Office Action filed on Sep. 20, 2012 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (12 pages).

(56) References Cited

OTHER PUBLICATIONS

Final Office Action dated Sep. 12, 2013 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (5 pages).
Response to Final Office Action filed on Dec. 12, 2013 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (9 pages).
Advisory Action dated Dec. 19, 2013 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (3 pages).
Non-Final Office Action dated Jun. 5, 2014 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (9 pages).
Response to Non-Final Office Action filed on Aug. 7, 2014 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (10 pages).
Final Office Action dated Nov. 21, 2014 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (21 pages).
Response After Final Office Action filed on Mar. 3, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (8 pages).
Advisory Action dated Apr. 9, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (5 pages).
Response to Advisory Action filed on Apr. 19, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (6 pages).
Advisory Action dated Apr. 28, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (3 pages).
Response to Advisory Action filed on May 14, 2015 with the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (6 pages).
Notice of Allowance dated Jun. 26, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (7 pages).
Issue Notification dated Sep. 29, 2015 by the US Patent and Trademark Office for U.S. Appl. No. 12/988,299, filed Jan. 18, 2011 and published as US 2011/0110926 on May 12, 2011 (Inventor—Luo et al.; Applicant—The Johns Hopkins University;) (1 pages).
Preliminary Amendment filed on May 21, 2015 with the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University;) (3 pages).
Restriction Requirement dated Dec. 30, 2016 by the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University;) (11 pages).
Response to Restriction Requirement filed on Mar. 30, 2017 with the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University;) (13 pages).
Anders et al., HTSeq—A Python framework to work with high-throughput sequencing data. (2014) Bioinformatics.
Andersen et al., Regression of castrate-recurrent prostate cancer by a small-molecule inhibitor of the amino-terminus domain of the androgen receptor. Cancer cell 2010;17:535-46.
Antonarakis Es, et al: AR-V7 and resistance to enzalutamide and abiraterone in prostate cancer. N Engl J Med 371: 1028-1038, 2014.
Armstrong Al, et al. Biomarkers in the management and treatment of men with metastatic castration-resistant prostate cancer. Eur Urol 61: 549-59,2012.
Arora Vk, et al. Glucocorticoid receptor confers resistance to antiandrogens by bypassing androgen receptor blockade. Cell 2013;155:1309-22.
Aryee et al. DNA methylation alterations exhibit intraindividual stability and interindividual heterogeneity in prostate cancer metastases. Science translational medicine 2013;5:169ra10.
Attard et al. Phase I clinical trial of a selective inhibitor of CYP17, abiraterone acetate, confirms that castration-esistant prostate cancer commonly remains hormone driven. Journal of clinical oncology : official journal of the American Society of Clinical Oncology 2008;26:4563-71.
Balbas et al. Overcoming mutation-based resistance to antiandrogens with rational drug design. eLife 2013;2.
Basch E, et al: Systemic therapy in men with metastatic castration-resistant prostate cancer: American Society of Clinical Oncology and Cancer .Care Ontario clinical practice guideline. J Clin Oncol 32: 3436-3448, 2014.
Carver et al. Reciprocal feedback regulation of PI3K and androgen receptor signaling in PTEN-deficient prostate cancer. Cancer Cell 2011;19:575-86.
Chang, K. H., et al. A Gain-of-Function Mutation in DHT Synthesis in Castration-Resistant Prostate Cancer. (2013) Cell 154, 1074-1084.
Chee et al., Accessing Genetic Information with High-Density DNA Arrays. Science 274:610 (1996).
Darshan et al: Taxane-induced blockade to nuclear accumulation of the androgen receptor predicts clinical responses in metastatic prostate cancer. Cancer Res 71: 6019-6029, 2011.
De Bono Js, et al: Abiraterone and increased survival in metastatic prostate cancer. N Engl J Med 364: 1995-2005, 2011.
De Bono Js, et al: Prednisone plus cabazitaxel or mitoxantrone for metastatic castration-resistant prostate cancer progressing after docetaxel treatment: a randomised open-label trial: Lancet 376: 1147-1154, 2010.
De Leeuw et al. Novel actions of next-generation taxanes benefit advanced stages of prostate cancer. Clin. Cancer Res. 2015; 21:795-807.
Dehm Sm, et al: Splicing of a novel androgen receptor exon generates a constitutively active androgen receptor that mediates prostate cancer therapy resistance. Cancer Res 68: 5469-5477, 2008.
Efstathiou E, et al. MDV3100 effects on androgen receptor (AR) signaling and bone marrow testosterone concentration modulation: A preliminary report. ASCO Meeting Abstracts 2011;29:4501.
Efstathiou E, et al. Effects of abiraterone acetate on androgen signaling in castrate-resistant prostate cancer in bone. Journal of clinical oncology : official journal of the American Society of Clinical Oncology 2012;30:637-43.
Eisenhauer Ea, et al: New response evaluation criteria in solid tumours: revised RECIST guideline (version 1.1). Eur J Cancer 45: 228-247, 2009.
Gan L, et al: Inhibition of the androgen receptor as a novel mechanism of taxol chemotherapy in prostate cancer. Cancer Res 69: 8386-8394, 2009.
Guo Z, et al. A Novel Androgen Receptor Splice Variant Is Up-regulated during Prostate Cancer Progression and Promotes Androgen Depletion—Resistant Growth. Cancer Research 2009;69:2305-13.

(56) References Cited

OTHER PUBLICATIONS

Hacia et al., Detection of heterozygous mutations in BRCA1 using high density oligonucleotide arrays and two-colour fluorescence analysis. Nature Genetics 14:441, 1996.
Hornberg E, et al. Expression of Androgen Receptor Splice Variants in Prostate Cancer Bone Metastases is Associated with Castration-Resistance and Short Survival. PLoS ONE 2011;6:e19059.
Hu et al. Ligand—independent androgen receptor variants derived from splicing of cryptic exons signify hormone—refractory prostate cancer. Cancer Res 2009;69:16-22.
Hu R, et al. A snapshot of the expression signature of androgen receptor splicing variants and their distinctive transcriptional activities. The Prostate 2011;71:1656-67.
Hu R, et al. Distinct transcriptional programs mediated by the ligand—dependent full—length androgen receptor and its splice variants in castration—resistant prostate cancer. Cancer Res 2012;72:3457-62.
Itakura et al., Synthesis and Use of Synthetic Oligonucleotides. Ann. Rev. Biochem. 53:323-356 (1984).
Joseph Jd, et al. A clinically relevant androgen receptor mutation confers resistance to 2nd generation anti-androgens enzalutamide and ARN-509. Cancer Discovery 2013.
Kantoff et al. Sipuleucel-T immunotherapy for castration-resistant prostate cancer. N Engl J Med 363: 411-422, 2010.
Karantanos T, et al: Understanding the mechanisms of androgen deprivation resistance in prostate cancer at the molecular level. Eur Urol, epub ahead of print (doi: 10.1016/j.eururo.2014.09.049), 2014.
Kirby BJ, et al. Functional characterization of circulating tumor cells with a prostate-cancer-specific microfluidic device. PLoS One 7: e35976, 2012.
Kozal et al., Extensive polymorphisms observed in HIV-1 clade B protease gene using high-density oligonucleotide arrays. Nature Medicine 2:753, 1996.
Li Y, et al. Androgen receptor splice variants mediate enzalutamide resistance in castration-resistant prostate cancer cell lines. Cancer Res 73: 483-489, 2013.
Liu W, et al.Copy number analysis indicates monoclonal origin of lethal metastatic prostate cancer. Nature medicine 2009;15:559-65.
Lockhart et al., Expression monitoring by hybridization to high-density oligonucleotide arrays. Nature Biotechnology 14:1675 (1996).
Longo DL. New therapies for castration-resistant prostate cancer. The New England journal of medicine 2010;363:479-81.
Luo J, et al. Human prostate cancer and benign prostatic hyperplasia: molecular dissection by gene expression profiling. Cancer Res 2001;61:4683-8.
Mitsiades N, et al. Distinct patterns of dysregulated expression of enzymes involved in androgen synthesis and metabolism in metastatic prostate cancer tumors. Cancer Res 2012;72:6142-52.
Mostaghel EA, Marck BT, Plymate SR, et al. Resistance to CYP17A1 inhibition with abiraterone in castration-resistant prostate cancer: induction of steroidogenesis and androgen receptor splice variants. Clinical cancer research : an official journal of the American Association for Cancer Research 2011;17:5913-25.
Nadiminty N, et al. NF-kappaB2/p52 induces resistance to enzalutamide in prostate cancer: role of androgen receptor and its variants. Molecular cancer therapeutics 2013;12:1629-37.
Narang et al., Chemical Synthesis of Deoxyoligonucleotides by the Modified Triester Method. Methods Enzymol., 65:610-620 (1980).
Norris JD, et al. The homeodomain protein HOXB13 regulates the cellular response to androgens. Molecularcell 2009;36:405-16.
O'Donnell A, et al. Hormonal impact of the 17alphahydroxylase/C(17,20)-lyase inhibitor abiraterone acetate (CB7630) in patients with prostate cancer. British journal of cancer 2004;90:2317-25.
Parker C, et al: Alpha emitter radium-223 and survival m metastatic prostate cancer. N Engl J Med 369:213-223, 2013.
Plymate Sr, et al.Taxane resistance in prostate cancer mediated by ARdependent GATA2 regustion ofIGF2. Cancer Cell, 2015; 27:158-159.

Ravindranathan P, et al. Peptidomimetic targeting of critical androgen receptor—coregulator interactions in prostate cancer. Nat Commun 2013;4:1923.
Roberts et al., RNA-peptide fusions for the in vitro selection of peptides and proteins. Proc. Natl. Acad. Sci. USA, 94(23)12997-302 (1997).
Robinson et al. Integrative genomics viewer. Nature biotechnology 2011; 29:24-6.
Ryan, C. J., et al. Abiraterone in Metastatic Prostate Cancer without Previous Chemotherapy (2013) New England Journal of Medicine 368, 138-148.
Ryan, C. J. et al., Androgen Receptor Rediscovered: The New Biology and Targeting the Androgen Receptor Therapeutically (2011) Journal of Clinical Oncology : Official Journal of the American Society of Clinical Oncology 29, 3651-3658.
Sadar D. Small Molecule Inhibitors Targeting the "Achilles' Heel" of Androgen Receptor Activity. (2011) Cancer Res 71, 1208-1213.
Sahu, B., et al. FoxA1 Specifies Unique Androgen and Glucocorticoid Receptor Binding Events in Prostate Cancer Cells (2013) Cancer Res 73, 1570-1580.
Scher Hi, et al: Increased survival with enzalutamide in prostate cancer after chemotherapy. N Engl J Med 367: 1187-1197, 2012.
Scher Hi, et al: Design and end points of clinical trials for patients with progressive prostate cancer and castrate levels of testosterone: recommendations of the Prostate Cancer Clinical Trials Working Group. J Clin Oncol 26: 1148-1159, 2008.
Seruga B, et al. Drug resistance in metastatic castration-resistant prostate cancer. Nat Rev Clin Oncol 8: 12-23, 2011.
Steplewski et al., Effects of Restraint Stress on Inoculated Tumor Growth and Immune Response in Rats. (1985) Cancer Research 45: 5128-5133.
Subramanan A., et al. Gene set enrichment analysis: A knowledge-based approach for interpreting genome-wide expression profiles. (2005) Proceedings of the National Academy of Sciences of the United States of America 102: 15545-15550.
Tannock If, et al: Docetaxel plus prednisone or mitoxantrone plus prednisone for advanced prostate cancer. N Engl J Med 3 51: 1502-1512, 2004.
Thadani-Mulero, et al., Androgen receptor on the move: boarding the microtubule expressway to the nucleus. Cancer Res 72: 4611-4615, 2012.
Thadani-Mulero, et al: Androgen receptor splice variants determine taxane sensitivity in prostate cancer. Cancer Res 74: 2270-82, 2014.
Therasse P., et al. New Guidelines to Evaluate the Response to Treatment in Solid Tumors. (2000) Journal of the National Cancer Institute 92, 205-216).
Tran C, et al. Development of a Second-Generation Antiandrogen forTreatment of Advanced Prostate Cancer. Science 2009;324:787-90.
Van Soest Rj, et al. Targeting the androgen receptor confers in vivo cross-resistance between enzalutamide and docetaxel, but not cabazitaxel, in castration-resistant prostate cancer. Eur. Urol. 2014; epub ahead of print (10.1016/j.euro.2014.11.033).
Verhoeyen et al., Engineering of Antibodies. (1988) BioEssays. 8, 2:74-78.
Watson P.A., et al. Constitutively active androgen receptor splice variants expressed in castration-resistant prostate cancer require full-length androgen receptor. (2010) Proceedings of the National Academy of Sciences 107 (39):16759-16765.
Yu Y., et al.Expression and Function of the Progesterone Receptor in Human Prostate Stroma Provide Novel Insights to Cell Proliferation Control (2013) The Journal of clinical endocrinology and metabolism 98, 2887-2896.
Yu et al. Rapid Induction of Androgen Receptor Splice Variants by Androgen Deprivation in Prostate Cancer. Clin Cancer Res. 2014, vol. 20, No. 6, ; pp. 1590-1600.
Zhang, X., et al. Androgen Receptor Variants Occur Frequently in Castration Resistant Prostate Cancer Metastases. (2011) PLoS ONE 6, e27970.
Zhu et al: Tubulin-targeting chemotherapy 1 mpairs androgen receptor activity in prostate cancer. Cancer Res 70: 7992-8002, 2010.

(56) References Cited

OTHER PUBLICATIONS

International Search Report and Written Opinion dated Jan. 12, 2016 by the International Searching Authority for International Application No. PCT/US2015/046806, which was filed on Aug. 25, 2015 and published as WO/2016/033114 on Mar. 3, 2016 (Applicant—The John Hopkins University) (13 pages).

International Preliminary Report on Patentability dated Feb. 28, 2017 by the International Searching Authority for International Application No. PCT/US2015/046806, which was filed on Aug. 25, 2015 and published as WO/2016/033114 on Mar. 3, 2016 (Applicant—The John Hopkins University) (9 pages).

De Bono, J.S. et al., Circulating tumor cells predict survival benefit from treatment in metastatic castration-resistant prostate cancer. Clin. Cancer Res. (2008); 14:6302-6309.

Magbanua, M.J.M. et al., Isolation and genomic analysis of circulating tumor cells from castration resistant metastatic prostate cancer, BMC Cancer. (2012); 12: 78.

Mortazavi, A. et al., Mapping and quantifying mammalian transcriptomes by RNA-Seq. Nature Methods, 2008. 5(7): p. 621-628.

Robinson, J.T. et al., Integrative genomics viewer. Nat. Biotechnol. (2011):29:24-26.

Trapnell, C. et al., Differential gene and transcript expression analysis of RNA-seq experiments with TopHat and Cufflinks. Nat Protoc. (2012); 7:562-578.

Trapnell, C. et al., TopHat: discovering splice junctions with RNA-Seq. Bioinformatics (2009); 25: 1105-1111.

Trapnell, C. et al., "Transcript assembly and quantification by RNA-Seq reveals unannotated transcripts and isoform switching during cell differentiation". Nat Biotechnol (2010) 28(5): 511-515. (Cufflinks).

Wang, Z. et al., RNA-Seq: a revolutionary tool for transcriptomics, Nat Rev Genet. (2009);10(1):57-63.

Yu et al., Circulating tumor cells: approaches to isolation and characterization. J Cell Biol. (2011);192(3): 373-382.

Communication Pursuant to Rules 161(2) and 162 EPC dated Mar. 31, 2017 by the European Patent Office for Patent Application No. 15835018.1, which was filed on Aug. 25, 2015 and published as 3186396 on Jul. 5, 2017 (Inventor—Luo et al.; Applicant—Johns Hopkins University;) (2 pages).

Office Action dated Apr. 30, 2015 by the Canadian Intellectual Property Office for Patent Application No. 2721506, which was filed on Apr. 16, 2009 (Inventor—Luo et al.; Applicant—The Johns Hopkins University;) (9 pages).

Office Action dated May 24, 2017 by the Canadian Intellectual Property Office for Patent Application No. 2721506, which was filed on Apr. 16, 2009 (Inventor—Luo et al.; Applicant—The Johns Hopkins University;) (7 pages).

Communication Pursuant to Article 94(3) EPC dated Aug. 18, 2017 by the European Patent Office for European Patent Application No. 16152616.5, which was filed on Apr. 16, 2009 and published as 3062106 on Aug. 31, 2016, 2011 (Inventor—Luo et al.; Applicant—The Johns Hopkins University;) (4 pages).

Non Final Rejection filed on Jun. 30, 2017 with the United States Patent and Trademark Office for U.S. Appl. No. 14/718,955, filed May 21, 2015 and published as US 2015/0344965 on Dec. 3, 2015 (Inventor—Luo et al.; Applicant—The Johns Hopkins University;) (15 pages).

International Search Report and Written Opinion dated Sep. 24, 2015 by the International Searching Authority for International Application No. PCT/US2015/031584, which was filed on May 19, 2015 and published as WO 2015/179404 on Nov. 26, 2015 (Applicant—The John Hopkins University) (17 pages).

International Preliminary Report on Patentability dated Nov. 22, 2016 by the International Searching Authority for International Application No. PCT/US2015/031584, which was filed on May 19, 2015 and published as WO 2015/179404 on Nov. 26, 2015 (Applicant—The John Hopkins University) (13 pages).

Antonarakis, et al., "Androgen Receptor Splice Variant 7 and Efficacy of Taxane Chemotherapy in Patients With Metastatic Castration-Resistant Prostate Cancer",JAMA Oncol. 1(5):582-591, (2015).

Nakazawa et al., "Androgen Receptor Splice Variants in the Era of Enzalutamide and Abiraterone", Horm. Cancer. 5(5):265-273, (2014).

Extended European Search Report dated Dec. 8, 2017, by the European Patent Office for EP Application No. 15835018.1, which was filed on Aug. 25, 2015 and published as EP 3186393 A1 on Jul. 5, 2017 (Applicant—The Johns Hopkins University) (8 pages).

Final Rejection dated Feb. 23, 2018 by the USPTO for U.S. Appl. No. 14/718,955, filed May 21, 2015, and published as US 2015-0344965 A1 on Dec. 3, 2015 (Inventor—Jun Luo; Applicant—The Johns Hopkins University) (16 pages).

Response to Final Rejection dated Apr. 13, 2018 to the USPTO for U.S. Appl. No. 14/718,955, filed May 21, 2015, and published as US 2015-0344965 A1 on Dec. 3, 2015 (Inventor—Jun Luo; Applicant—The Johns Hopkins University) (18 pages).

Jenster G et al: "Functional domains of the human androgen receptor", Journal of Steroid Biochemistry and Molecular Biology, Elsevier Science Ltd. vol. 41, No. 3-8,(1992), pp. 671-675.

Communication pursuant to Article 94(3) EPC dated Apr. 19, 2018 by the European Patent Office for EP Application No. 16152616.5, which was filed on Apr. 16, 2009 and published as EP 3062106 on Aug. 31, 2016 (Applicant—The John Hopkins University) (8 pages).

Mary Nakazawa et al: "Androgen Receptor Splice Variants in the Era of Enzalutamide and Abiraterone", Hormones and Cancer, vol. 5, No. 5, (2014), pp. 265-273.

Emmanuel S Antonarakis et al: "Androgen receptor splice variant-7 predicts resistance to enzalutamide in patients with castration-resistant prostate cancer I Cancer Research", Cancer Research, (2014) (Abstract).

EP Communication pursuant to Article 94(3) EPC dated Mar. 28, 2019 by the European Patent Office for EP Application No. 15835018.1, which was filed on Aug. 25, 2015 (Applicant—The John Hopkins University) (7 Pages).

Jiang et al. "Detection of androgen receptor mutations in circulating tumor cells in castration-resistant prostate cancer" Clin. Chem., 56(9):1492-1495 (2010).

Non Final Rejection dated Oct. 19, 2018 by the USPTO for U.S. Appl. No. 15/309,986, filed Nov. 9, 2016 and published as US 2017/0268063 A1 on Sep. 21, 2017 (Inventor—Jun Luo, et al.)(10 pages).

Notice of Reasons for Refusal dated Jun. 3, 2019 by the Japanese Patent Office for JP Application No. 2017-511236, which was filed on Aug. 25, 2015 and published as 2017-534248 on Nov. 24, 2017 (Applicant—Unknown)(Original—4 pages// Translation—3 pages).

Androgen receptor splice variant-7 predicts resistance to enzalutamide in patients with castration-resistant prostate cancer, Proceedings: AACR Annual Meeting 2014,Apr. 5-9, 2014, (Abstract No. 2910).

Final Rejection dated Jun. 27, 2019 by the USPTO for U.S. Appl. No. 14/718,955, filed May 21, 2015 and published as US 2015-0344965 A1 on Dec. 3, 2015 (Inventor—Jun Luo) (10 pages).

Commmunication pursuant to Article 94(3) EPC dated Aug. 6, 2019 by the European Patent Office for EP Application No. 16152616.5, which was filed on Apr. 16, 2009 and published as EP 3062106 on Aug. 31, 2016 (Applicant—The John Hopkins University) (4 pages).

Response to Final Rejection dated Aug. 7, 2019 to the USPTO for U.S. Appl. No. 14/718,955, filed May 21, 2015 and published as US 2015/0344965 A1 on Dec. 3, 2015 (Inventor—Jun Luo) (7 pages).

Final Rejection dated Sep. 19, 2019 by the USPTO for U.S. Appl. No. 14/718,955, filed May 21, 2015 and published as US 2015/0344965 A1 on Dec. 3, 2015 (Inventor—Jun Luo) (8 pages).

Commmunication pursuant to Article 94(3) EPC dated Jul. 8, 2019 by the European Patent Office for EP Application No. 15796390.1, which was filed on May 19, 2015 and published as EP 3146081 on Mar. 29, 2017 (Applicant—The John Hopkins University) (6 pages).

Final Rejection dated May 17, 2019 by the USPTO Office for U.S. Appl. No. 15/309,986, filed Nov. 9, 2016 and published as US-2017-0268063-A1 on Sep. 21, 2017 (Inventor—Luo et al.) (10 pages).

EP Communication dated Feb. 21, 2020 by the European Patent Office for EP Application No. 15835018.1, which was filed on Aug.

(56) References Cited

OTHER PUBLICATIONS 25, 2015 and published as EP 3186393 A1 on Jul. 5, 2017 (Applicant—The John Hopkins University) (8 pages).

* cited by examiner

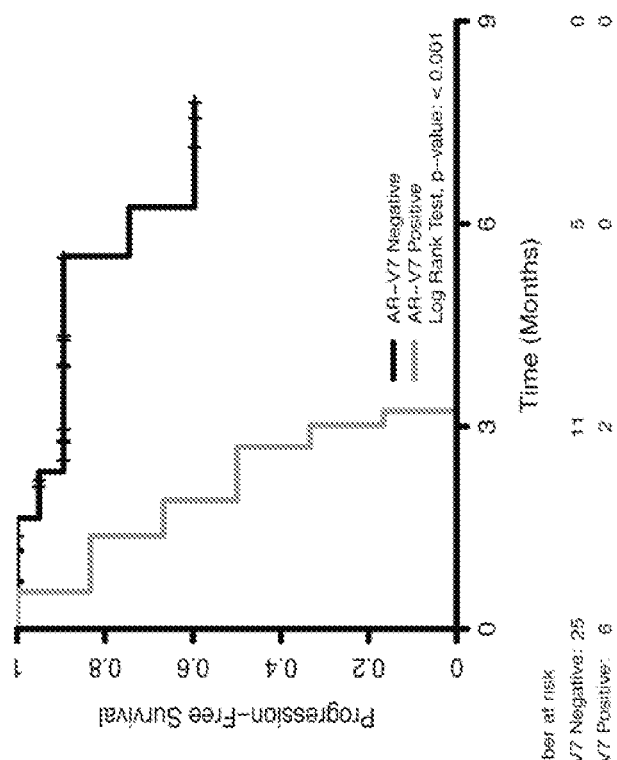
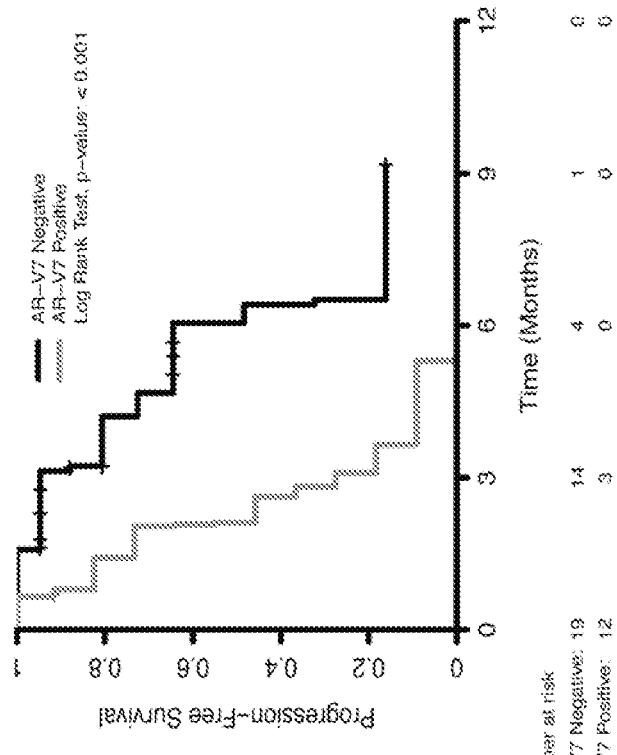
FIG. 5D
FIG. 5C

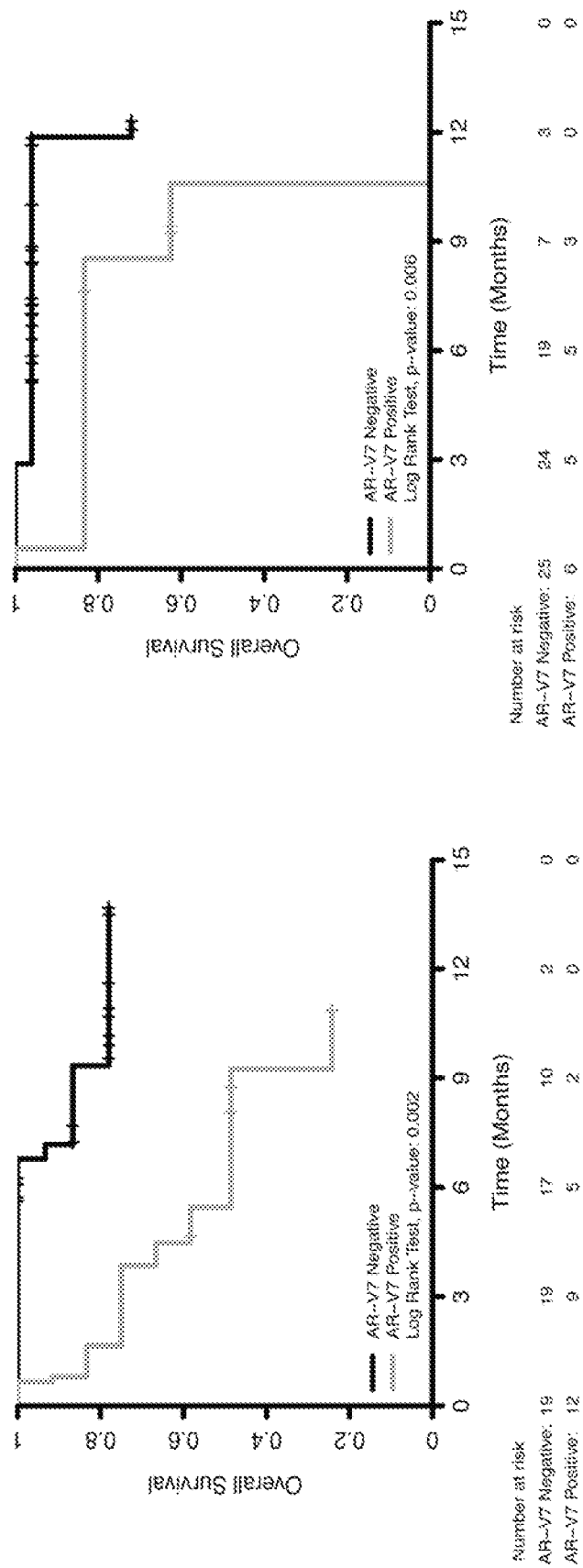

Figure S4 from ms

Positive enrichment in prostate related gene sets

| Gene Set Details | # of genes | ES | NES | Norm p-val | FDR q-val |
|---|---|---|---|---|---|
| 1. RESPONSE_TO_WOUNDING | 87 | 0.64 | 2.27 | 0 | 0 |
| 2. DEFENSE_RESPONSE | 105 | 0.61 | 2.18 | 0 | 0 |
| 3. CELLULAR_DEFENSE_RESPONSE | 16 | 0.86 | 2.18 | 0 | 0 |
| 4. RESPONSE_TO_EXTERNAL_STIMULUS | 135 | 0.57 | 2.16 | 0 | 0 |
| 5. INFLAMMATORY_RESPONSE | 60 | 0.63 | 2.12 | 0 | 0 |
| 6. M_PHASE_OF_MITOTIC_CELL_CYCLE | 67 | 0.61 | 2.08 | 0 | 0 |
| 7. G_PROTEIN_COUPLED_RECEPTOR_PROTEIN_SIGNALING_PATHWAY | 83 | 0.59 | 2.06 | 0 | 0.001 |
| 8. MITOSIS | 64 | 0.6 | 2.02 | 0 | 0.002 |
| 9. M_PHASE | 81 | 0.57 | 1.97 | 0 | 0.003 |
| 10. ORGAN_MORPHOGENESIS | 79 | 0.56 | 1.96 | 0 | 0.003 |

Negative enrichment in prostate related gene sets

| Gene Set Details | # of genes | ES | NES | Norm p-val | FDR q-val |
|---|---|---|---|---|---|
| 1. GOLGI_VESICLE_TRANSPORT | 47 | -0.38 | -1.49 | 0.033 | 1 |
| 2. CHROMATIN_ASSEMBLY_OR_DISASSEMBLY | 22 | -0.43 | -1.33 | 0.115 | 1 |
| 3. GAMETE_GENERATION | 44 | -0.34 | -1.27 | 0.114 | 1 |
| 4. MRNA_PROCESSING_GO_0006397 | 70 | -0.28 | -1.17 | 0.135 | 1 |
| 5. ER_TO_GOLGI_VESICLE_MEDIATED_TRANSPORT | 18 | -0.39 | -1.16 | 0.223 | 1 |
| 6. NEGATIVE_REGULATION_OF_TRANSCRIPTION_DNA_DEPENDENT | 94 | -0.25 | -1.12 | 0.184 | 1 |
| 7. MRNA_METABOLIC_PROCESS | 81 | -0.26 | -1.11 | 0.194 | 1 |
| 8. NEGATIVE_REGULATION_OF_RNA_METABOLIC_PROCESS | 95 | -0.26 | -1.1 | 0.259 | 1 |
| 9. SEXUAL_REPRODUCTION | 50 | -0.28 | -1.1 | 0.288 | 1 |
| 10. PROTEIN_AUTOPROCESSING | 22 | -0.34 | -1.1 | 0.303 | 1 |

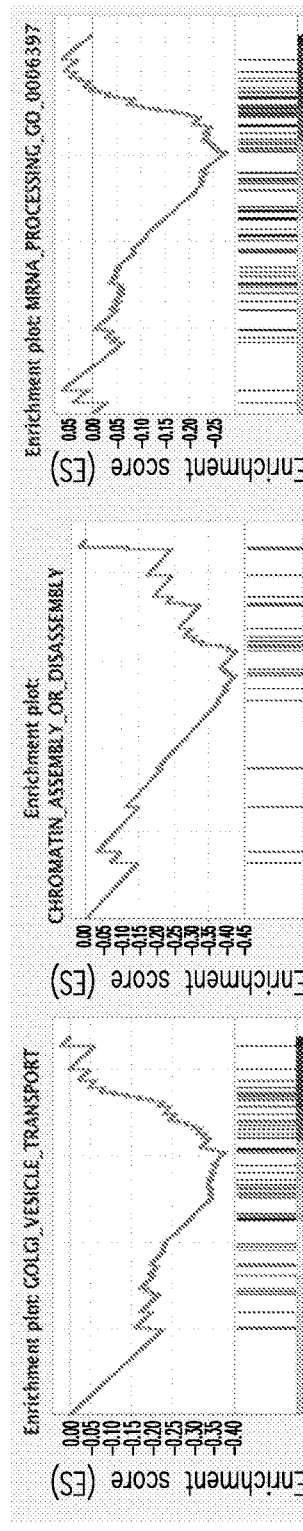
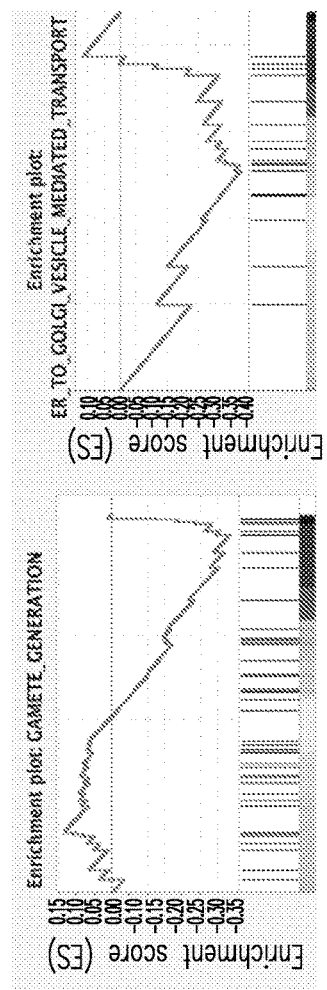

FIG. 12B

| Gene | Size (bp) | Raw V7(-) Met 1 | Raw V7(-) Met 2 | Raw V7(+) Met 1 | Raw V7(+) Met 2 | RPKM V7(-) Met 1 | RPKM V7(-) Met 2 | RPKM V7(+) Met 1 | RPKM V7(+) Met 2 | log FC | CSS | R1881 | CSS + ARV7 | R1881 + ARV7 | log FC by ARV7 | log FC by ARFL |
|---|---|---|---|---|---|---|---|---|---|---|---|---|---|---|---|---|
| AR | 4496 | 23044 | 20645 | 21722 | 62370 | 111.83 | 92.43 | 54.53 | 201.92 | -0.22 | 0.10 | -0.89 | -0.01 | -0.96 | -0.11 | -0.99 |
| C1orf116 | 5502 | 3123 | 5063 | 3293 | 10168 | 12.38 | 18.52 | 6.75 | 26.90 | -0.62 | -0.90 | 1.05 | -0.90 | 0.99 | 0.01 | 1.95 |
| CENPN | 5307 | 1337 | 11671 | 1799 | 907 | 5.50 | 44.27 | 3.83 | 2.49 | -3.26 | -2.67 | 0.52 | -1.92 | 0.86 | 0.75 | 3.20 |
| CXCR4 | 2005 | 654 | 695 | 10593 | 7739 | 7.12 | 6.98 | 59.63 | 56.18 | 2.65 | -0.40 | 2.77 | -0.26 | 3.51 | 0.13 | 3.17 |
| DBI | 1260 | 11624 | 10108 | 43384 | 10800 | 201.28 | 161.47 | 388.60 | 124.76 | 0.11 | -0.50 | 3.07 | 0.33 | 3.19 | 0.82 | 3.57 |
| EAF2 | 1020 | 66 | 212 | 3689 | 116 | 1.41 | 4.18 | 40.82 | 1.66 | 0.74 | 0.10 | 4.18 | 0.37 | 3.77 | 0.28 | 4.08 |
| EBP | 1157 | 784 | 3333 | 3322 | 2755 | 14.78 | 57.98 | 32.40 | 34.66 | -0.20 | -0.48 | 0.86 | -0.07 | 0.75 | 0.41 | 1.35 |
| FASN | 8458 | 2272 | 5891 | 19983 | 46976 | 5.86 | 14.02 | 26.66 | 80.84 | 1.97 | -0.50 | 0.61 | -0.06 | 0.86 | 0.44 | 1.11 |
| FKBP5 | 10628 | 3810 | 34978 | 55568 | 66987 | 7.82 | 66.24 | 59.01 | 91.74 | 1.32 | -1.28 | 3.61 | 1.26 | 4.03 | 2.54 | 4.89 |
| FZD5 | 6564 | 3247 | 6014 | 3756 | 2384 | 10.79 | 18.44 | 6.46 | 5.29 | -1.98 | -1.12 | 1.65 | -0.93 | 1.80 | 0.19 | 2.77 |
| HMGCR | 4582 | 2395 | 3169 | 3526 | 2334 | 11.40 | 13.92 | 8.68 | 7.41 | -1.25 | 0.06 | 1.54 | 0.07 | 1.27 | 0.01 | 1.49 |
| HMGCS1 | 3510 | 2596 | 5207 | 12367 | 3282 | 16.14 | 29.86 | 39.76 | 13.61 | -0.38 | 0.40 | 2.15 | 0.65 | 1.79 | 0.25 | 1.75 |
| HPGD | 3022 | 127 | 57 | 392 | 29067 | 0.92 | 0.38 | 1.46 | 140.00 | 3.64 | -2.52 | 3.46 | -0.05 | 4.05 | 2.47 | 5.98 |
| INSIG1 | 3081 | 421 | 3684 | 3118 | 8029 | 2.98 | 24.07 | 11.42 | 37.93 | 0.90 | -0.58 | 1.55 | 0.27 | 2.00 | 0.85 | 2.13 |
| KLK2 | 2872 | 286904 | 327838 | 82985 | 16542 | 2179.51 | 2297.62 | 326.10 | 83.84 | -3.76 | -4.34 | 0.14 | -3.86 | 0.37 | 0.48 | 4.48 |
| KLK3 | 2214 | 213712 | 922556 | 121923 | 32693 | 2106.00 | 8387.23 | 621.51 | 214.93 | -3.03 | -3.75 | -0.16 | -2.95 | 0.37 | 0.80 | 3.59 |
| KLK4 | 1347 | 2478 | 3956 | 813 | 4579 | 40.14 | 59.11 | 6.81 | 49.48 | -1.81 | -2.68 | -0.19 | -2.59 | -0.20 | 0.08 | 2.49 |
| LDLR | 5283 | 149 | 1947 | 2714 | 5261 | 0.62 | 7.42 | 5.80 | 14.49 | 1.47 | -0.82 | 1.70 | -0.23 | 1.50 | 0.60 | 2.52 |
| MAF | 6878 | 425 | 778 | 4311 | 1659 | 1.35 | 2.28 | 7.07 | 3.51 | 0.59 | -1.22 | 2.98 | -1.54 | 2.81 | -0.32 | 4.20 |
| MICAL1 | 3644 | 685 | 88 | 2959 | 2630 | 4.10 | 0.49 | 9.16 | 10.51 | 2.00 | 0.32 | 3.28 | 0.28 | 3.14 | -0.04 | 2.96 |
| NCAPD3 | 5605 | 849 | 1024 | 2601 | 4880 | 3.30 | 3.68 | 5.24 | 12.67 | 0.63 | -0.62 | 2.50 | -0.22 | 2.55 | 0.41 | 3.12 |
| NDRG1 | 3478 | 66845 | 19467 | 44162 | 124199 | 419.32 | 112.66 | 143.30 | 519.78 | 0.22 | -1.02 | 2.99 | 0.11 | 3.35 | 1.14 | 4.01 |
| NKX3-1 | 3281 | 35635 | 53042 | 44160 | 43298 | 236.96 | 325.40 | 151.90 | 192.08 | -0.89 | -2.62 | 1.17 | -2.59 | 1.04 | 0.04 | 3.80 |
| ORM1 | 839 | 3 | 2407 | 94992 | 21539 | 0.08 | 57.75 | 1277.81 | 373.67 | 7.90 | -0.88 | 4.10 | 6.70 | 6.47 | 7.57 | 4.97 |
| PMEPA1 | 5186 | 10061 | 16129 | 7660 | 5565 | 42.33 | 62.60 | 16.67 | 15.62 | -2.12 | -1.49 | 1.04 | -0.81 | 1.22 | 0.67 | 2.52 |
| PTPN21 | 6215 | 551 | 1684 | 565 | 2532 | 1.93 | 5.45 | 1.03 | 5.93 | -1.28 | 1.08 | 3.51 | 0.84 | 3.47 | -0.24 | 2.43 |

FIG. 13A

| RAB3B | 12844 | 2274 | 10492 | 8012 | 3620 | 3.86 | 16.44 | 7.04 | 4.10 | -1.33 | -1.39 | 1.25 | -1.14 | 1.22 | 0.25 | 2.64 |
|---|---|---|---|---|---|---|---|---|---|---|---|---|---|---|---|---|
| RHOU | 4758 | 16379 | 28644 | 5876 | 7735 | 75.11 | 121.17 | 13.94 | 23.66 | -2.77 | 0.28 | 3.58 | 0.34 | 3.71 | 0.06 | 3.30 |
| SCAP | 4255 | 609 | 869 | 1134 | 4593 | 3.12 | 4.11 | 3.01 | 15.71 | 0.34 | -0.29 | 0.76 | -0.11 | 0.99 | 0.18 | 1.05 |
| SGK1 | 3965 | 105 | 24777 | 20302 | 1347 | 0.58 | 125.78 | 57.79 | 4.94 | 0.24 | -0.10 | 3.35 | -0.05 | 3.62 | 0.05 | 3.45 |
| SLC45A3 | 3382 | 5108 | 7039 | 2578 | 15489 | 32.95 | 41.89 | 8.60 | 66.66 | -1.03 | -2.52 | 1.07 | -2.29 | 1.42 | 0.23 | 3.59 |
| TMPRSS2 | 3320 | 4457 | 54020 | 27831 | 19920 | 29.29 | 327.51 | 94.61 | 87.33 | -0.53 | -4.59 | -0.38 | -3.92 | 0.09 | 0.67 | 4.21 |
| WIPI1 | 1924 | 209 | 435 | 6828 | 1472 | 2.37 | 4.55 | 40.05 | 11.14 | 2.15 | -0.10 | 2.57 | 0.98 | 2.86 | 1.08 | 2.67 |
| WWC1 | 6739 | 2465 | 1922 | 6536 | 5735 | 7.98 | 5.74 | 10.95 | 12.39 | 0.26 | -0.75 | 0.16 | -0.99 | 0.21 | -0.23 | 0.91 |
| ZNF350 | 2341 | 2985 | 3161 | 5862 | 1155 | 27.82 | 27.18 | 28.26 | 7.18 | -1.54 | 0.27 | 1.27 | 0.18 | 1.35 | -0.09 | 1.00 |

FIG. 13B

METHODS AND COMPOSITIONS RELATED TO PROSTATE CANCER THERAPEUTICS

CROSS-REFERENCE TO RELATED APPLICATIONS

This application claims the benefit of and priority under 35 U.S.C. § 371 to PCT/US2015/043806, filed Aug. 25, 2015, which claims the benefit under 35 U.S.C. § 119(e) to U.S. Patent Application No. 62/041,368, filed Aug. 25, 2014, the benefit of U.S. Patent Application No. 62/120,877, filed Feb. 26, 2015, and the benefit of U.S. Patent Application No. 62/149,408, filed Apr. 17, 2015. Each application is hereby incorporated by reference in-its entirety.

STATEMENT REGARDING FEDERALLY SPONSORED RESEARCH OR DEVELOPMENT

This invention was made with government support under grant no. W81XWH-12-1-0605 awarded by the DOD Prostrate Cancer Research Program, grant no. P50 CA058236 and grant no. P30 CA006973 awarded by the National Institute of Health (NIH). The government has certain rights in the invention.

REFERENCE TO SEQUENCE LISTING

The Sequence Listing submitted Feb. 22, 2017 as a text file named "36406_0008U4_Sequence_Listing.txt" created on Feb. 15, 2017, and having a size of 4,096 bytes is hereby incorporated by reference pursuant to 37 C.F.R. § 1.52(e)(5).

TECHNICAL FIELD

This disclosure relates to the field of molecular biology and protein biology involving the detection biological molecules and biomarkers. This application also relates to the fields of tumor biology, cancer, and specifically prostate cancer.

BACKGROUND

Knowledge of the molecular basis of cancer potentially expands the number of strategies to target cancer cells for therapy. Multiple genetic alterations in cancer frequently result in aberrations in the biochemical properties of signaling molecules and other biomarkers leading to disruption of biological mechanisms in tumors and consequently malignant progression.

Prostate cancer (PCa) depends on androgenic signaling for growth and survival. Androgens exert their cellular and physiologic effects through binding to the androgen receptor (AR), a member of the steroid hormone receptor family of transcription factors. The human AR gene is located on chromosome Xq11-12 and spans approximately 180 kb of DNA with eight known exons. The prototype AR protein contains several functional domains. The NH2-terminal domain (NTD), encoded by exon 1, constitutes approximately 60% of the 110-kDa full-length protein and is the transcriptional regulatory region of the protein. The central DNA-binding domain (DBD) is encoded by exons 2 and 3, whereas exons 4 to 8 code for the COOH-terminal ligand-binding domain (LBD). Androgen binding to the AR LBD allows entry of the ligand-bound receptor into the nucleus and subsequent transcriptional regulation of androgen-responsive genes.

Hormonal therapy has been used since 1941 for the treatment of metastatic prostate cancer. Androgen deprivation therapies (ADT) employing surgical and/or medical castration as well as their combination with anti-androgens have since become the mainstay of systemic treatment for advanced prostate cancer. ADT for advanced PCa, target AR-mediated functions by suppressing the production of androgens and/or androgen binding to the AR LBD. In a contemporary clinical setting, the length of clinical remission, often assessed by serum prostate-specific antigen (PSA) measurements, varies substantially due to a wide spectrum of clinical phenotypes among treated patients. Almost invariably, however, prostate cancer develops castration-resistant phenotype and progresses to a life-threatening stage, despite ADT. The widespread use of ADT is manifested in the observation that almost all patients who die from prostate cancer had received and failed androgen-deprivation therapies.

What is needed are methods and compositions for treating prostate cancer and for proactively designing effective therapeutic regimens for patients having resistance to certain drugs and treatments.

SUMMARY

The present disclosure comprises methods and compositions for treating prostate cancer and effective therapeutic regimens for patients having resistance to certain drugs and treatments. The methods and compositions disclosed herein may comprise peptides, polypeptides, antibodies, nucleic acids, vectors, and host cells for making, using, assaying, and evaluating biological aspects of prostate cancer, included but not limited to, detecting biomarkers associated with therapeutic drug resistance.

Methods of the present disclosure comprise methods for detecting the presence of certain androgen receptors, or androgen receptor variants. Methods may comprise detecting the presence of androgen receptor variants such as AR-V7 in bodily fluid samples from prostate cancer patients. Methods may also comprise detecting the presence of androgen receptor variants such as AR-V7 in bodily fluid samples from prostate cancer patients wherein the samples comprise circulating tumor cells from patients with castration-resistant prostate cancer. Methods comprise treating prostate cancer patients who have been identified by methods disclosed herein. Such treatments may comprise determining the level of expression or biological activity of an androgen receptor variant polypeptide in a patient sample wherein an elevation in the level of expression or biological activity relative to the expression or biological activity in a reference indicates that the patient will not respond to androgen therapy; and administering a therapy selected from the group consisting of chemotherapy, radiotherapy, immunotherapy and a pharmaceutical composition that alters expression of an androgen receptor variant polypeptide to the patient identified as having said elevation.

BRIEF DESCRIPTION OF THE FIGURES

FIGS. 5C and 5D show representative data pertaining to Kaplan-Meier analysis of clinical/radiographic-progression-free-survival [PFS] stratified by AR-V7 status in either enzalumatide-treated patients (5C) or abiraterone-treated patients (5D). Median PFS in enzalutamide-treated patients (C) was 2.1 months (95% CI, 2.0—not reached) and 6.1 months (95% CI, 4.7—not reached) in AR-V7-positive and AR-V7-negative patients, respectively (HR 8.5, 95% CI 2.8-25.5, log-rank P<0.001). Median PFS in abiraterone-treated patients (D) was 2.3 months (95% CI, 1.4—not reached) and >6.3 months (95% CI, 6.3—not reached) in AR-V7-positive and AR-V7-negative patients, respectively (HR 16.5, 95% CI 3.3 82.9, log-rank P<0.001). FIGS. 5E and 5F shows representative data pertaining to Kaplan-Meier analysis of overall survival [OS] stratified by AR-V7 status in either enzalumatide-treated patients (5E) or abiraterone-treated patients (5F). Median OS in enzalumatide-treated patients (E) was 5.5 months (95% CI, 3.9—not reached) and not reached (95% CI, not reached-not reached) in AR-V7-positive and AR-V7-negative patients, respectively (HR 6.9, 95% CI 1.7-28.1, log-rank P=0.002). Median OS in abiraterone-treated patients (F) was 10.6 months (95% CI, 8.5—not reached) and >11.9 months (95% CI, 11.9—not reached) in AR-V7-positive and AR-V7-negative patients, respectively (HR 12.7, 95% CI 1.3-125.3, log-rank P=0.006).

FIG. 13 (A and B) provides Table 11 showing expression profiles of AR-regulated genes in AR-V7-negative and AR-V7-positive metastatic tumors and cell lines.

AR-FL levels are also shown for the AR-V7-negative samples. In addition, there were 6 patients (not shown) who were negative for AR-FL, all of which were also negative for AR-V7. Detection of AR-V7 was associated with increased expression of AR-FL (P<0.001).

Figure 15:
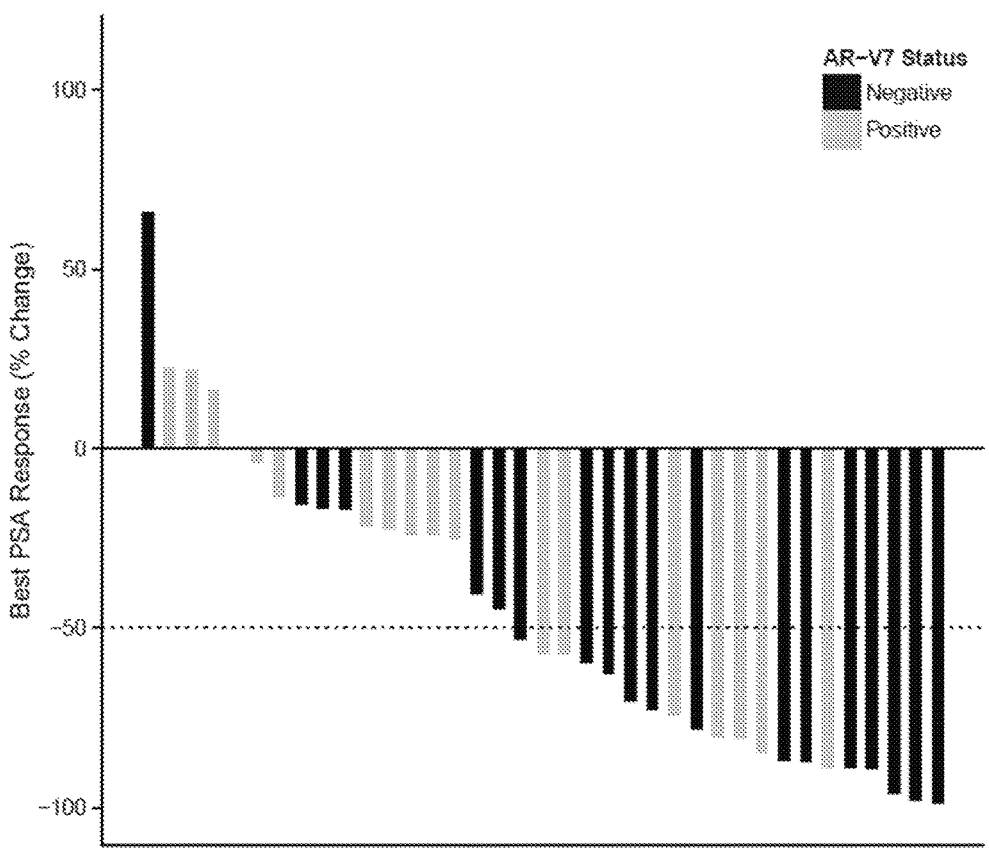

FIG. 15 is a waterfall plot depicting best PSA responses according to CTC AR-V7 status in 37 taxane-treated patients. The dotted line shows the threshold for defining a PSA response (≥50% PSA reduction from baseline). Among patients that achieved a PSA response, 35% (7/20 men) were AR-V7-positive; while in those patients without a PSA response, 59% (12/17 men) were AR-V7-positive.

FIGS. 16 A-C. Clinical outcomes in taxane-treated patients and enzalutamide/abiraterone-treated patients, stratified by AR-V7 status. 16A shows Kaplan-Meier analysis showing PSA progression-free survival (PSA-PFS) in taxane-treated patients (solid lines) and enzalutamide/abiraterone-treated patients (dotted lines), separated according to AR-V7 status. A positive interaction between AR-V7 status and treatment types was observed (adjusted P=0.001). 16B shows Kaplan-Meier analysis showing clinical/radiographic progression-free survival (PFS) in taxane-treated patients (solid lines) and enzalutamide/abiraterone-treated patients (dotted lines), according to AR-V7 status. A positive interaction between AR-V7 status and treatment types was observed (adjusted P=0.003). 16C shows Kaplan-Meier analysis showing overall survival (OS) in taxane-treated patients (solid lines) and enzalutamide/abiraterone-treated patients (dotted lines), according to AR-V7 status. A significant interaction between AR-V7 status and treatment types was not observed (adjusted P=0.16).

Figure 17:
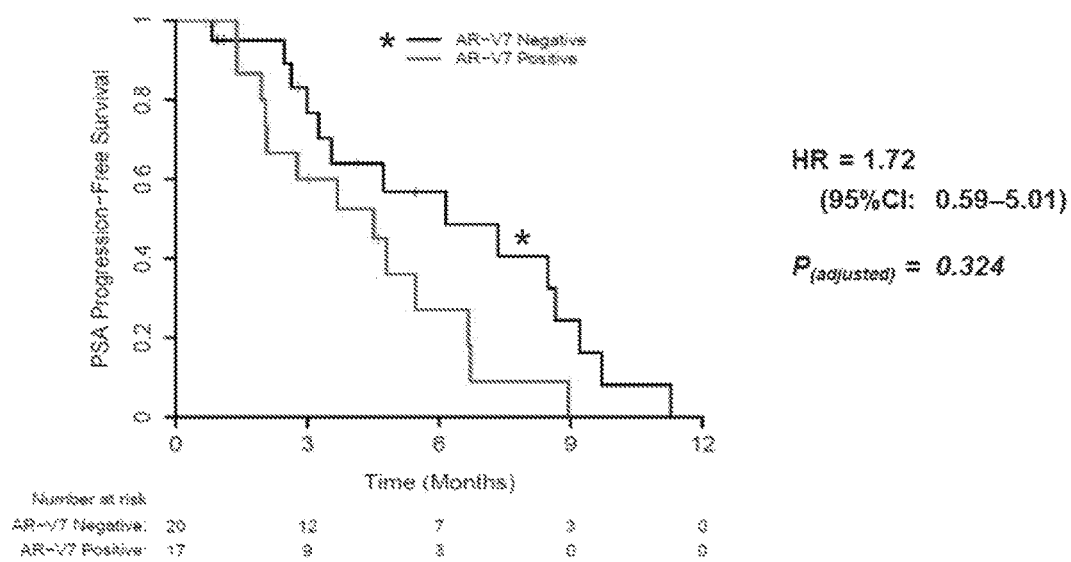

FIG. 17 is a graph showing PSA progression-free survival for AR-V7 positive or negative subjects, respectively.

Figure 18:
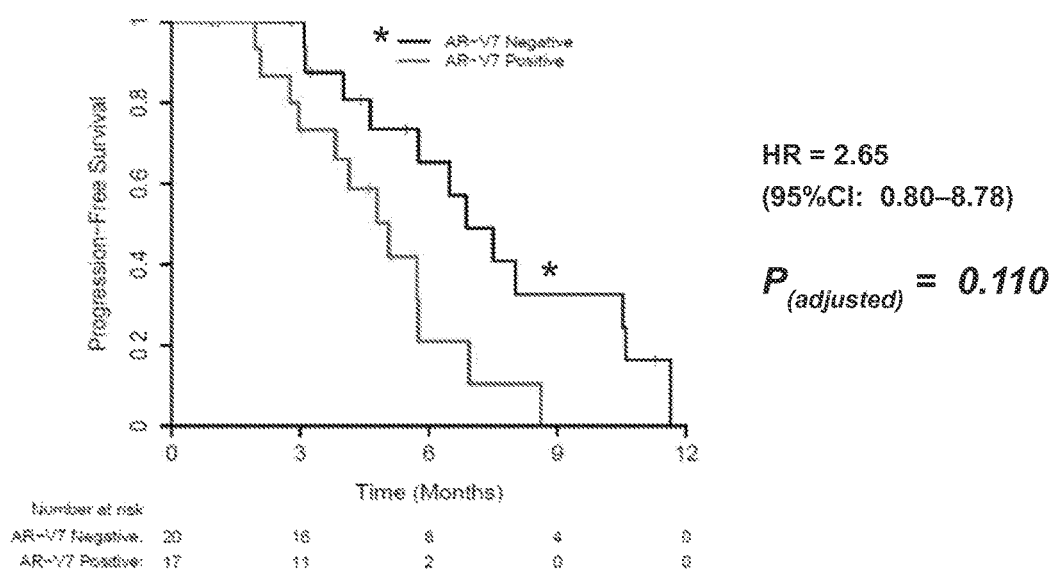

FIG. 18 is a graph showing progression-free survival of subjects who are AR-V7 positive or negative, respectively.

Figure 19A:
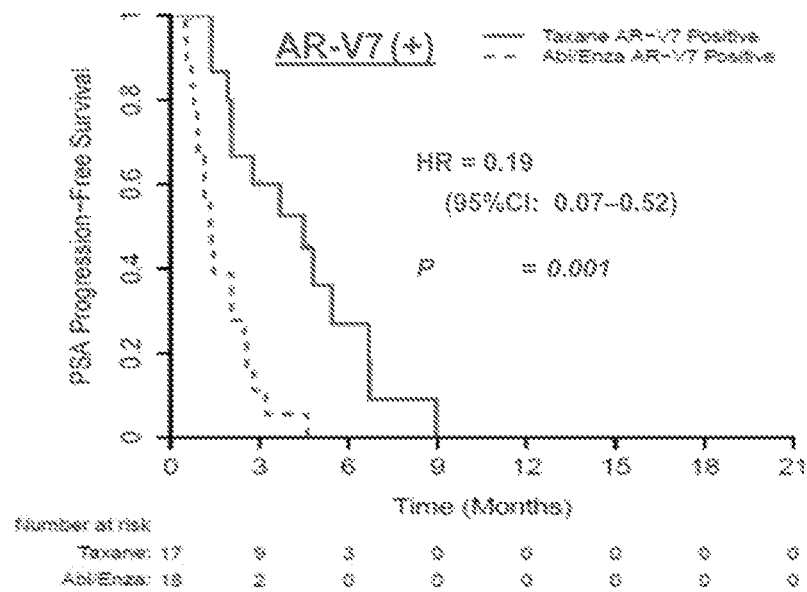
Figure 19B:
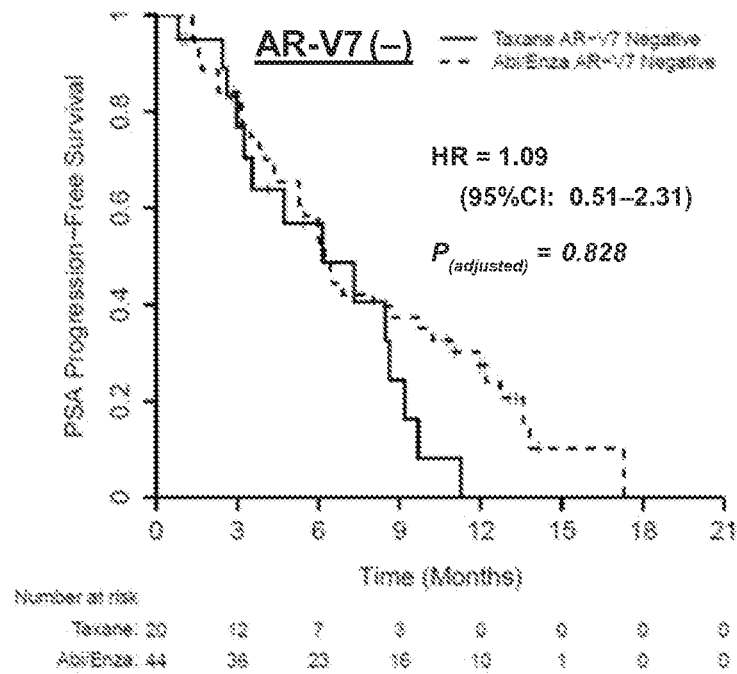
Figure 20A:
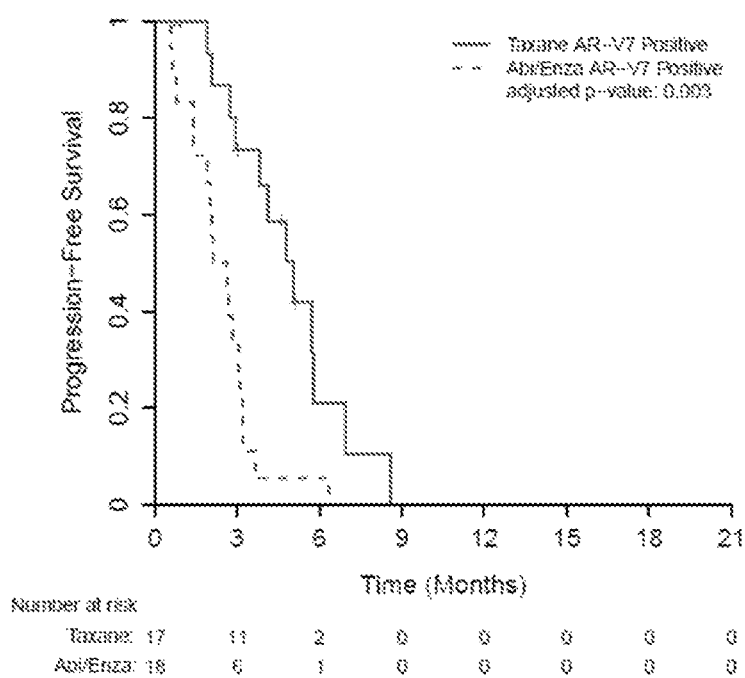
Figure 20B:
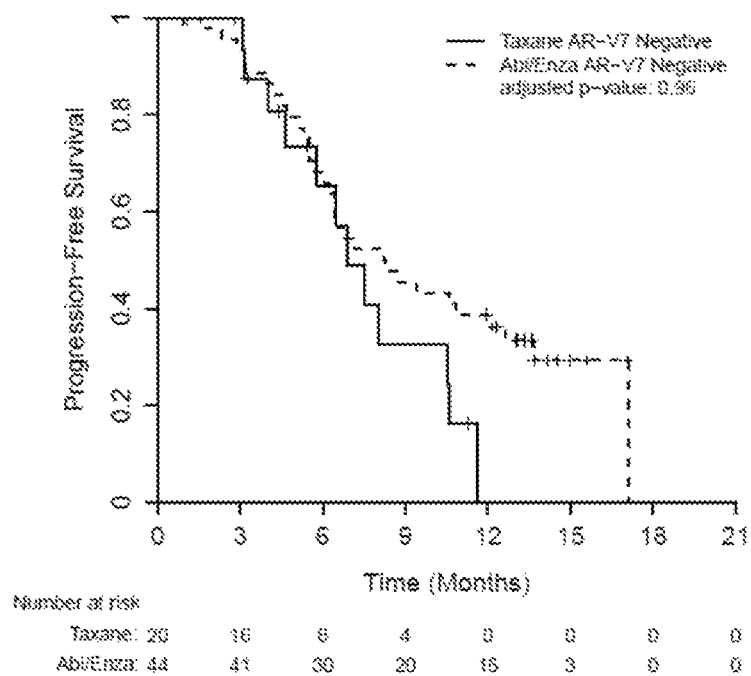
Figure 20C:
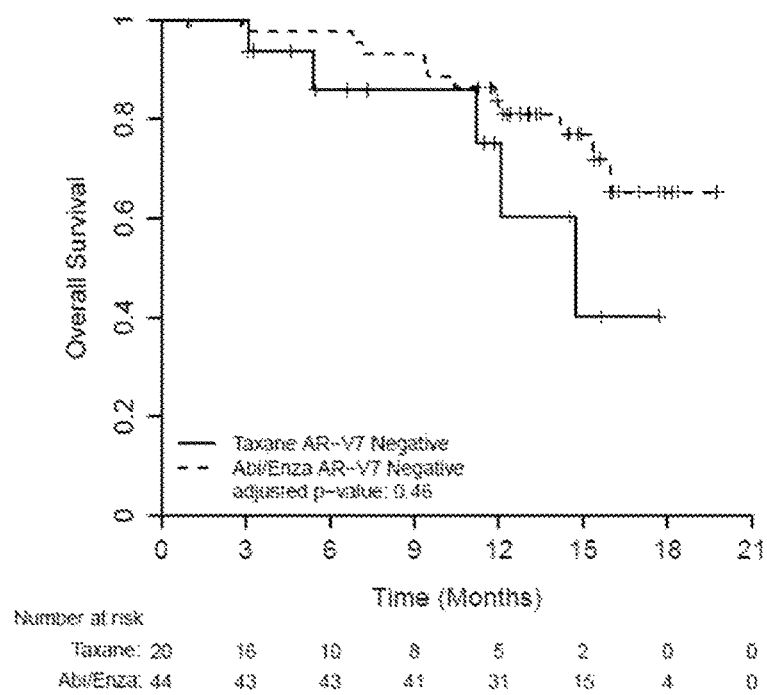
Figure 20D:
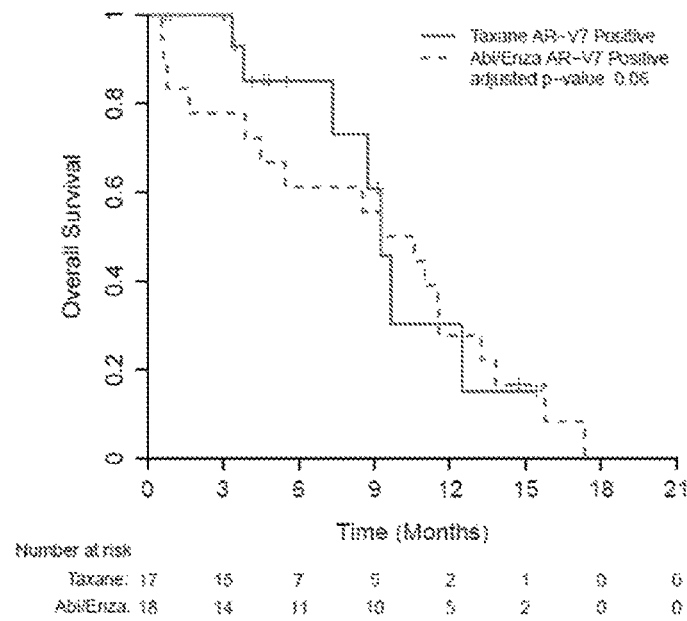

FIGS. 19 A-B are graphs showing PSA-PFS for taxane-treated vs enzalutamide/abiraterone-treated subjects who are AR-V7 positive or negative, respectively.

FIGS. 20 A-D are graphs showing, for taxane-treated vs enzalutamide/abiraterone-treated subjects who are AR-V7 positive or negative, (A) progression-free survival (AR-V7 positive), (B) progression-free survival (AR-V7 negative), and (C-D) overall survival.

DETAILED DESCRIPTION

Disclosed herein are methods and compositions for detecting biological molecules and biomarkers associated with prostate cancer, including castration-resistant prostate cancer, wherein such biological molecules and biomarkers are useful for determining therapeutic regimens for prostate cancer patients. Methods disclosed herein enable the detection of prostate cancer that is resistant to certain drugs and therapeutic intervention, and detects therapeutic agents that are effective for treatment of prostate cancer. Methods disclosed herein comprise treatment of subjects with prostate cancer who have been identified to have biomarkers disclosed herein.

A few lines of evidence have established that, unlike human breast cancer, prostate cancer progression upon hormone therapy is not due to loss of dependence on hormonal signaling but, instead, characterized by sustained androgenic signaling that bypasses the requirement for physiological levels of androgens. First, with only certain exceptions, prostate cancer patients dying from castration-resistant prostate cancer (CRPC) have very high levels of serum PSA, the production of which is driven by androgenic signaling. Second, CRPCs have elevated expression levels of the key mediator of androgenic signaling, the AR, and this is a very consistent molecular feature in tissues derived from patients with CRPC. Third, a subset of prostate cancers that relapsed following first-line ADT continue to respond to second-line therapies designed to disrupt the AR signaling axis, suggesting that AR-mediated androgenic signaling is still operating among these CRPC tumors. While it is possible that AR-negative prostate cancer cells may give rise to androgen-independent prostate carcinoma, prostate tumors comprised of mainly AR-negative malignant cells (i.e., small cells and neuroendocrine cells) are rare.

Therefore, it is well established that AR-mediated functions are not completely abrogated by the existing androgen and androgen receptor-directed therapies. CRPC continues to depend on AR-mediated functions but bypasses the requirement for physiologic levels of androgens. Molecular alterations involving AR itself, such as AR overexpression and gain-of-function AR LBD mutations, are common in CRPC and allow for continued AR-mediated genomic functions under the presence of reduced or altered ligands. An alternative mechanism for CRPC is the presence or elevated expression of AR variants lacking the AR LBD.

It is now accepted that castration-resistant prostate cancer (CRPC) is not androgen-independent and continues to rely on androgen signaling (Longo, D. L. (2010) The New England Journal of Medicine 363, 479-481). Due to this new appreciation, several drugs have recently emerged for the treatment of CRPC; these agents either suppress the synthesis of extra-gonadal androgens or target the androgen receptor (AR) directly (Ryan, C. J. and Tindall, D. J. (2011) Journal of Clinical Oncology: Official Journal of the American Society of Clinical Oncology 29, 3651-3658). For example, enzalutamide is an AR signaling inhibitor which exerts its activity by avidly binding to the AR ligand-binding domain, competing with and displacing the natural ligands of this receptor (testosterone and dihydrotestosterone), while also inhibiting AR translocation into the nucleus and impairing transcriptional activation of androgen-responsive target genes (Tran, C., et al. (2009) Science 324, 787-790; Scher, H. I., et al. (2010) Lancet 375, 1437-1446). Another example of a new drug comprises abiraterone which is a CYP17 inhibitor that impairs AR signaling by depleting adrenal and intratumoral androgens (O'Donnell, A., et al. (2004) British Journal of Cancer 90, 2317-2325; Attard, G., et al. (2008) Journal of Clinical Oncology: Official Journal of the American Society of Clinical Oncology 26, 4563-4571). Both enzalutamide and abiraterone agents are FDA-approved for the treatment of men with metastatic CRPC, after demonstrating improvements in survival (Scher, H. I., et al. (2012) New England Journal of Medicine 367, 1187-1197; Ryan, C. J., et al. (2013) New England Journal of Medicine 368, 138-148; de Bono, J. S., et al. (2011) New England Journal of Medicine 364, 1995-2005).

There are currently six available therapies for the treatment of castration-resistant prostate cancer (CRPC), all of which have produced survival improvements.[1] These therapies fall into four classes: androgen receptor (AR)-directed therapies (abiraterone,[2] enzalutamide[3], taxane chemotherapies (docetaxel,[4] cabazitaxel[5]) immunotherapies (sipuleucel-T[6]) and bone-targeting radiopharmaceuticals (radium-223).[7] Of these, the most widely used are the AR-targeting therapies and the chemotherapies. However, mechanisms of response and resistance to these therapies remain poorly understood.[8,9] Further, predictive biomarkers aiding in treatment selection (i.e. selecting for or against a particular therapy) are still lacking, while prognostic markers are abundant.[10]

Although enzalutamide and abiraterone represent significant breakthroughs in the treatment of metastatic CRPC, approximately 20-40% of patients show no PSA responses (i.e., demonstrate primary resistance) to these agents (Scher, H. I., et al. (2010) Lancet 375, 1437-1446; Scher, H. I., et al. (2012) New England Journal of Medicine 367, 1187-1197; Ryan, C. J., et al. (2013) New England Journal of Medicine 368, 138-148; de Bono, J. S., et al. (2011) New England Journal of Medicine 364, 1995-2005). Among patients who initially respond to enzalutamide or abiraterone, virtually all eventually develop secondary (acquired) resistance. The mechanisms underlying enzalutamide and abiraterone resistance in patients with CRPC are largely unknown, representing an area of unmet medical need.

Methods and compositions disclosed herein can be used to evaluate the predictive impact of AR-Vs in men with CRPC undergoing taxane chemotherapy. Though not wishing to be bound by any particular theory, it is thought that men with detectable CTC-derived AR-V7 would retain sensitivity to taxanes, and that AR-V7 status would have a differential effect on taxane-treated men versus enzalutamide/abiraterone-treated men. Data disclosed herein show detection of AR-V7 is not associated with primary resistance to taxane chemotherapy, and that taxanes may have superior efficacy compared to AR-targeting agents in AR-V7-positive patients.

AR-Vs are alternatively-spliced transcriptional variants of the AR that encode a truncated AR protein lacking the C-terminal ligand-binding domain but retaining the transactivating N-terminal domain (Dehm, S. M., et al. (2008) Cancer Research 68, 5469-5477; Hu, R., et al. (2009) Cancer Res 69, 16-22). Although these AR-Vs are unable to bind ligand, they are constitutively-active and capable of promoting activation of target genes. The clinical significance of AR-Vs in patients receiving enzalutamide or abiraterone was heretofore unknown.

Detection methods, such as PCR, including quantitative reverse-transcription polymerase chain reaction (qRT-PCR), are used to assess circulating tumor cells (CTCs) for the presence or absence of AR-Vs, in particular the AR-V known as AR-V7. By analyzing CTCs and examining the associations between AR-V7 status and PSA response rates, PSA-progression-free-survival (PSA-PFS), clinical/radiographic-progression-free survival (PFS), and overall survival (OS), the independent effect of AR-V7 status on clinical outcomes was determined. In an aspect, detection of AR-V7 in CTCs from patients with castration-resistant prostate cancer may be used to asses the response to therapeutic agents, for example, therapeutic agents such as taxanes, or resistance to drugs such as enzalutamide and abiraterone. As used herein, therapeutic agent and chemotherapeutic agent may be used interchangeably.

Disclosed herein are methods of assessing resistance to a therapeutic agent in a subject diagnosed with prostate cancer comprising the detection of AR-V7 in a bodily fluid of a subject diagnosed with prostate cancer. For example, the presence of AR-V7 indicates resistance to a therapeutic agent. The prostate cancer may be castration-resistant prostate cancer and the therapeutic agent may comprise at least one taxane, enzalutamide or abiraterone, or other therapeutic agents known to those of skill in the art. The bodily fluid may be plasma, serum, or peripheral blood, or other bodily fluids. The bodily fluid, for example, plasma, serum or peripheral blood, may comprise circulating tumor cells. The bodily fluid may be collected at multiple time points, before diagnosis, following diagnosis of prostate cancer or during the course of treatment: at baseline, at a clinical/biochemical response, and at a clinical/radiographic progression. The clinical/biochemical response may comprise measurement of prostate specific antigen and the clinical/radiographic progression may comprise monitoring symptomatic progression, including but not limited to worsening disease-related symptoms, cancer-related complications, radiologic progression, enlargement in sum diameter of soft-tissue target lesions, increase in number of bone lesions, or death. The presence of AR-V7 is determined by detection assays known those skilled in the art, such as protein or peptide detection methods and/or molecular biological detection, including but not limited to PCR, qRT-PCR, sequencing, Northern, Southern or Western blots, chip arrays, and antibody assays. In certain embodiments, the PCR assays used to detect AR-V7 comprise the use of primers, wherein the primers may comprise one or more of SEQ ID NOS: 1-2 (AR-V7 (forward) 5'-CCATCTTGTCGTCTTCGGAAATGTIA-3' SEQ ID NO: 1; AR-V7 (reverse) 5'-TIGAAT-GAGGCAAGTCAGC-CTTTCT-3' SEQ ID NO:2). In certain embodiments, the methods further comprise measuring the amount of AR-FL, and comparing the amount of AR-V7 and AR-FL, in such embodiments, measuring the amount of AR-FL may comprises the use of primers, wherein the primers may comprise one or more of SEQ ID NOS: 3-4 (AR-FL (forward) 5'-CAGCCTATTGCGAGAGAGCTG-3' SEQ ID NO:3; AR-FL (reverse) 5'-GAAAGGATCTTGGGCACTTGC-3' SEQ ID NO:4).

Disclosed herein are methods for assessing whether a subject having castration-resistant prostate cancer has resistance to a therapeutic agent comprising detecting the presence of AR-V7 in a bodily fluid of a subject diagnosed with prostate cancer, wherein the bodily fluid comprises circulating tumor cells, and wherein detection of AR-V7 is an independent factor for indicating resistance to a therapeutic agent. For example, detection of AR-V7 is an indicator or biomarker resistance to the therapeutic agents enzalutamide and/or abiraterone. An aspect of the disclosure comprises methods for determining that a subject with castration-resistant prostate cancer does not have resistance to a therapeutic agent comprising detecting the presence of AR-V7 in a bodily fluid of a subject diagnosed with prostate cancer, wherein the bodily fluid comprises circulating tumor cells, and wherein detection of AR-V7 is an independent factor for indicating little to no resistance to a therapeutic agent, for example, the therapeutic agent may be a taxane. Disclosed herein are methods for determining a therapeutic regimen for a subject with castration-resistant prostate cancer comprising detecting the present of AR-V7 in a bodily fluid of a subject diagnosed with prostate cancer, wherein a bodily fluid may comprise circulating tumor cells, and wherein detection of AR-V7 isn independent factor for indicating that an effective therapeutic agent is a taxane. The bodily fluid may be collected at one or more time points following diagnosis of prostate cancer or during the course of treatment: at baseline, at a clinical/biochemical response, and at a clinical/radiographic progression. The clinical/biochemical response may comprise measurement of prostate specific antigen and the clinical/radiographic progression may comprise monitoring symptomatic progression, including but not limited to worsening disease-related symptoms, cancer-related complications, radiologic progression, enlargement in sum diameter of soft-tissue target lesions, increase in number of bone lesions, or death. The presence of AR-V7 is determined by detection assays known to those skilled in the art, including but not limited to, PCR, detection of peptide or proteins, molecular biological detection, sequencing, Northern Southern or Western blots, chip arrays and antibody assays. In certain embodiments, the PCR assays used to detect AR-V7 comprise the use of primers, wherein the primers may comprise one or more of SEQ ID NOS: 1-2. In certain embodiments, the methods further comprise measuring the amount of AR-FL, and comparing the amount of AR-V7 and AR-FL, in such embodiments, measuring the amount of AR-FL (full length androgen receptor) may comprises the use of primers, wherein the primers may comprise one or more of SEQ ID NOS: 3-4.

Disclosed herein are methods for determining a therapeutic regimen for a subject diagnosed with castration-resistant prostate cancer comprising, detecting the presence of AR-V7 in a bodily fluid of a subject diagnosed with prostate cancer, wherein the bodily fluid comprises circulating tumor cells, and wherein the detection of AR-V7 indicates that the patient has prostate cancer that is resistant to treatment by certain therapeutic agents. The therapeutic agents may comprise enzalutamide or abiraterone. Disclosed herein are methods for determining a therapeutic regimen for a subject diagnosed with castration-resistant prostate cancer comprising, detecting the presence of AR-V7 in a bodily fluid of a subject diagnosed with prostate cancer, wherein the bodily fluid comprises circulating tumor cells, and wherein the detection of AR-V7 indicates that the patient has prostate cancer that is not resistant to treatment by certain therapeutic agents, for example, the therapeutic agents may comprise a taxane. The bodily fluid may be collected at multiple time points following diagnosis of prostate cancer or during the course of treatment: at baseline, at a clinical/biochemical response, and at a clinical/radiographic progression. The clinical/biochemical response may comprise measurement of prostate specific antigen and the clinical/radiographic progression may comprise monitoring symptomatic progression, including but not limited to worsening disease-related symptoms, cancer-related complications, radiologic progression, enlargement in sum diameter of soft-tissue target lesions, increase in number of bone lesions, or death. The presence of AR-V7 is determined by detection assays known those skilled in the art, including but not limited to, PCR. In certain embodiments, PCR assays used to detect AR-V7 comprise the use of primers, wherein the primers may comprise one or more of SEQ ID NOS: 1-2. In certain embodiments, the methods further comprise measuring the amount of AR-V7 and AR-FL, in such embodiments, measuring the amount of AR-FL may comprises the use of primers, wherein the primers may comprise one or more of SEQ ID NOS: 3-4.

Disclosed herein are methods for treating a subject diagnosed with castration-resistant prostate cancer, wherein the subject has been determined to have the presence and/or amount of AR-V7 in a bodily fluid, the bodily fluid may comprise circulating tumor cells, and wherein the detection of AR-V7 indicates that the patient has prostate cancer that is resistant to treatment by certain therapeutic agents, and treating the subject with other cancer treatment methods known to those of skill in the art. Such treatments may comprise determining the level of expression or biological activity of an androgen receptor variant polypeptide in a patient sample wherein an elevation in the level of expression or biological activity relative to the expression or biological activity in a reference indicates that the subject will not respond to androgen therapy; and administering a treatment therapy, including but not limited to, chemotherapy, radiotherapy, immunotherapy or a pharmaceutical composition that alters expression of an androgen receptor variant polypeptide (e.g., AR-V7) to the subject identified as having said elevation. Therapeutic agents may comprise one or more taxanes, enzalutamide or abiraterone. Disclosed herein are methods for treating a subject diagnosed with castration-resistant prostate cancer having AR-V7 in a bodily fluid of the subject, wherein the bodily fluid comprises circulating tumor cells, and wherein the detection of AR-V7 indicates that the patient has prostate cancer that is either not resistant to treatment by certain therapeutic agents, e.g., a taxane, or is resistant to certain therapeutic agents, e.g., enzalutamide and/or abiraterone, and treating the subject with a treatment therapy, including but not limited to, chemotherapy, radiotherapy, immunotherapy or a pharmaceutical composition/therapeutic agent. The bodily fluid may be collected at multiple time points following diagnosis of prostate cancer or during the course of treatment: at baseline, at a clinical/biochemical response, and at a clinical/radiographic progression. The clinical/biochemical response may comprise measurement of prostate specific antigen and the clinical/radiographic progression may comprise monitoring symptomatic progression, including but not limited to worsening disease-related symptoms, cancer-related complications, radiologic progression, enlargement in sum diameter of soft-tissue target lesions, increase in number of bone lesions, or death. The presence of AR-V7 is measured by detection assays known those skilled in the art, including but not limited to, PCR or antibodies specific for AR-V7. In certain embodiments, PCR assays used to detect AR-V7 comprise the use of primers, wherein the primers may comprise one or more of SEQ ID NOS: 1-2. In certain embodiments, the methods further comprise measuring the amount of AR-FL, and comparing the amount of AR-V7 and AR-FL, in such embodiments, measuring the amount of AR-FL may comprises the use of primers, wherein the primers may comprise one or more of SEQ ID NOS: 3-4.

Disclosed herein are methods for utilizing the detection of AR-V7 as a treatment selection marker. For example, disclosed herein are methods for determining a therapeutic regimen for a subject diagnosed with castration-resistant prostate cancer comprising, detecting the presence of AR-V7 in a bodily fluid of a subject diagnosed with prostate cancer, wherein the bodily fluid comprises circulating tumor cells, wherein the detection of AR-V7 results in determining a therapeutic regimen including or not including one or more therapeutic agents. For example, a subject with prostate cancer may be found to resistant to treatment by certain therapeutic agents, wherein the detection of AR-V7, such as by PCR, indicates that the patient is or is not a candidate for a particular therapy. In an aspect, disclosed herein are methods for utilizing the detection of AR-V7 as a treatment selection marker. For example, disclosed herein are methods for determining a therapeutic regimen for a subject diagnosed with castration-resistant prostate cancer comprising, detecting the presence of AR-V7 in a bodily fluid of a subject diagnosed with prostate cancer, wherein the bodily fluid comprises circulating tumor cells, wherein the detection of AR-V7 results in determining that the patient has prostate cancer that is not resistant to treatment by certain therapeutic agents, for example, a taxane, wherein the detection of AR-V7, such as by PCR or other detection methods, indicates that the patient is a candidate for other cancer treatment therapies, including but not limited to, chemotherapy, radiotherapy, immunotherapy or a therapeutic agent or pharmaceutical composition that alters expression of an androgen receptor variant polypeptide or polynucleotide (e.g., AR-V7) in the subject. In certain embodiments, the therapy comprises one or more experimental therapies, or one or more existing therapies, or a combination of experimental and existing therapies.

Disclosed herein are polypeptides that are homologous to androgen receptor variants described herein, including AR-V7. It is understood that as discussed herein the use of the terms homology and identity mean similarity. Thus, for example, if the use of the word homology is used between two non-natural sequences it is understood that this is not necessarily indicating an evolutionary relationship between these two sequences, but rather is looking at the similarity or relatedness between their peptide or nucleic acid sequences. Many of the methods for determining homology between two evolutionarily related molecules are routinely applied to any two or more nucleic acids or proteins for the purpose of measuring sequence similarity regardless of whether they are evolutionarily related or not. Thus, polypeptides disclosed herein comprise polypeptides of multiple species, including but not limited to mouse, human, chicken, pig, rat, cow, chimpanzee, zebrafish, etc.

Detection methods of the present disclosure include those that are known to those skilled in the art, such molecular detection assays including biological assays for detecting the presence of biomarkers such as androgen receptor variants, using techniques such as PCR, sequencing, microarrays (i.e. prefabricated chips), antibody assays (i.e. ELISA), high throughput protein arrays, Northern blots, Southern blots, Western blots. In some embodiments, the methods provided herein include the use of qRT-PCT for detecting mRNA in a sample.

Polypeptides disclosed herein encompass naturally occurring or synthetic molecule, and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide.

Disclosed herein are multimers of one or more polypeptides disclosed herein. In an aspect, a multimer comprises more than one of the monomers disclosed herein.

Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation.

Also, polypeptides disclosed herein can have one or more types of modifications. Numerous variants or derivatives of the peptides and analogs of the disclosure are also contemplated. As used herein, the term "analog" is used interchangeably with "variant" and "derivative." Variants and derivatives are well understood to those of skill in the art and can involve amino acid sequence modifications. Such amino acid sequence modifications typically fall into one or more of three classes: substitutional; insertional; or deletional variants. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Substitutions, deletions, insertions or any combination thereof may be combined to arrive at a final derivative or analog.

The polypeptides disclosed herein can comprise one or more substitutional variants, i.e., a polypeptide in which at least one residue has been removed and a different residue inserted in its place. Such substitutions generally are made in accordance with the table below and are referred to as conservative substitutions.

Exemplary Conservative Amino Acid Substitutions

| Original Residue | Exemplary Conservative Substitutions |
| --- | --- |
| Ala | Ser |
| Arg | Gly, Gln |
| Asn | Gln; His |
| Asp | Glu |
| Cys | Ser |
| Gln | Asn, Lys |
| Glu | Asp |
| Gly | Ala |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function are made by selecting substitutions that are less conservative than those shown in the above Table, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions that are generally expected to produce the greatest changes in the protein properties are those in which: (a) the hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or hystidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

Polypeptides may be produced by any method known in the art. One method of producing polypeptides is to link two or more amino acid residues, peptides or polypeptides together by protein chemistry techniques. For example, peptides or polypeptides are chemically synthesized using currently available laboratory equipment using either Fmoc (9-fluorenylmethyloxycarbonyl) or Boc (tert-butyloxycarbonoyl) chemistry. A peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively. Alternatively, the peptide or polypeptide is independently synthesized in vivo. Once isolated, these independent peptides or polypeptides may be linked to form a peptide or fragment thereof via similar peptide condensation reactions.

Those of skill in the art readily understand how to determine the sequence identity between two or more proteins or two or more nucleic acids. For example, the identity can be calculated after aligning the two sequences so that the identity is at its highest level. Another way of calculating identity can be performed by published algorithms. Optimal alignment of sequences for comparison may be conducted by the local homology algorithm of Smith et al., 1981, by the alignment algorithm of Needleman et al., 1970, by the search for similarity method of Pearson et a., 1988, by computerized implementations of these algorithms (GAP, BESTFIT, FASTA, and TFASTA in the Wisconsin Genetics Software Package, Genetics Computer Group, 575 Science Dr., Madison, Wis.), or by inspection.

Disclosed are methods and compositions including primers and probes, including labeled probes, which are capable of interacting with androgen receptor variant sequences, such as AR-V7 disclosed herein, including but not limited to SEQ ID NOS: 1-2. In additional embodiments, primers and probes, which are capable of interacting with androgen receptor variant sequences, such as AR-FL, are also provided, including but not limited to SEQ ID NOS: 3-4. In some instances, it is to be understood that a primer may be used as a probe, and that a probe may be used as a primer, depending on the reaction and the endpoint to be obtained. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR. It is understood that in certain embodiments, the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

The polynucleotides (primers or probes) can comprise the usual nucleotides consisting of a base moiety, a sugar moiety and a phosphate moiety, e.g., base moiety—adenin 9 yl (A), cytosin 1 yl (C), guanin 9 yl (G), uracil 1 yl (U), and thymin 1 yl (T); sugar moiety—ribose or deoxyribose, and phosphate moiety—pentavalent phosphate. They can also comprise a nucleotide analog, which contains some type of modification to either the base, sugar, or phosphate moieties. Modifications to nucleotides are well known in the art and would include for example, 5 methylcytosine (5 me C), 5 hydroxymethyl cytosine, xanthine, hypoxanthine, and 2 aminoadenine as well as modifications at the sugar or phosphate moieties. The polynucleotides can contain nucleotide substitutes which are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the target androgen receptor variant typically will be used to produce an amplified DNA product that contains a region of the target androgen receptor variant or the complete androgen receptor variant.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The nucleic acids, such as the oligonucleotides to be used as primers or probes, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein and nucleic acid molecules can be made using known methods such as those described by Nielsen et al., Bioconjug. Chem. 5:3-7(1994).

The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23)12997-302 (1997), incorporated herein by reference. Labeled probes are well-known in the art, and the present disclosure contemplates the use of labeled nucleic acids. Labels may include, but are not limited to, radiolabels, biotinylated labels, fluorophors, chemiluminescent labels, nanoparticles or other labels.

Further disclosed are chips, for example microarray chips, where at least one address is a sequence or part of a sequence set forth in any of the nucleic acid sequences disclosed herein. For example, the chip can contain a probe for AR-V7.

Therefore, provided herein is an array comprising a substrate having a plurality of addresses, wherein each address comprises a capture probe that specifically binds under stringent conditions a nucleic acid of AR-V7. A nucleic acid bound by the capture probe of each address is unique among the plurality of addresses.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from the nucleotide sequences of a plurality of markers, for example AR-V7. The substrate can be any substrate to which polynucleotide probes can be attached including, but not limited to, glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

Tissue samples can be treated to form single-stranded polynucleotides, for example, by heating or by chemical denaturation, as is known in the art and as described in the Examples. The single-stranded polynucleotides in the tissue sample can then be labeled and hybridized to polynucleotide probes on the array. Detectable labels which can be used include, but are not limited to, radiolabels, biotinylated labels, fluorophors, and chemiluminescent labels. Double stranded polynucleotides, comprising the labeled sample polynucleotides bound to polynucleotide probes, can be detected once the unbound portion of the sample is washed away. Detection can be visual or with computer assistance.

Disclosed herein are kits that are drawn to reagents that can be used in practicing methods disclosed herein. The kits can include any reagent or combination of reagents discussed herein or that would be understood to be required or beneficial in the practice of the disclosed methods. For example, the kits could include primers to perform the amplification reactions described, as well as the buffers and enzymes required to use the primers as intended. For example, disclosed is a kit for assessing a drug resistance, comprising a nucleic acid of AR-V7. The kit can include instructions for using the reagents described in the methods disclosed herein.

Disclosed herein are methods for detecting the presence of androgen receptor variants such as AR-V7 in bodily fluid samples from prostate cancer patients wherein the samples comprise circulating tumor cells from patients with castration-resistant prostate cancer, comprising detecting in a sample from a prostate cancer patients AR-V7.

In a surprising discovery, disclosed herein are methods comprising detection of AR-V7 in prostate cancer patients, and associating the presence or amount of AR-V7 with resistance to certain drugs such as enzalutamide and abiraterone, or to the lack of resistance to certain therapeutic agents, such a taxane.

It is contemplated that a person of skill in the art using the disclosed compositions and methods can detect AR-V7 in a sample from a subject and thus identify the subject as having an increased likelihood of drug resistance to enzalutamide and abiraterone, or that a subject does not have an increased likelihood of drug resistance, for example, to a taxane.

For example, a tissue sample from a prostate cancer patient can be tested to determine whether AR-V7 is present or is present in a certain amount. In certain embodiments, the tissue sample comprises a bodily fluid sample, such as a sample comprising circulating tumor cells. In certain embodiments, the prostate cancer patient has castration-resistant prostate cancer. As used herein, subject and patient may be used interchangeably.

Disclosed herein are methods and compositions for detecting AR-V7 in a sample from a subject and thus identify the subject as having an increased likelihood of drug resistance to enzalutamide and abiraterone comprising using a monoclonal antibody to determine the levels of AR-V7 in a sample, subject, or patient. In an aspect, a monoclonal antibody binds to AR-V7.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with an androgen receptor variant such as AR-V7.

In an aspect, an antibody binds to or interacts with a polypeptide that has a certain homology to AR-V7, such as a polypeptide that has 70, 75, 80, 85, 90, or 95 percent homology, or a percent in between 70-99 percent homology, to AR-V7. Specifically disclosed are antibodies that bind to or interact with peptide variants that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to AR-V7.

Disclosed antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (U.S. Pat. No. 4,816,567 and Morrison et al., 1984).

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. One of ordinary skill in the art knows how to make or produce monoclonal antibodies, which specifically bind to a polypeptide having a known amino acid sequence (e.g., Steplewski et al., 1985; Spira et al., 1984; WO 86/01533 (1986); U.S. Pat. No. 6,458,592). The monoclonal antibody, in some aspects, can be chimeric (e.g., U.S. Pat. No. 5,843,708), humanized (e.g., U.S. Pat. No. 6,423,511), primatized (e.g., U.S. Pat. No. 6,113,898), and/or linked to other polypeptides as fusion proteins. Portions of the monoclonal antibody can also be useful, either alone or linked to other proteins. These portions include, but are not limited to Fab (Fab')$_2$, Fv, etc. In an aspect, the monoclonal antibody can be linked to a carrier (e.g., water, buffered water, 0.4% saline, 0.3% glycine, and the like) or can be associated with an adjuvant (e.g., biliverdin, bilirubin, biotin, carnosine, chitin, etc.). Adjuvants have been used experimentally to promote a generalized increase in immunity against unknown antigens (e.g., U.S. Pat. No. 4,877,611).

Methods for humanizing non-human antibodies are well known in the art. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response. Humanized antibodies can be generated according to the methods of Winter and co-workers (Jones et al., 1986; Riechmann et al., 1988; Verhoeyen et al., 1988) by substituting rodent CDRs or CDR sequences for the corresponding sequences of a human antibody. Methods that can be used to produce humanized antibodies are also described in U.S. Pat. Nos. 4,816,567, 5,565,332, 5,721,367, 5,837,243, 5,939,598, 6,130,364, and 6,180,377. These methods can be used to generate, for example, a humanized antibody that binds to or interacts with AR-V7 or a portion thereof.

Disclosed herein are methods and compositions for determining effectiveness of prostate cancer treatment in a subject by determining the presence of, amount of, or change in, androgen receptor variants, such as AR-V7, during or after a course of treatment of the cancer, such as with an anti-cancer therapeutic and/or treatment with enzalutamide and abiraterone. The present disclosure comprises methods and compositions for determining effectiveness of castration-resistant prostate cancer treatment in a subject by determining the presence of, amount of, or change in, androgen receptor variants, such as AR-V7, during or after a course of treatment of the cancer, such as with a cancer treatment therapeutic and/or treatment with a taxane.

Disclosed methods and compositions can be used to determine a therapeutic regimen for a patient or subject having castration-resistant prostate cancer. Treatment as used herein can refer to various types of compositions, techniques, therapies, and devices that can be used to affect aberrant cell growth, tumor development, and cancer. For example, treatment can comprise a chemical, a pharmaceutical agent, or combinations thereof, which can be administered to a subject to treat aberrant cell growth, tumor development, and cancer. Treatment can comprise surgical intervention. Treatment can comprise therapy. Treatments can be delivered or exercised alone or can be delivered or exercised in combination with one or more other forms of treatment. Treatment can be repeatedly or continuously delivered. Such treatment can affect the subject's susceptibility for aberrant cell growth, tumor development, and cancer, or to partially or fully reverse the effects of aberrant cell growth, tumor development, and cancer.

Provided herein is a method of determining treatment of castration-resistant prostate cancer in a subject or a patient, comprising detecting the presence of AR-V7 in order to determine resistance to certain drugs, such as enzalutamide and abiraterone. Provided herein is a method of determining treatment of castration-resistant prostate cancer in a subject or a patient, comprising detecting the presence of AR-V7 in order to determine there is not resistance to certain drugs, such as taxane. The cancer of the disclosed methods can be any cell in a subject undergoing unregulated growth, invasion, or metastasis.

The term "subject" means any individual who is the target of administration. The subject can be a vertebrate, for example, a mammal. Thus, the subject can be a human. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. Subject includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

Disclosed herein are methods and compositions for assessing resistance to drugs such as enzalutamide and abiraterone in patients having castration-resistant prostate cancer. Additional therapeutic agents may also be assessed for potential therapeutic resistance in patients, including for example, the following lists of anti-cancer (anti-neoplastic) drugs: Antineoplastic: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor, carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocanycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor, interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator, protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor, stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur, tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Disclosed methods can further comprise assessment of drug resistance to one or more additional radiosensitizers. Examples of known radiosensitizers include gemcitabine, 5-fluorouracil, pentoxifylline, and vinorelbine.

The majority of chemotherapeutic drugs can be divided in to: alkylating agents, antimetabolites, anthracyclines, plant alkaloids, topoisomerase inhibitors, monoclonal antibodies, and other antitumor agents. All of these drugs affect cell division or DNA synthesis. Some newer agents do not directly interfere with DNA. These include the new tyrosine kinase inhibitor imatinib mesylate, which directly targets a molecular abnormality in certain types of cancer (chronic myelogenous leukemia, gastrointestinal stromal tumors). In addition, some drugs can be used which modulate tumor cell behaviour without directly attacking those cells. Hormone treatments fall into this category of adjuvant therapies.

Chemotherapeutic agents included within the scope of the disclosed methods can be alkylating agents. Alkylating agents are so named because of their ability to add alkyl groups to many electronegative groups under conditions present in cells. Cisplatin and carboplatin, as well as oxaliplatin are alkylating agents. Other agents are mechloethamine, cyclophosphamide, chlorambucil. They work by chemically modifying a cell's DNA.

Chemotherapeutic agents included within the scope of the disclosed methods can be anti-metabolites. Anti-metabolites masquerade as purine (azathioprine, mercaptopurine) or pyrimidine—which become the building blocks of DNA. They prevent these substances becoming incorporated in to DNA during the 'S' phase (of the cell cycle), stopping normal development and division. They also affect RNA synthesis. Due to their efficiency, these drugs are the most widely used cytostatics.

Chemotherapeutic agents included within the scope of the disclosed methods can be plant alkaloids or terpenoids. These alkaloids are derived from plants and block cell division by preventing microtubule function. Microtubules are vital for cell division and without them it cannot occur. The main examples are *vinca* alkaloids and taxanes.

Chemotherapeutic agents included within the scope of the disclosed methods can be *vinca* alkaloid. *Vinca* alkaloids bind to specific sites on tubulin, inhibiting the assembly of tubulin into microtubules (M phase of the cell cycle). They are derived from the Madagascar periwinkle, *Catharanthus roseus* (formerly known as *Vinca rosea*). The *vinca* alkaloids include: Vincristine, Vinblastine, Vinorelbine, Vindesine, and Podophyllotoxin. Podophyllotoxin is a plant-derived compound used to produce two other cytostatic drugs, etoposide and teniposide. They prevent the cell from entering the GI phase (the start of DNA replication) and the replication of DNA (the S phase). The exact mechanism of its action still has to be elucidated. The substance has been primarily obtained from the American Mayapple (*Podophyllum peltatum*). A rare Himalayan Mayapple (*Podophyllum*

*hexandrum*) contains it in a much greater quantity, but as the plant is endangered, its supply is limited. Studies have been conducted to isolate the genes involved in the substance's production, so that it could be obtained recombinantly.

Chemotherapeutic agents included within the scope of the disclosed methods can be taxanes. The prototype taxane is the natural product paclitaxel, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

Chemotherapeutic agents included within the scope of the disclosed methods include topoisomerase inhibitors. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include the camptothecins irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Chemotherapeutic agents included within the scope of the disclosed methods can be antitumor antibiotics (Antineoplastics).

Chemotherapeutic agents included within the scope of the disclosed methods can be (monoclonal) antibodies. Monoclonal antibodies work by targeting tumor specific antigens, thus enhancing the host's immune response to tumor cells to which the agent attaches itself. Examples are trastuzumab (Herceptin), cetuximab, and rituximab (Rituxan or Mabthera). Bevacizumab is a monoclonal antibody that does not directly attack tumor cells but instead blocks the formation of new tumor vessels.

Hormonal therapy is included within the scope of the disclosed methods. Several malignancies respond to hormonal therapy. Strictly speaking, this is not chemotherapy. Cancer arising from certain tissues, including the mammary and prostate glands, may be inhibited or stimulated by appropriate changes in hormone balance. Steroids (often dexamethasone) can inhibit tumor growth or the associated edema (tissue swelling), and may cause regression of lymph node malignancies. Prostate cancer is often sensitive to finasteride, an agent that blocks the peripheral conversion of testosterone to dihydrotestosterone. Breast cancer cells often highly express the estrogen and/or progesterone receptor. Inhibiting the production (with aromatase inhibitors) or action (with tamoxifen) of these hormones can often be used as an adjunct to therapy. Gonadotropin-releasing hormone agonists (GnRH), such as goserelin possess a paradoxic negative feedback effect followed by inhibition of the release of FSH (follicle-stimulating hormone) and LH (luteinizing hormone), when given continuously. Some other tumors are also hormone dependent, although the specific mechanism is still unclear.

In general, when referring to treatment, the therapeutic compositions discussed herein may be administered orally, parenterally (e.g., intravenously or subcutaneous administration), by intramuscular injection, by intraperitoneal injection, transdermally, extracorporeally, by intracavity administration, transdermally, or topically or the like, including topical intranasal administration or administration by inhalant. The topical administration can be ophthalmically, vaginally, rectally, or intranasally. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

As used herein, "parenteral administration" of the composition, if used, is generally characterized by injection. Injectables can be prepared in conventional forms, either as liquid solutions or suspensions, solid forms suitable for solution of suspension in liquid prior to injection, or as emulsions. Parenteral administration includes use of a slow release, a time release or a sustained release system such that a constant dosage is maintained.

The term "therapeutically effective" means that the amount of the composition used is of sufficient quantity to ameliorate one or more causes or symptoms of a disease or disorder, such as aberrant cell growth, tumor development, and cancer. Such amelioration only requires a reduction or alteration, not necessarily elimination. Effective dosages and schedules for administering the disclosed compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products.

The specific effective amount of a therapeutic for any particular subject or patient will depend upon a variety of factors including the disease or disorder being treated and the severity of the disorder, the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts.

For example, it is well within the skill of the art to start doses of a composition at levels lower than those required to achieve the desired therapeutic effect and to gradually increase the dosage until the desired effect is achieved. One can also evaluate the particular aspects of the medical history, signs, symptoms, and objective laboratory tests that are known to be useful in evaluating the status of a subject in need of attention for the treatment of ischemia-reperfusion injury, trauma, drug/toxicant induced injury, neurodegenerative disease, cancer, or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular subject or patient: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

The effective amount of a prescribed therapeutic may be given daily, every other day, weekly, monthly, bi-monthly, every other monthly, yearly, or at any other interval that is determined by the physician or provider to be effective. For example, the effective daily dose can be divided into multiple doses for purposes of administration. Consequently, single dose therapeutic can contain such amounts or submultiples thereof to make up the daily dose. Disclosed therapeutics can also be administered as part of a combination of anti-tumor or anti-cancer treatments. In an aspect, disclosed compositions can be administered to the subject or patient prior to treatment with an anti-tumor or anti-cancer treatment. In an aspect, disclosed compositions can be administered concurrently with the anti-tumor or anti-cancer treatment. In an aspect, disclosed composition can be administered subsequent to the anti-tumor or anti-cancer treatment. In an aspect, the patient or subject receives both treatments on an alternating or rotating schedule. In an aspect, the subject or patient receives a singular treatment with the disclosed composition. In an aspect, the subject or patient receives at least one treatment with the disclosed composition. In an aspect, the subject or patient receives at least one treatment with the disclosed composition and at least one other anti-tumor or anti-cancer treatment.

The dosage can be adjusted by the individual physician or the subject in the event of any counter-indications. Dosage can vary, and can be administered in one or more dose administrations daily, for one or several days. Guidance can be found in the literature for appropriate dosages for given classes of pharmaceutical products.

Disclosed are methods and compositions for assays for determining AR-V7 levels. The disclosure comprises methods of screening for the presence of AR-V7 comprising utilizing hybridization assays, such as PCR using primers including but not limited to SEQ ID NOS: 1-2. In certain embodiments, PCR is used to determine the amount of AR-V7 compared to the amount of AR-FL, using for example, primers comprising SEQ ID NOS: 1-4.

The present disclosure comprises methods and compositions for determining AR-V7 levels in a cell, in an in vitro or in silico assay, in a subject, in a sample from a subject, or from other sources. A method comprises determining in a sample the AR-V7 levels by use of detection methods such as PCR.

It will be appreciated by those skilled in the art that the disclosed polypeptides and nucleic acids as well as the polypeptide and nucleic acid sequences identified from any subject or patient can be stored, recorded, and manipulated on any medium that can be read and accessed by a computer. The disclosed methods can be performed in silico. As used herein, the words "recorded" and "stored" refer to a process for storing information on a computer medium. A skilled artisan can readily adopt any of the presently known methods for recording information on a computer readable medium to generate a list of sequences comprising one or more of the nucleic acids of the disclosure. Another aspect of the present disclosure is a computer readable medium having recorded thereon at least 2, 5, 10, 15, 20, 25, 30, 50, 100, 200, 250, 300, 400, 500, 1000, 2000, 3000, 4000, 5000, 10,000, or more polypeptides or nucleic acids of the disclosure or polypeptide sequences or nucleic acid sequences identified from any subject or patient.

Thus, provided herein is a computer system comprising a database including records for AR-V7 and nucleic acids encoding AR-V7. Disclosed herein is a computer system comprising a database including records for polypeptides comprising variants of AR-V7 and nucleic acids comprising the sequences encoding variants of AR-V7. Computer readable medium include magnetically readable media, optically readable media, electronically readable media and magnetic/optical media. For example, the computer readable medium may be a hard disc, a floppy disc, a magnetic tape, CD-ROM, DVD, RAM, or ROM as well as other types of other media known to those skilled in the art.

Aspects of the present disclosure include systems, particularly computer systems which contain the sequence information described herein. As used herein, "a computer system" refers to the hardware components, software components, and data storage components used to store and/or analyze the nucleotide sequences of the present disclosure or other sequences. The computer system preferably includes the computer readable media described above, and a processor for accessing and manipulating the sequence data of the disclosed compositions including, but not limited to, the disclosed polypeptides and nucleic acids.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In an aspect, the computer system includes a processor connected to a bus which is connected to a main memory, preferably implemented as RAM, and one or more data storage devices, such as a hard drive and/or other computer readable media having data recorded thereon. In an aspect, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In an aspect, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the nucleotide sequences of the nucleic acids of the disclosure (such as search tools, compare tools, modeling tools, etc.) may reside in main memory during execution.

In an aspect, the computer system comprises a sequence comparer for comparing polypeptide and nucleic acid sequences stored on a computer readable medium to another test sequence stored on a computer readable medium. A "sequence comparer" refers to one or more programs that are implemented on the computer system to compare a nucleotide sequence with other nucleotide sequences and to compare a polypeptide with other polypeptides.

Accordingly, an aspect of the present disclosure is a computer system comprising a processor, a data storage device having stored thereon a polypeptide or nucleic acid of the disclosure, a data storage device having retrievably stored thereon reference polypeptide or nucleotide sequences to be compared with test or sample sequences and a sequence comparer for conducting the comparison. The sequence comparer may indicate a homology level between the sequences compared or identify a difference between two or more sequences. For example, a sample comprising AR-V7, or any fragment thereof can be compared with a test sequence from a subject or patient to determine if the test sequence is the same as the reference sequence.

The terminology used herein is for the purpose of describing particular aspects only and is not intended to be limiting.

As used in the specification and the appended claims, the singular forms "a," "an" and "the" can include plural referents unless the context clearly dictates otherwise. Thus, for example, reference to "a compound" includes mixtures of compounds reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, an aspect includes from the one particular value and/or to the other particular value. Similarly, when values are expressed as approximations, by use of the antecedent "about," it will be understood that the particular value forms an aspect. It will be further understood that the endpoints of each of the ranges are significant both in relation to the other endpoint, and independently of the other endpoint.

The amino acid abbreviations used herein are conventional one letter codes for the amino acids and are expressed as follows: Ala or A for Alanine; Arg or R for Arginine; Asn or N for Asparagine; Asp or D for Aspartic acid (Aspartate); Cys or C for Cysteine; Gln or Q for Glutamine; Glu or E for Glutamic acid (Glutamate); Gly or G for Glycine; His or H for Histidine; Ile or I for Isoleucine; Leu or L for Leucine; Lys or K for Lysine; Met or M for Methionine; Phe or F for Phenylalanine; Pro or P for Proline; Ser or S for Serine; Thr or T for Threonine; Trp or W for Tryptophan; Tyr or Y for Tyrosine; Val or V for Valine; Asx or B for Aspartic acid or Asparagine; and Glx or Z forGlutamine or Glutamic acid.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules. In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide.

As used herein, the term "amino acid sequence" refers to a list of abbreviations, letters, characters or words representing amino acid residues.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the disclosure can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "reverse analog" or "reverse sequence" refers to a peptide having the reverse amino acid sequence as another reference peptide. For example, if one peptide has the amino acid sequence ABCDE, its reverse analog or a peptide having its reverse sequence is as follows: EDCBA.

"Inhibit," "inhibiting," and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100 percent, or any amount of reduction in between as compared to native or control levels. In an aspect, the inhibition or reduction is 10-20, 20-30, 30-40, 40-50, 50-60, 60-70, 70-80, 80-90, or 90-100 percent as compared to native or control levels. In an aspect, the inhibition or reduction is 0-25, 25-50, 50-75, or 75-100 percent as compared to native or control levels.

"Modulate", "modulating" and "modulation" as used herein mean a change in activity or function or number. The change may be an increase or a decrease, an enhancement or an inhibition of the activity, function or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100 percent, or more, or any amount of promotion in between compared to native or control levels. In an aspect, the increase or promotion is 10-20, 20-30, 30-40, 40-50, 50-60, 60-70, 70-80, 80-90, or 90-100 percent as compared to native or control levels. In an aspect, the increase or promotion is 0-25, 25-50, 50-75, or 75-100 percent, or more, such as 200, 300, 500, or 1000 percent more as compared to native or control levels. In an aspect, the increase or promotion can be greater than 100 percent as compared to native or control levels, such as 100, 150, 200, 250, 300, 350, 400, 450, 500 percent or more as compared to the native or control levels.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

As used herein, the term "determining" can refer to measuring or ascertaining a quantity or an amount or a change in activity. For example, determining the amount of a disclosed polypeptide in a sample as used herein can refer to the steps that the skilled person would take to measure or ascertain some quantifiable value of the polypeptide in the sample. The art is familiar with the ways to measure an amount of the disclosed polypeptides and disclosed nucleotides in a sample.

The term "sample" can refer to a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid). A sample may also be any body fluid or excretion (for example, but not limited to, blood, urine, stool, saliva, tears, bile) that contains cells or cell components.

In an aspect, disclosed herein is a method of assessing resistance to a therapeutic agent in a subject diagnosed with prostate cancer comprising detecting the presence of AR-V7 in a bodily fluid of a subject diagnosed with prostate cancer; wherein the presence of AR-V7 indicates resistance to a therapeutic agent. In an aspect, the prostate cancer is castration-resistant prostate cancer. In an aspect, the bodily fluid is plasma, serum or peripheral blood. In an aspect, the plasma, serum or peripheral blood comprises circulating tumor cells. In an aspect, the presence of AR-V7 is determined by PCR. In an aspect, the therapeutic agent is enzalutamide. In an aspect, the therapeutic agent is abiraterone.

In an aspect, disclosed herein is a method of assessing whether a patient having castration-resistant prostate cancer is resistant to a therapeutic agent comprising detecting the presence of AR-V7 in a bodily fluid of a subject diagnosed with prostate cancer using PCR, wherein the bodily fluid comprises circulating tumor cells, and wherein detection of AR-V7 is an independent factor for indicating resistance to a therapeutic agent. In an aspect, the therapeutic agent is enzalutamide. In an aspect, the therapeutic agent is abiraterone.

In an aspect, disclosed herein is a method for determining a therapeutic regimen for a subject diagnosed with castration-resistant prostate cancer comprising detecting the presence of AR-V7 in a bodily fluid of a subject diagnosed with prostate cancer using PCR, wherein the bodily fluid comprises circulating tumor cells, wherein the detection of AR-V7 by PCR results in determining that the patient has prostate cancer that is resistant to treatment by certain therapeutic agents. In an aspect, detection of AR-V7 eliminates the use of enzalutamide as a therapeutic agent. In an aspect, detection of AR-V7 eliminates the use of abiraterones a therapeutic agent.

In an aspect, disclosed herein is a method of assessing response to a therapeutic agent in a subject diagnosed with prostate cancer comprising detecting the presence of AR-V7 in a bodily fluid of a subject diagnosed with prostate cancer, wherein the presence of AR-V7 indicates an efficacious response to a therapeutic agent. In an aspect, the therapeutic agent is a taxane.

In a method disclosed herein, in an aspect, the bodily fluid is collected at multiple time points following diagnosis of prostate cancer or during the course of treatment or at baseline, at a clinical/biochemical response, or at a clinical/radiographic progression. In an aspect, a clinical/biochemical response comprises measurement of prostate specific antigen. In an aspect, a clinical/radiographic progression comprises symptomatic progression, worsening disease-related symptoms, cancer-related complications, radiologic progression, enlargement in sum diameter of soft-tissue target lesions, increase in number of bone lesions, or death. In an aspect, the PCR assay comprises primers, wherein the primers may comprise one or more of SEQ ID NOs: 1 or 2. In an aspect, in one or more methods described above, a method may comprise measuring the amount of AR-FL, and comparing the amount of AR-V7 to the amount of AR-FL. In an aspect, measuring or detecting the presence of AR-FL comprises the use of one or more primers, wherein the primers may comprise one or more of SEQ ID NOS: 3 or 4.

In an aspect, disclosed herein is a method for determining a therapeutic regimen for a subject diagnosed with castration-resistant prostate cancer comprising, detecting the presence of AR-V7 in a bodily fluid of a subject diagnosed with prostate cancer using PCR, wherein the bodily fluid comprises circulating tumor cells, wherein the detection of AR-V7 by PCR results in determining that the patient has prostate cancer that is resistant to treatment by certain therapeutic agents, wherein the detection of AR-V7 by PCR results in determining that the patient is a candidate for alternative therapy.

In an aspect, the alternative therapy comprises experimental therapies, a combination of existing therapies or a combination of experimental and existing therapies.

In an aspect, disclosed herein is a method of assessing whether a patient having castration-resistant prostate cancer is resistant to a therapeutic agent comprising detecting the presence of AR-V7 in a bodily fluid of a subject diagnosed with prostate cancer using PCR, wherein the bodily fluid comprises circulating tumor cells, and wherein detection of AR-V7 is an independent factor for indicating resistance to a therapeutic agent. In an aspect, the therapeutic agent is enzalutamide. In an aspect, the therapeutic agent is abiraterone. In an aspect, the PCR assay comprises primers, wherein the primers may comprise one or more of SEQ ID NOs: 1 or 2. In an aspect, one or more methods described above further comprise measuring the amount of AR-FL, and comparing the amount of AR-V7 to the amount of AR-FL. In an aspect, measuring the amount of AR-FL comprises the use of one or more primers, wherein the primers may comprise one or more of SEQ ID NOs: 3 or 4.

In an aspect, disclosed herein is a method assessing the response to a therapeutic agent in a patient having castration resistant prostate cancer comprising detecting the presence of AR-V7 in a bodily fluid of a subject diagnosed with prostate cancer using PCR, wherein the bodily fluid comprises circulating tumor cells, and wherein detection of AR-V7 is an independent factor for indicating response to a therapeutic agent. In an aspect, the therapeutic agent is a taxane.

In an aspect, in methods described above, the bodily fluid from a patient is collected at multiple time points following diagnosis of prostate cancer or during the course of treatment or at baseline, at a clinical/biochemical response, or at a clinical/radiographic progression. In an aspect, the clinical/biochemical response comprises measurement of prostate specific antigen. In an aspect, the clinical/radiographic progression comprises symptomatic progression, worsening disease-related symptoms, cancer-related complications, radiologic progression, enlargement in sum diameter of soft-tissue target lesions, increase in number of bone lesions, or death.

In an aspect, disclosed herein is a method for determining a therapeutic regimen for a subject diagnosed with castration-resistant prostate cancer comprising, detecting the presence of AR-V7 in a bodily fluid of a subject diagnosed with prostate cancer using PCR, wherein the bodily fluid comprises circulating tumor cells, wherein the detection of AR-V7 by PCR results in a therapeutic regimen that includes or excludes one or more therapeutic agents. In an aspect, the detection of AR-V7 results in a therapeutic regimen that does not use enzalutamide, or does not use abiraterone or includes use of at least one taxane as a therapeutic agent. In an aspect, a bodily fluid from a patient is collected at multiple time points following diagnosis of prostate cancer or during the course of treatment or at baseline, at a clinical/biochemical response, and/or at a clinical/radiographic progression. In an aspect, a clinical/biochemical response comprises measurement of prostate specific antigen. In an aspect, a clinical/radiographic progression comprises symptomatic progression, worsening disease-related symptoms, cancer-related complications, radiologic progression, enlargement in sum diameter of soft-tissue target lesions, increase in number of bone lesions, or death. In an aspect, a PCR assay comprises primers, wherein the primers may comprise one or more of SEQ ID NOs: 1 or 2. In an aspect, methods described above further comprise measuring the amount of AR-FL, and comparing the amount of AR-V7 to the amount of AR-FL. In an aspect, the measuring or detecting the presence of AR-FL comprises the use of a primer, wherein a primer may comprise one or more of SEQ ID NOS: 3 or 4.

In an aspect, disclosed herein is a method for determining a therapeutic regimen for a subject diagnosed with castration-resistant prostate cancer comprising, detecting the presence of AR-V7 in a bodily fluid of a subject diagnosed with prostate cancer using PCR, wherein the bodily fluid comprises circulating tumor cells, wherein the detection of AR-V7 by PCR in results in a therapeutic regimen that includes alternative therapy. In an aspect, alternative therapy comprises experimental therapies, a combination of existing therapies or a combination of experimental and existing therapies.

Disclosed herein is a method comprising steps of determining level of an androgen receptor variant in a sample from a prostate cancer patient, wherein the sample is enriched for circulating tumor cells. In an aspect, the androgen receptor variant is or comprises AR-V7. In an aspect, the step of determining comprises examining a level of an AR-V7 transcript. In an aspect, the examining involves amplification with a polymerase chain reaction ("PCR"). In an aspect, the PCR is or comprises multiplex PCR that amplifies both full-length androgen receptor ("AR-FL") and AR-V7 transcripts. In an aspect, the PCR utilizes primers whose sequences are or comprise: SEQ ID NOS: 1-2 (AR-V7 (forward) 5'-CCATCTTGTCGTCTTCGGAAATGTTA-3' SEQ ID NO: 1; AR-V7 (reverse) 5'-TFGAAT- GAGGCAAGTCAGC-CTTCT-3' SEQ ID NO:2) and/or SEQ ID NOS: 3-4 (AR-FL (forward) 5'-CAGCCTAT-TGCGAGAGAGCTG-3' SEQ ID NO:3; AR-FL (reverse) 5'-GAAAGGATCTTGGGCACTTGC-3' SEQ ID NO:4). In an aspect, the PCR utilizes one or more primers that comprises a nucleotide analog or a nucleotide substitute. In an aspect, the patient is a castration-resistant prostate cancer patient ("CRPC"). In an aspect, the patient has been or is being treated with an AR signaling inhibitor. In an aspect, the patient is treated with a CYP17 inhibitor. In an aspect, the patient is a CRPC patient initiating treatment with an agent selected from the group consisting of abiraterone, enzalutamide, and combinations thereof or a CRPC patient resistant to an agent selected from the group consisting of abiraterone, enzalutamide, and combinations thereof. In an aspect, a sample is from a patient who has been or is being treated with an AR signaling inhibitor. In an aspect, a sample is from a patient who has been or is being is treated with a CYP17 inhibitor.

In an aspect, the method described herein, further comprises a step of repeating the determination on multiple samples, each of which was obtained at a different time point following diagnosis of prostate cancer. In an aspect, a plurality of the time points occurs during the course of treatment. In an aspect, at least one time point is a baseline time point, is at a moment of clinical or biochemical response or at a moment of clinical or radiographic progression. In an aspect, the clinical or biochemical response is or comprises measurement of prostate specific antigen. In an aspect, the clinical or radiographic progression involves monitoring symptomatic progression selected from the group consisting of worsening disease-related symptoms, cancer-related complications, radiologic progression, enlargement in sum diameter of soft-tissue target lesions, increase in number of bone lesions, death, and combinations thereof.

In an aspect, a method described herein, further comprises a step of administering an alternative therapy to therapy with abiraterone or enzalutamide when AR-V7 is detected. In an aspect, the alternative therapy comprises administration of an antineoplastic agent selected from the group consisting of Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur, Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor, carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereguline; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor, interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator, protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex;

rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer; and combinations thereof. In an aspect, the alternative therapy inhibits both AR-FL and ARVs. In an aspect, the alternative therapy is administered orally, parenterally, by intramuscular injection, by intraperitoneal injection, transdermally, extracorporeally, by intracavity administration, transdermally, or topically, including topical intranasal administration. In an aspect, the alternative therapy is for administration orally, parenterally, by intramuscular injection, by intraperitoneal injection, transdermally, extracorporeally, by intracavity, transdermally, or topically, including topical intranasal administration.

In an aspect, the alternative therapy comprises administration of an agent selected from the group consisting of alkylating agents, antimetabolites, anthracyclines, plant alkaloids, topoisomerase inhibitors, monoclonal antibodies, and combinations thereof. In an aspect, the alternative therapy comprises administration of an agent selected from the group consisting of terpenoids, *vinca* alkaloids, taxanes, antitumor antibiotics, In an aspect, the alternative therapy comprises administration of hormonal therapy.

In an aspect, as described herein, the step of determining comprises utilizing a hybridization assay. In an aspect, the hybridization assay is in situ hybridization of fresh or autopsy tumor samples. In an aspect, the step of determining comprises PCR to determine the amount of AR-V7 compared to the amount of AR-FL. In an aspect, the prostate cancer patient is receiving a course of treatment and the step of determining is repeated at a plurality of time points over the course of treatment. In an aspect, the AR-V7 is initially undetectably in a first determining step and is greater than or equal to 1 in at least one subsequent determining step performed at a later time point over the course of treatment. In an aspect, each determining step comprises determining the ratio of absolute copy number of AR-V7 to AR-FL.

In an aspect, one or more of the methods described herein is an in vitro method.

The disclosure will be further described with reference to the following examples; however, it is to be understood that the disclosure is not limited to such examples. Rather, in view of the present disclosure that describes the current best mode for practicing the disclosure, many modifications and variations would present themselves to those of skill in the art without departing from the scope and spirit of this disclosure. All changes, modifications, and variations coming within the meaning and range of equivalency of the claims are to be considered within their scope.

REFERENCES

1 Basch E, Loblaw D A, Oliver T K, et al: Systemic therapy in men with metastatic castration-resistant prostate cancer. American Society of Clinical Oncology and Cancer Care Ontario clinical practice guideline. J Clin Oncol 32: 3436-3448, 2014
2 de Bono J S, Logothetis C J, Molina A, et al: Abiraterone and increased survival in metastatic prostate cancer. N Engl J Med 364: 1995-2005, 2011
3 Scher H I, Fizazi K, Saad F, Taplin M E, et al: Increased survival with enzalutamide in prostate cancer after chemotherapy. N Engl J Med 367: 1187-1197, 2012
4 Tannock I F, de Wit R, Berry W R, et al: Docetaxel plus prednisone or mitoxantrone plus prednisone for advanced prostate cancer. N Engl J Med 351: 1502-1512, 2004
5 de Bono J S, Oudard S, Ozguroglu M, et al: Prednisone plus cabazitaxel or mitoxantrone for metastatic castration-resistant prostate cancer progressing after docetaxel treatment: a randomised open-label trial: Lancet 376: 1147-1154, 2010
6 Kantoff PW1, Higano C S, Shore N D, et al: Sipuleucel-T immunotherapy for castration-resistant prostate cancer. N Engl J Med 363: 411-422, 2010
7 Parker C, Nilsson S, Heinrich D, et al: Alpha emitter radium-223 and survival in metastatic prostate cancer. N Engl J Med 369: 213-223, 2013
8 Seruga B, Ocana A, Tannock I F. Drug resistance in metastatic castration-resistant prostate cancer. Nat Rev Clin Oncol 8: 12-23, 2011
9 Karantanos T, Evans C P, Tombal B, et al: Understanding the mechanisms of androgen deprivation resistance in prostate cancer at the molecular level. Eur Urol, epub ahead of print (doi: 10.1016/j.eururo.2014.09.049), 2014
10 Armstrong A J, Eisenberger M A, Halabi S, et al: Biomarkers in the management and treatment of men with metastatic castration-resistant prostate cancer. Eur Urol 61: 549-559, 2012
11 Antonarakis E S, Lu C, Wang H, et al: AR-V7 and resistance to enzalutamide and abiraterone in prostate cancer. N Engl J Med 371: 1028-1038, 2014
12 Dehm S M, Schmidt L J, Heemers H V, et al: Splicing of a novel androgen receptor exon generates a constitutively active androgen receptor that mediates prostate cancer therapy resistance. Cancer Res 68: 5469-5477, 2008
13 Hu R, Dunn T A, Wei S, et al: Ligand-independent androgen receptor variants derived from splicing of cryptic exons signify hormone-refractory prostate cancer. Cancer Res 69: 16-22, 2009
14 Hu R, Lu C, Mostaghel E A, et al: Distinct transcriptional programs mediated by the ligand-dependent full-length androgen receptor and its splice variants in castration-resistant prostate cancer. Cancer Res 72: 3457-3462, 2012
15 Mostaghel E A, Marck B T, Plymate S R, et al: Resistance to CYP17A1 inhibition with abiraterone in castration-resistant prostate cancer: induction of steroidogenesis and androgen receptor splice variants. Clin Cancer Res 17: 5913-5925, 2011

16 Li Y, Chan S C, Brand L J, Hwang T H, Silverstein K A, Dehm S M. Androgen receptor splice variants mediate enzalutamide resistance in castration-resistant prostate cancer cell lines. Cancer Res 73: 483-489, 2013

17 Gan L, Chen S, Wang Y, et al: Inhibition of the androgen receptor as a novel mechanism of taxol chemotherapy in prostate cancer. Cancer Res 69: 8386-8394, 2009

18 Zhu M L, Horbinski C M, Garzotto M, et al: Tubulin-targeting chemotherapy impairs androgen receptor activity in prostate cancer. Cancer Res 70: 7992-8002, 2010

19 Darshan M S, Loftus M S, Thadani-Mulero M, et al: Taxane-induced blockade to nuclear accumulation of the androgen receptor predicts clinical responses in metastatic prostate cancer. Cancer Res 71: 6019-6029, 2011

20 Thadani-Mulero M, Nanus D M, Giannakakou P: Androgen receptor on the move: boarding the microtubule expressway to the nucleus. Cancer Res 72: 4611-4615, 2012

21 Kirby B J, Jodari M, Loftus M S, et al: Functional characterization of circulating tumor cells with a prostate-cancer-specific microfluidic device. PLoS One 7: e35976, 2012

22 Thadani-Mulero M, Portella L, Sun S, et al: Androgen receptor splice variants determine taxane sensitivity in prostate cancer. Cancer Res 74: 2270-82, 2014

23 Scher H I, Halabi S, Tannock I, et al: Design and end points of clinical trials for patients with progressive prostate cancer and castrate levels of testosterone: recommendations of the Prostate Cancer Clinical Trials Working Group. J Clin Oncol 26: 1148-1159, 2008

24 Eisenhauer E A, Therasse P, Bogaerts J, et al: New response evaluation criteria in solid tumours: revised RECIST guideline (version 1.1). Eur J Cancer 45: 228-247, 2009

25 De Leeuw, R., Berman-Booty, L D, Schiewer M J, et al. Novel actions of next-generation taxanes benefit advanced stages of prostate cancer. Clin. Cancer Res. 2015; 21:795-807.

26 Plymate Sr, Bhatt R S, Balk S P. Taxane resistance in prostate cancer mediated by AR-dependent GATA2 regustion of IGF2. Cancer Cell, 2015; 27:158-159.

27 Van Soest R J, de Morree E S, Kweldam C F, et al. Targeting the androgen receptor confers in vivo cross-resistance between enzalutamide and docetaxel, but not cabazitaxel, in castration-resistant prostate cancer. Eur. Urol. 2014; epub ahead of print (10.1016/j.euro.2014.11.033).

EXAMPLES

Example 1

Correlation of Androgen Receptor Detection and Therapeutic Efficacy of Enzalutamide and Abiraterone 1. Experimental Methods a. Patients Men with metastatic CRPC who were beginning standard-of-care treatment with enzalutamide or abiraterone were prospectively enrolled. Patients were required to have histologically-confirmed prostate adenocarcinoma, progressive disease despite "castration levels" of serum testosterone (<50 ng/dL; and androgen-deprivation therapy had to continue), and radiographic metastases on computed tomography (CT) or technetium-99 bone scans. Patients had to have ≥3 rising serum prostate-specific antigen (PSA) values taken ≥2 weeks apart with the last value being ≥2.0 ng/mL, consistent with Prostate Cancer Working Group (PCWG2) guidelines (Scher, H. I., et al. (2008) *Journal of Clinical Oncology: Official Journal of the American Society of Clinical Oncology* 26, 1148-1159). Patients were excluded if they planned to receive additional concurrent anticancer therapies. Prior chemotherapy was permitted, as was previous treatment with the alternative AR-directed agent (i.e. prior abiraterone use in enzalutamide-treated patients, and vice versa). This study was approved by the Johns Hopkins University IRB, and was conducted according to Good Clinical Practice guidelines. Patients provided written informed consent.

b. Study Design and Assessments

This was a prospective study evaluating the ability of baseline (pretreatment) AR-V7 status from CTCs (circulating tumor cells) to predict response or resistance to AR-directed agents. Patients who were about to begin standard-of-care enzalutamide or abiraterone were consented and then asked to donate peripheral-blood CTC samples at up to 3 time-points: one at baseline, one at the time of a clinical/biochemical response (if a response occurred), and one at the time of clinical/radiographic progression. In addition, patients were encouraged to undergo metastatic core-tumor biopsies at baseline and at progression. Enzalutamide was given at 160 mg daily, and abiraterone was given at 1000 mg daily (with prednisone 5 mg twice-daily).

Follow-up was prospectively defined: patients had PSA measurements every 1-2 months, as well as CT (chest/abdomen/pelvis) and technetium-99 bone scans every 2-4 months. Therapy with enzalutamide or abiraterone was continued until PSA-progression or clinical/radiographic-progression, or unmanageable drug-related toxicity.

c. CTC Analysis

CTC analyses were conducted using the commercially-available ALERE™ CTC AdnaTest platform (AdnaGen, Langenhagen, Germany). Isolation and enrichment of CTCs was performed using the ProstateCancerSelect kit, and mRNA expression analyses were performed using the ProstateCancerDetect kit with multiplexed reverse-transcription polymerase-chain-reaction (qRT-PCR) primers to detect the presence of CTCs, and custom primers designed to detect the full-length-AR (AR-FL) and AR splice variant-7 (AR-V7) (Hu, R., et al. (2009) *Cancer Res* 69, 16-22). Relative AR-V7 transcript abundance was determined by calculating the ratio of AR-V7 to AR-FL (Hu, R., et al. (2009) *Cancer Res* 69, 16-22; Watson, P. A., et al. (2010) *Proceedings of the National Academy of Sciences*).

d. Clinical Outcomes

The primary endpoint was the proportion of patients who achieved a PSA response (≥50% PSA decline from baseline, maintained for ≥4 weeks) at any time-point post-therapy, and was assessed separately for enzalutamide-treated and abiraterone-treated patients. Best PSA response (maximal percentage PSA decrease from baseline) for each patient was also determined.

Secondary endpoints included freedom-from-PSA-progression (PSA-progression-free-survival; PSA-PFS), freedom-from-clinical/radiographic-progression (progression-free-survival; PFS), and overall survival (OS). PSA-progression was defined as a ≥25% increase in PSA from nadir (and by ≥2 ng/mL), requiring confirmation ≥4 weeks later (PCWG2 criteria) (Scher, H. I., et al. (2008) *Journal of Clinical Oncology: Official Journal of the American Society of Clinical Oncology* 26, 1148-1159). Clinical/radiographic-progression was defined as symptomatic progression (worsening disease-related symptoms or new cancer-related complications), or radiologic progression (on CT scan: ≥20% enlargement in sum diameter of soft-tissue target lesions

[RECIST criteria (Therasse, P., et al. (2000) *Journal of the National Cancer Institute* 92, 205-216)]; on bone scan: ≥2 new bone lesions), or death, whichever occurred first (Scher, H. I., et al. (2008) *Journal of Clinical Oncology: Oficial Journal of the American Society of Clinical Oncology* 26, 1148-1159). OS was defined as the time to death from any cause.

e. Tumor Tissue Analysis

To investigate concordance in AR-V7 status between CTCs and tumor tissue, qRT-PCR analysis for AR-V7 was performed on fresh metastatic tumor biopsies (or autopsy specimens) from a subset of patients who consented to this. In addition, RNA in situ hybridization (RNA-ISH) was performed according to the manufacturer's instructions using the RNAscope platform (AdvancedCell Diagnostics, Hayward, Calif.) to visualize AR-V7 mRNA in formalin-fixed paraffin-embedded metastatic tumor tissues, and to correlate this with AR-V7 detection in CTCs.

f. Analysis of Circulating Tumor Cells

Blood samples were collected using standard BD Vacutainer® lavender top blood collection tubes (Becton Dickinson, Franklin Lakes, N.J.) (Product #: 367862) by venipuncture, and carried to the lab on ice. Laboratory processing was carried out within 2 hours of collection, according to instructions provided by the Alere™ CTC AdnaTest (Alere Inc., San Diego, Calif.). The AdnaTest is a CE-marked, RNA-based CTC enrichment and detection test with two components/kits. Briefly, the ProstateCancerSelect (Product No. T-1-520) kit was used to enrich CTC from 5 mL blood using magnetic particles coated with a combination of antibodies recognizing prostate cancer cells, while the ProstateCancerDetect (Product No. T-1-521) kit was used to make cDNA for detection of prostate cancer-associated RNA transcripts using multiplexed polymerase chain reaction (PCR). On the basis of detection of PCR signals for PSA, PSMA, or EGFR (very rarely detected) by the Agilent Bioanalyzer (Agilent Technologies, Palo Alto, Calif.), CTC calls were made for each sample tested. The test was adapted for detection and quantification of AR-FL and AR-V7 by quantitative real-time PCR using custom primers specific for AR-FL (forward: 5'-CAGCCTATTGCGAGAGAGCTG-3' SEQ ID NO:1, reverse: 5'-GAAAGGATCTTGGGCACTTGC-3' SEQ ID NO:2) and AR-V7 (forward: 5'-CCATCTTGTCGTCTTCG-GAAATGTTA-3' SEQ ID NO:3) (reverse: 5'-TIGAAT-GAGGCAAGTCAGC-CTTTCT-3' SEQ ID NO:4). Briefly, PCR reactions were carried out under optimized conditions at 95° C.×10 s, 58° C.×30 s, and 72° C.×30 s for 39 cycles followed by melting curve analysis. Standard dilution curves from known quantities of AR-FL and AR-V7 was generated for calculating absolute transcript copy numbers for AR-FL and AR-V7. Laboratory data was generated for each patient enrolled in the study in a blinded fashion and recorded into the master data sheet on a weekly basis. To rule out false positive and false negative findings, a number of quality control measures were implemented each time the assay was performed, including negative and positive controls at multiple levels for both CTC detection and AR quantification.

g. RNA In Situ Hybridization

RNA in situ hybridization (RISH) was performed to detect the androgen receptor (AR) and AR-V7 using the ACD (Advanced cell Diagnostics, Hayward, Calif.) RNAscope 2.0 Brown kit. Briefly, formalin-fixed paraffin-embedded (FFPE) tissue or cell pellet blocks were sectioned and the slides baked for one hour at 60° C. The slide were subsequently de-paraffinized with xylene for 20 min at room temperature, and allowed to air dry following two rinses using 100% ethanol. Following a series of pretreatment steps, the cells were permeablized using protease to allow probe access to the RNA target. ACD target probes, a series of paired oligonucleotides forming a binding site for a preamplifier, were custom designed to detect RNA corresponding to exon 1 of the human AR (ACD 401211), or the cryptic AR exon 3 sequence (Hu, R., et al. (2009) *Cancer Res* 69, 16-22; Hu, R., et al. (2011) *The Prostate* 71, 1656-1667) that encode human AR-V7 (ACD 401221). Hybridization of the probes to the AR RNA targets was performed by incubation in the oven for 2 hours at 40° C. Following two washes, the slides were processed for standard signal amplification steps per manufacturer's instructions.

h. Western Blot

Whole cell protein extracts were prepared from cultured prostate cancer cells or cryosections prepared from clinical specimens by using RIPA buffer (radioimmunoprecipitation assay buffer) (Cell Signaling Technology, Danvers, Mass.) supplemented with IX protease inhibitors (Roche, Indianapolis, Ind.) and 1× phosphatase inhibitors (Thermo Fisher Scientific, Rockford, Ill.). Standard blots were prepared following electrophoresis of forty µg protein per sample on a 10% SDS-PAGE precast gel (Bio-Rad Laboratories, Hercules, Calif.), and incubated overnight with anti-AR-V7 (Hu, R., et al. (2012) *Cancer Res* 72, 3457-3462) (1 µg/mL), anti-AR (N20) (1:2000 dilution) (sc-816, Santa Cruz Biotechnology, Dallas, Tex.), anti-PSA (C-19) (1:500) (sc-7638, Santa Cruz Biotechnology), and anti-β-actin (1:5000 dilution) (Sigma, St Louis, Mo.). Following incubation with horseradish-peroxidase (HRP)-conjugated secondary antibodies, immunoreactive bands were visualized using the SuperSignal West Pico Chemiluminescent Substrate system (1-34080) (Thermo Fisher Scientific, Rockford, Ill.) on HyBlot CL film (E3022) (Denville Scientific, South Plainfield, N.J.).

i. Prostate Cancer Cell Lines

LNCaP cells (ATCC, Manassas, Va.) were maintained in RPMI1640 medium (Invitrogen, Carlsbad, Calif.) with 10% fetal bovine serum (FBS, Sigma-Aldrich, St. Louis, Mo.). LNCaP95 is an AR-V7-positive androgen-independent cell line derived from the parental LNCaP cells as described previously (Hu, R., et al. (2012) *Cancer Res* 72, 3457-3462). LNCaP95 cells were maintained in phenol red-free RPMI 1640 medium supplemented with 10% charcoal stripped FBS (CSS). For analysis of androgen-induced changes in AR-V7, LNCaP95 cells were treated with R1881 (NEN, Waltham, Mass.) or ethanol vehicle control as described previously (Hu, R., et al. (2012) *Cancer Res* 72, 3457-3462). These cell lines were authenticated (DDC Medical, Fairfield, Ohio) using short tandem repeats DNA profiling and tested negative for *mycoplasma*.

j. Metastatic Prostate Tumor Tissue Specimens

Research autopsies were performed on two patients who died during the course of treatment with enzalutamide. Both patients were AR-V7 positive as determined by the CTC assay before and after treatment. Metastatic prostate tumors were dissected and flash frozen blocks prepared. Following histological analysis, cryosections enriched for tumor cells were prepared following manual trimming of the frozen blocks, using a standard procedure as described previously (Luo, J., et al. (2001) *Cancer Res* 61, 4683-4688). High-quality total RNA in adequate quantity was extracted from two specimens (one from each patient) and labeled as AR-V7(+) Met1 and AR-V7(+) Met2, respectively. To identify relevant AR-V7-negative metastatic CRPC samples for comparison, AR-FL and AR-V7 expression levels were analyzed in a separate collection of CRPC specimens from men consented for autopsy (before the development of enzalutamide and abiraterone) as described previously (Hu, R., et al. (2009) *Cancer Res* 69, 16-22; Aryee, M. J., et al. (2013) *Science translational medicine* 5, 169ra10; Liu, W., et al. (2009) *Nature medicine* 15, 559-565). Two specimens that were AR-V7 negative but with AR-FL levels similar to those detected in other mCRPC specimens were identified from this collection of specimens. These two samples were labeled AR-V7(−) Met1 and AR-V7(−) Met2. Both samples were processed histologically in a similar fashion to enrich prostate carcinoma cells.

k. RNA-Seq

Four metastatic prostate tissue specimens, AR-V7(+) Met1, AR-V7(+) Met2, AR-V7(−) Met1, and AR-V7(−) Met 2, were subjected to RNA-Seq following the standard TruSeq Stranded Total RNA Sample Prep Kit and sequenced using the Illumina HiSeq 2000 platform (Illumina Inc, San Diego, Calif.). An average of ~63 million reads per sample were generated. Sequences were aligned to UCSC hg19 genome build using TopHat, and mutation and splice junctions visualized using Integrated Genome Viewer (IGV) (Robinson, J. T., et al. (2011) *Nature biotechnology* 29, 24-26). Read counts (gene expression levels) were obtained using HTSeq (Anders, S., et al. (2014) HTSeq-A Python framework to work with high-throughput sequencing data. bioRxiv), and normalized perkilo base-pair gene length and per million reads library size (RPKM). Fold expression changes (FC) between the two conditions (AR-V7(+) and AR-V7(−)) were calculated. Genes were pre-ranked by log FC and subjected to Gene Set Enrichment Analysis (GSEA) (Subramanian, A., et al. (2005) *Proceedings of the National Academy of Sciences of the United States of America* 102: 15545-15550). Both raw and processed RNA-Seq data were deposited in the Gene Expression Omnibus (accession number: GSE56701).

l. Statistical Analysis

Statistical analyses were performed separately in the enzalutamide and abiraterone cohorts. Sample size was determined based on the primary endpoint of PSA response. It was assumed that AR-V7 would be detectable from baseline CTC samples in 50% of enzalutamide-treated and 50% of abiraterone-treated patients. In both cohorts, it was hypothesized that PSA response rates would be ≤10% in AR-V7-positive patients and ≥60% in AR-V7-negative patients (Scher, H. I., et al. (2012) *New England Journal of Medicine* 367, 1187-1197; Ryan, C. J., et al. (2013) *New England Journal of Medicine* 368, 138-148). Under this assumption, a sample size of 30 patients (per cohort) would yield 85% power to detect a difference in PSA response rates from 10% (in AR-V7-positive men) to 60% (in AR-V7-negative men), using a two-sided test with $\alpha=0.10$.

In each cohort, clinical outcomes were compared between AR-V7-positive and AR-V7-negative patients. PSA response rates were compared using Fisher's exact test. Time-to-event outcomes (e.g. PSA-PFS, PFS, and OS) were evaluated using Kaplan-Meier analysis, and survival-time differences were compared using the log-rank test. Univariate and multivariable Cox regressions were used to assess the effect of AR-V7 status in predicting time-to-event outcomes. Due to the small sample size and limited number of events, each multivariable model included only 3 variables (AR-V7 status, AR-FL expression levels, and prior use of the alternative AR-directed therapy), to prevent over-fitting. Propensity score weighted multivariable Cox analyses were also performed for PSA-PFS and PFS, where the propensity score (probability of being AR-V7-positive) was calculated from logistic regression using variables including Gleason score, baseline PSA, number of prior hormonal treatments, presence of visceral metastases, ECOG score, prior abiraterone/enzalutamide use, and AR-FL levels. All tests were two-sided, and P-values ≤0.05 were considered significant. Statistical analyses were performed using software R (version 2.15.1).

The principal clinical investigator was blinded to AR-V7 data. The principal laboratory investigator was blinded to clinical information when determining AR-V7 status. The primary statistician was the first person to unblind the data, after ≥30 patients had been enrolled per cohort.

2. AR-V7 Detection in CTCs

First, the detection of AR-V7 transcript from normal human blood spiked with VCaP cells was demonstrated (FIG. 1A), a prostate cancer cell line known to express both AR-FL and AR-V7 (Hu, R., et al. (2009) *Cancer Res* 69, 16-22). Patient samples were then assayed; examples of positive and negative detection of AR-V7 in blood samples from two patients are shown (FIG. 1B). After establishing the validity of the assay (not shown), AR-V7 positivity was defined as detection of the AR-V7 transcript by qRT-PCR at ≤36 PCR cycles, corresponding to detection of ≥1 copy of AR-V7 cDNA as determined by the relationship between cycle number and serial dilutions of pre-quantified AR-V7 (FIGS. 2A and 2B).

Figure 1A:
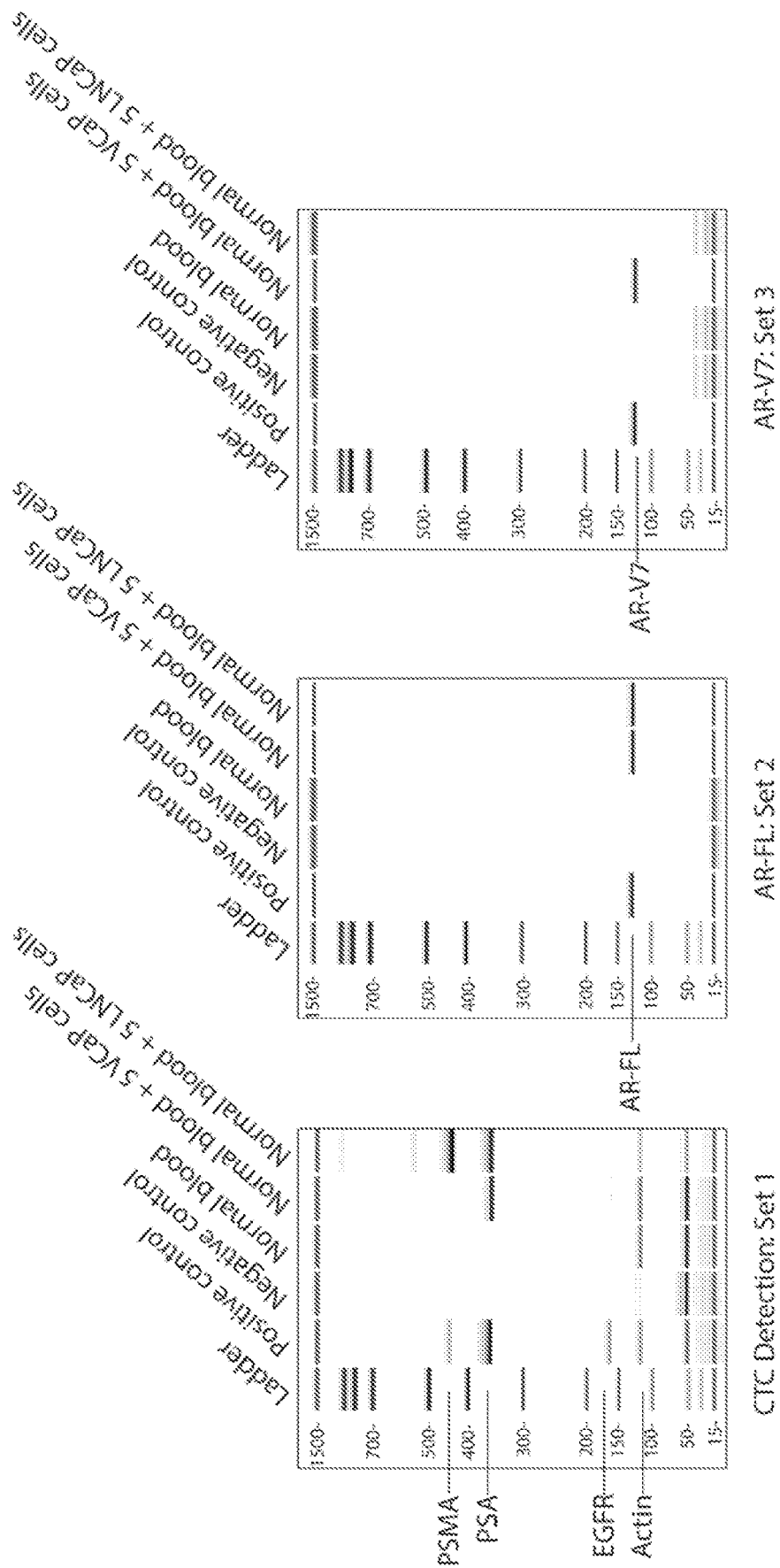
FIGS. 1A and 1B show representative data pertaining to the detection of AR-V7 transcript in CTCs. (A) Blood-based detection of full-length androgen receptor (AR-FL) and AR splice variant-7 (AR-V7) transcripts in tumor cells spiked into 5 mL of blood from normal human volunteers. Following CTC capture, lysis, and cDNA synthesis, three sets of independent PCR reactions were performed to examine the presence of CTC-specific mRNA transcripts by multiplex PCR (set 1), as well as transcripts for AR-FL (set 2) and AR-V7 (set 3). (B) Examples of positive and negative detection of AR-V7 in baseline (pre-treatment) blood samples from two enzalutamide-treated patients. The patient in the left panel is positive for both AR-FL and AR-V7, while the patient in the right panel is positive only for AR-FL but negative for AR-V7. Both patients were positive for CTCs, as determined by the multiplex PCR assay (based on the examination of PSMA, PSA, EGFR and Actin) per the manufacturer's instructions provided by AdnaGen.
Figure 1B:
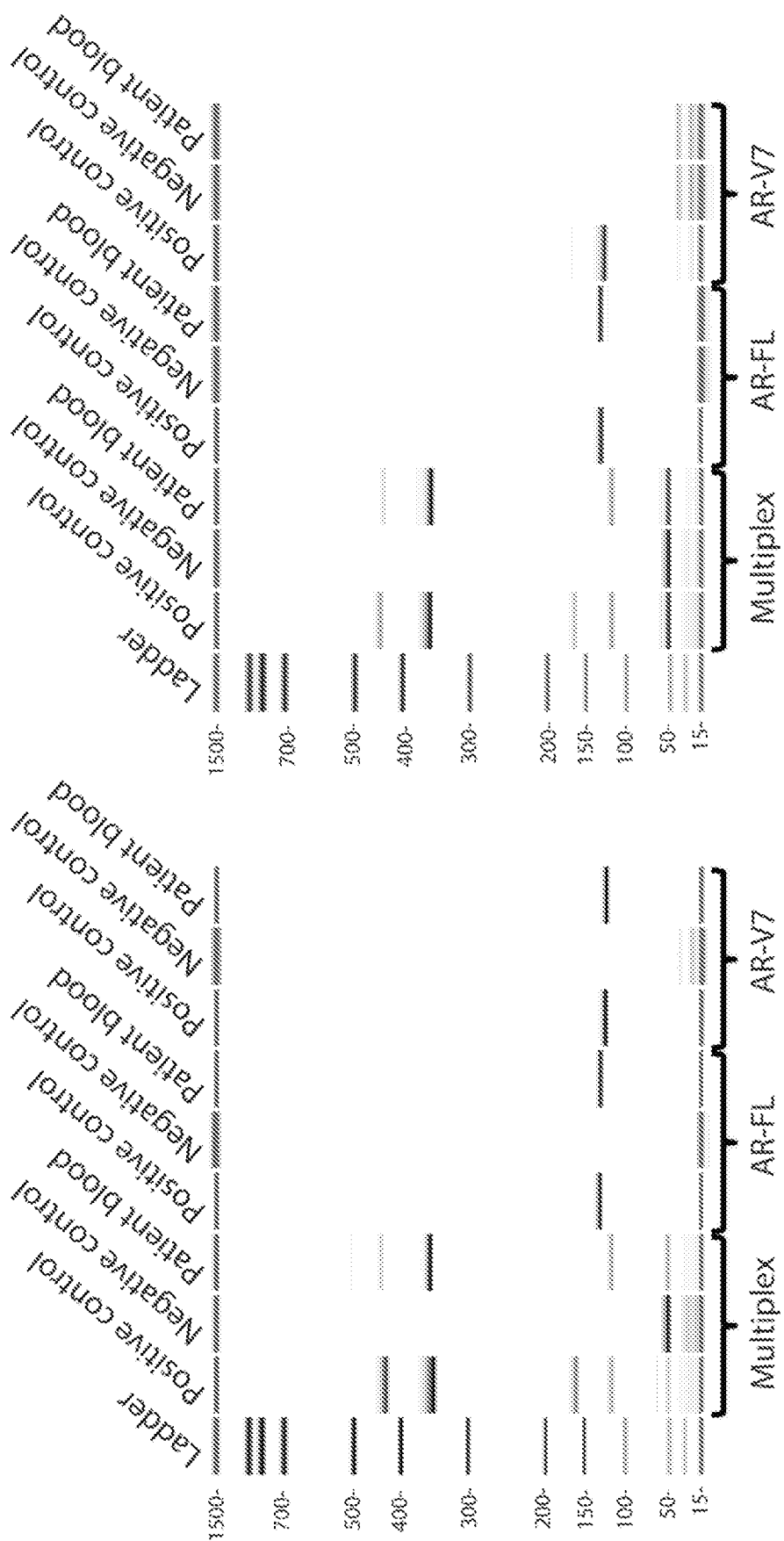

Referring to FIG. 1A, blood-based detection of full-length androgen receptor (AR-FL) and AR splice variant-7 (AR-V7) transcripts is shown in tumor cells spiked into 5 mL of blood from normal human volunteers. Following CTC capture, lysis, and cDNA synthesis, three sets of independent PCR reactions were performed to examine the presence of CTC-specific mRNA transcripts by multiplex PCR (set 1), as well as transcripts for AR-FL (set 2) and AR-V7 (set 3).

Referring to FIG. 1B, examples of positive and negative detection of AR-V7 in baseline (pre-treatment) blood samples from two enzalutamide-treated patients are shown. The patient in the left panel is positive for both AR-FL and AR-V7, while the patient in the right panel is positive only for AR-FL but negative for AR-V7. Both patients were positive for CTCs, as determined by the multiplex PCR assay (based on the examination of PSMA, PSA, EGFR and Actin) per the manufacturer's instructions provided by AdnaGen.

Figure 2A:
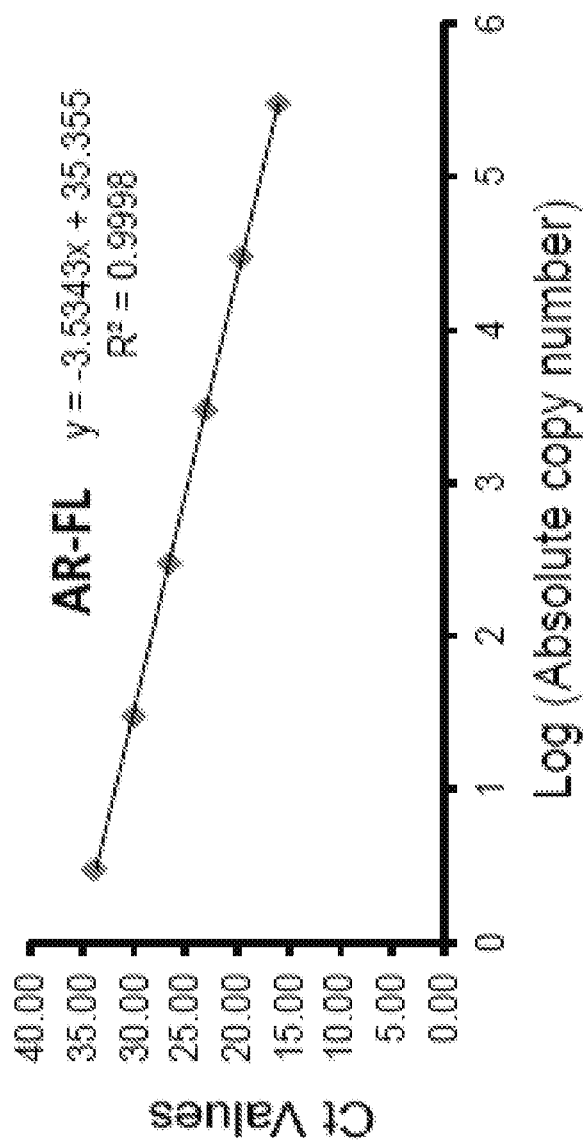
FIGS. 2A and 2B show representative data pertaining to the justification for threshold of detection of AR-V7.
Figure 2B:
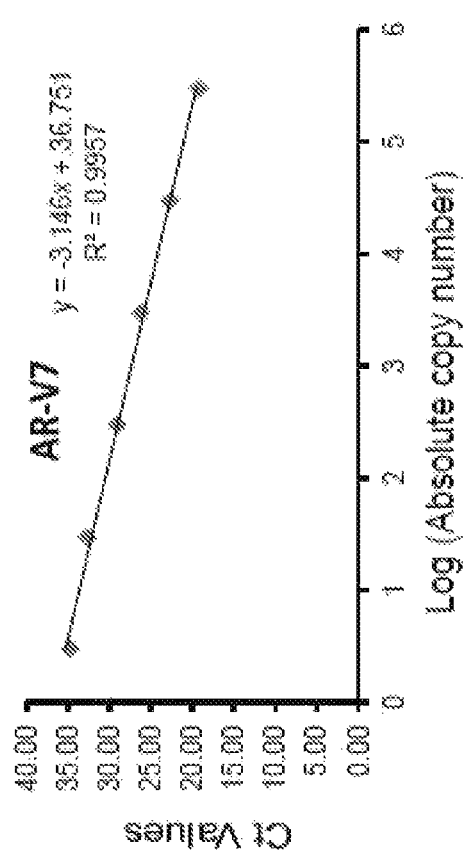

Referring to FIGS. 2A and 2B, standard dilution curves for AR-FL and AR-V7 are shown. Threshold cycle numbers (Y axis) in quantitative PCR reactions were determined for complementary DNA (cDNA) specific to AR-FL (2A) and AR-V7 (2B) at 6 dilutions containing the indicated number of copies of each transcript (X axis). Formulas were derived to quantify the absolute copy numbers on the basis of Ct values.

3. Patient Characteristics

Figure 3A:
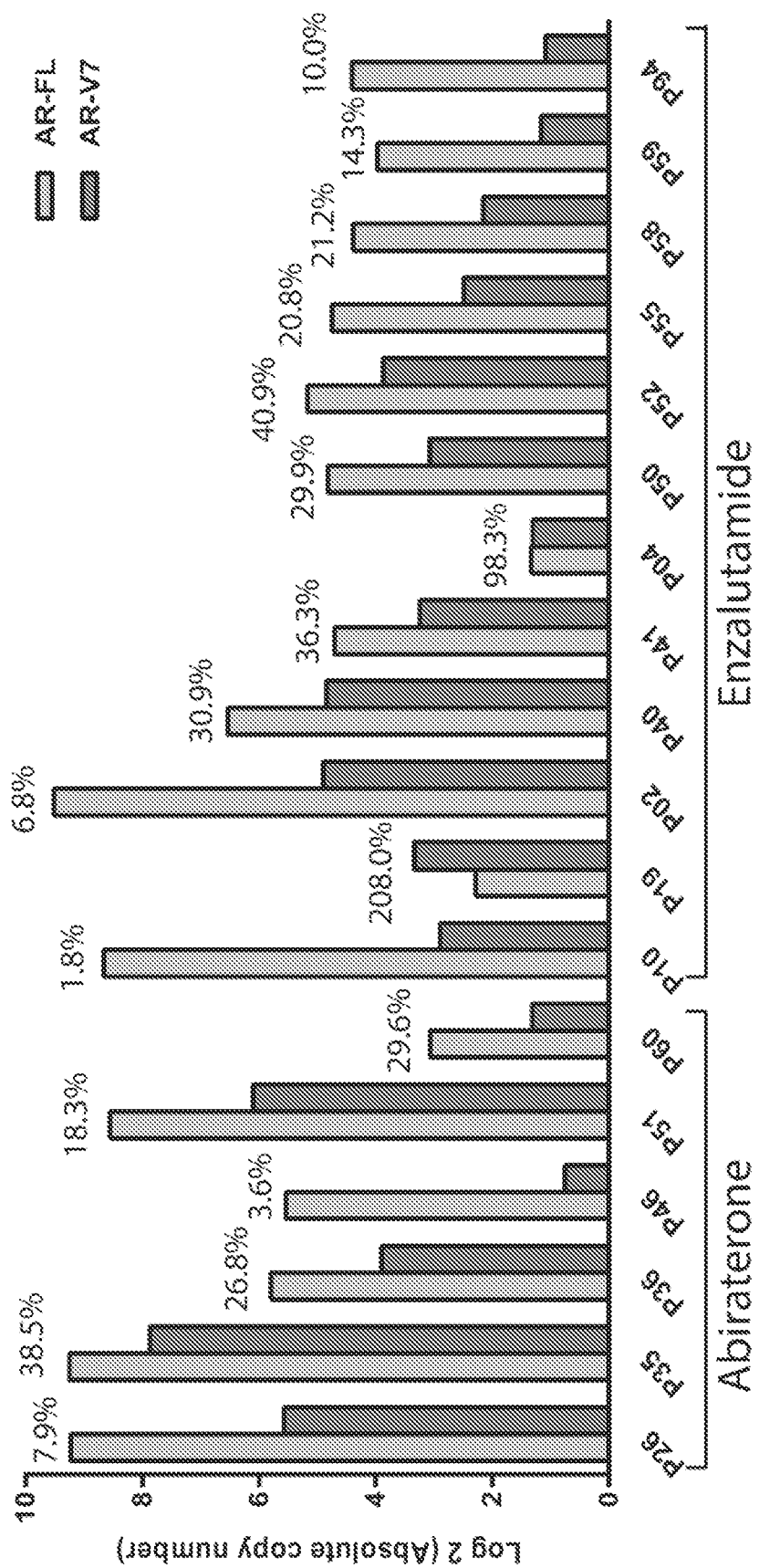
FIGS. 3A-C show representative data pertaining to the quantification of AR-FL and AR-V7 transcript levels in CTCs from CRPC patients initiating treatment with abiraterone and enzalutamide. (A) Absolute transcript copy numbers of AR-FL and AR-V7 detected in circulating tumor cells (CTCs) from the 18 patients who were positive for AR-V7 at baseline (i.e. in pretreatment CTC samples). Ratios of AR-V7:AR-FL are expressed as percentages, and these range from 1.8% to 208.0%. (B) Quantification of AR-FL and AR-V7 transcript levels in abiraterone-treated patients. AR-FL levels are shown for both AR-V7-positive and AR-V7-negative samples. Patients that were negative for AR-FL (n=8; not shown) were also negative for AR-V7. (C) Quantification of AR-FL and AR-V7 transcript levels in enzalutamide-treated patients. AR-FL levels are shown for both AR-V7-positive and AR-V7-negative samples. One patient was negative for both AR-FL and AR-V7 (not shown).

Between December 2012 and September 2013, 62 patients were prospectively enrolled, of which 31 received enzalutamide (Table 1) and 31 received abiraterone (Table 2). Median follow-up among enzalutamide-treated patients was 5.4 (range, 1.4-9.9) months, and in abiraterone-treated patients was 4.6 (range, 0.9-8.2) months. 38.7% of enzalutamide-treated patients (12/31) and 19.4% of abiraterone-treated patients (6/31) had detectable AR-V7 mRNA in baseline CTC samples. In men with detectable AR-V7 (n=18) from the entire study cohort, the median AR-V7: AR-FL ratio was 21.0% (range, 1.8-208.0%) (FIG. 3A); AR-V7 detection was associated with increased expression of AR-FL (P<0.001) (FIGS. 3B and 3C).

Referring to FIG. 3A, the absolute transcript copy numbers of AR-FL and AR-V7 detected in circulating tumor cells (CTCs) from the 18 patients who were positive for AR-V7 at baseline (i.e., in pretreatment CTC samples) are shown. Ratios of AR-V7:AR-FL are expressed as percentages, and these range from 1.8% to 208.0%.

Figure 3B:
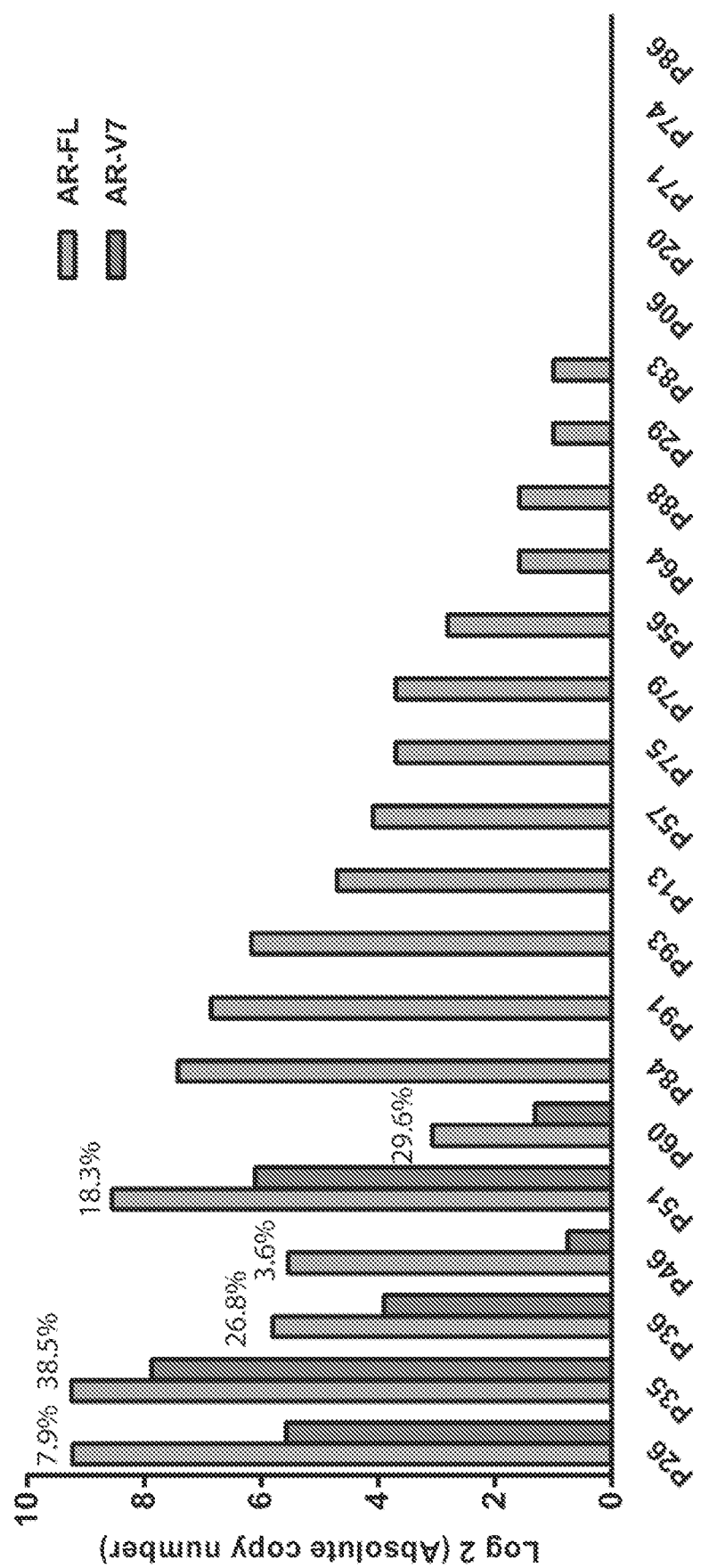

Referring to FIG. 3B, the quantification of AR-FL and AR-V7 transcript levels in abiraterone-treated patients is shown. AR-FL levels are shown for both AR-V7-positive and AR-V7-negative samples. Patients that were negative for AR-FL (n=8; not shown) were also negative for AR-V7. (C) Quantification of AR-FL and AR-V7 transcript levels in enzalutamide-treated patients.

Figure 3C:
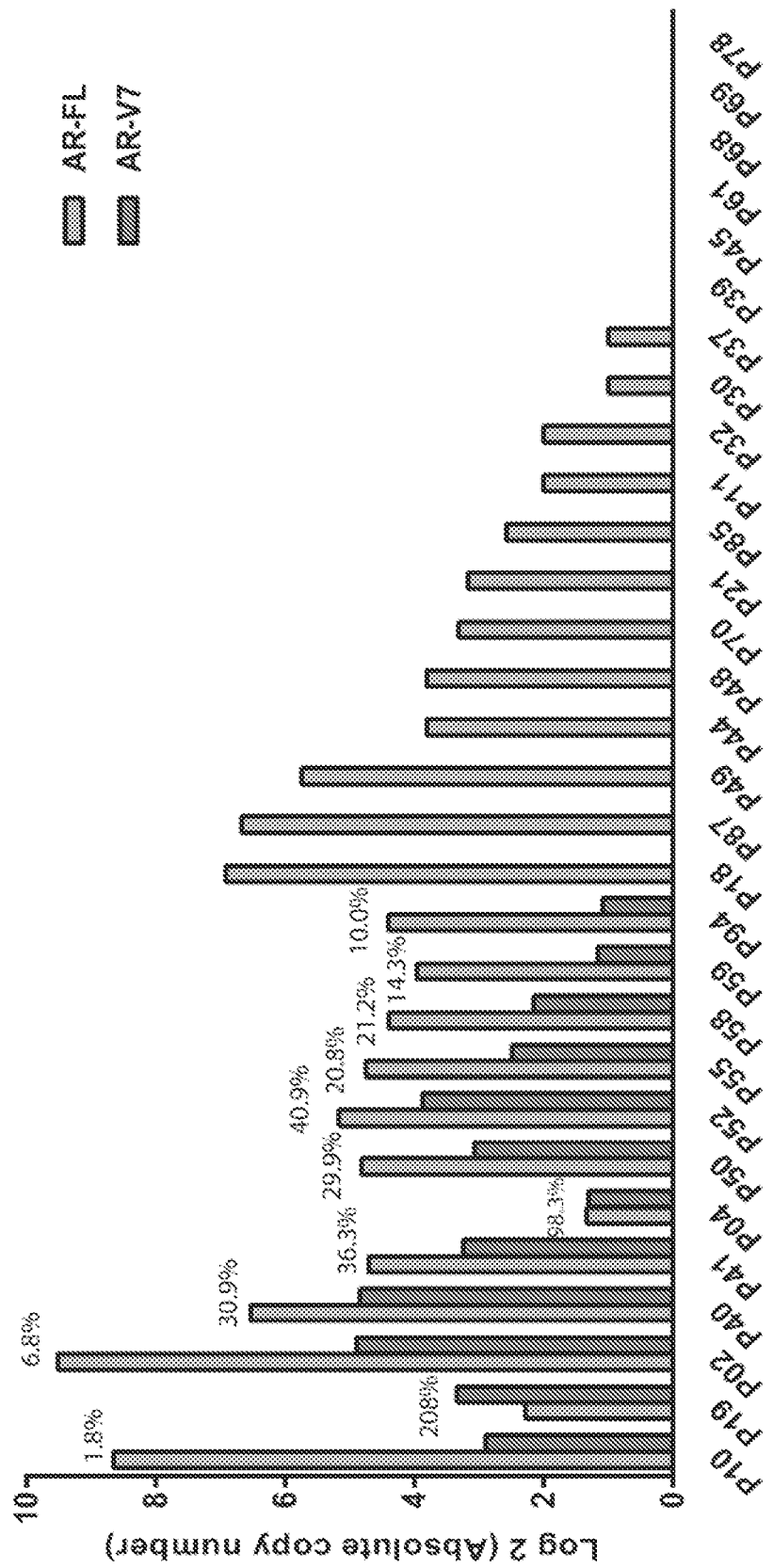

Referring to FIG. 3C, AR-FL levels are shown for both AR-V7-positive and AR-V7-negative samples. One patient was negative for both AR-FL and AR-V7 (not shown).

TABLE 1

| Baseline Characteristic | All Patients (N = 31) | AR-V7 Negative (N = 19) | AR-V7 Positive (N = 12) | P-value* |
|---|---|---|---|---|
| Age (years) | | | | |
| Median (range) | 70 (56-84) | 72 (60-84) | 69 (56-82) | 0.223 |
| Race, N (%) | | | | |
| White | 26 (83.9%) | 16 (84.2%) | 10 (83.3%) | |
| Non-white | 5 (16.1%) | 3 (15.8%) | 2 (16.7%) | 0.999 |
| Time since diagnosis (years) | | | | |
| Median (range) | 5 (1-21) | 5 (1-21) | 7 (1-18) | 0.760 |
| Tumor stage at diagnosis, N (%) | | | | |
| T1/T2 | 17 (54.8%) | 10 (52.6%) | 7 (58.3%) | |
| T3/T4 | 14 (45.2%) | 9 (47.4%) | 5 (41.7%) | 0.999 |
| Gleason sum at diagnosis, N (%) | | | | |
| ≤7 | 12 (40.0%) | 9 (47.4%) | 3 (27.3%) | |
| ≤8 | 18 (60.0%) | 10 (52.6%) | 8 (72.7%) | 0.442 |
| Type of local treatment, N (%) | | | | |
| Surgery | 13 (41.9%) | 8 (42.1%) | 5 (41.7%) | |
| Radiation | 7 (22.6%) | 6 (31.6%) | 1 (8.3%) | |
| None | 11 (35.5%) | 5 (26.3%) | 6 (50.0%) | 0.262 |
| Number of prior hormonal therapies | | | | |
| Mean (range) | 3.3 (2-5) | 3.2 (2-5) | 3.4 (3-5) | 0.317 |
| Prior use of abiraterone, N (%) | | | | |
| Yes | 20 (64.5%) | 9 (47.4%) | 11 (91.7%) | |
| No | 11 (35.5%) | 10 (52.6%) | 1 (8.3%) | 0.020 |
| Prior use of docetaxel, N (%) | | | | |
| Yes | 20 (64.5%) | 10 (52.6%) | 10 (83.3%) | |
| No | 11 (35.5%) | 9 (47.4%) | 2 (16.7%) | 0.128 |
| Presence of bone metastases, N (%) | | | | |
| Yes | 28 (90.3%) | 17 (89.5%) | 11 (91.7%) | |
| No | 3 (9.7%) | 2 (10.5%) | 1 (8.3%) | 0.999 |
| Number of bone metastases, N (%) | | | | |
| Yes | 20 (64.5%) | 15 (78.9%) | 5 (41.7%) | |
| No | 11 (35.5%) | 4 (21.1%) | 7 (58.3%) | 0.056 |
| Presence of visceral metastases, N (%) | | | | |
| Yes | 10 (32.3%) | 3 (15.8%) | 7 (58.3%) | |
| No | 21 (67.7%) | 16 (84.2%) | 5 (41.7%) | 0.021 |
| ECOG performance status score, N (%) | | | | |
| 0 | 22 (71.0%) | 16 (84.2%) | 6 (50.0%) | |
| 1 or 2 | 9 (29.0%) | 3 (15.8%) | 6 (50.0%) | 0.056 |
| Baseline PSA (ng/mL) | | | | |
| Median (range) | 44.3 (4.3-3204.2) | 29.8 (4.3-452.0) | 144.3 (14.5-3204.2) | 0.282 |
| Baseline alkaline | | | | |

TABLE 1-continued

| Baseline Characteristic | All Patients (N = 31) | AR-V7 Negative (N = 19) | AR-V7 Positive (N = 12) | P-value* |
|---|---|---|---|---|
| phosphatase (U/L) | | | | |
| Median (range) | 108 (58-872) | 91 (58-872) | 110 (82-744) | 0.282 |
| Baseline AR-FL level (copy number) | | | | |
| Median (range) | 10 (0-734) | 4 (0-121) | 26 (3-734) | 0.003 |

*P-value is based on Fisher's Exact test and Wilcoxon Mann-Whitney test for categorical and continuous variables, respectively.

TABLE 2

| Baseline Characteristic | All Patients (N = 31) | AR-V7 Negative (N = 25) | AR-V7 Positive (N = 6) | P-value* |
|---|---|---|---|---|
| Age (years) | | | | |
| Median (range) | 69 (48-79) | 69 (48-79) | 69 (58-79) | 0.565 |
| Race, N (%) | | | | |
| White | 25 (80.6%) | 20 (80.0%) | 5 (83.3%) | |
| Non-white | 6 (19.4%) | 5 (20.0%) | 1 (16.7%) | 0.999 |
| Time since diagnosis (years) | | | | |
| Median (range) | 5 (1-21) | 5 (1-13) | 4 (1-21) | 0.705 |
| Tumor stage at diagnosis, N (%) | | | | |
| T1/T2 | 12 (38.7%) | 10 (40.0%) | 2 (33.3%) | |
| T3/T4 | 19 (61.3%) | 15 (60.0%) | 4 (66.7%) | 0.999 |
| Gleason sum at diagnosis, N (%) | | | | |
| ≤7 | 8 (26.7%) | 6 (24.0%) | 2 (40.0%) | |
| ≤8 | 22 (73.3%) | 19 (76.0%) | 3 (60.0%) | 0.589 |
| Type of local treatment, N (%) | | | | |
| Surgery | 14 (45.2%) | 10 (40.0%) | 4 (66.6%) | |
| Radiation | 10 (32.3%) | 9 (36.0%) | 1 (16.7%) | |
| None | 7 (22.6%) | 6 (24.0%) | 1 (16.7%) | 0.520 |
| Number of prior hormonal therapies | | | | |
| Mean (range) | 2.5 (2-6) | 2.2 (2-4) | 3.7 (2-6) | 0.020 |
| Prior use of enzalutamide, N (%) | | | | |
| Yes | 4 (12.9%) | 2 (8.0%) | 2 (33.3%) | |
| No | 27 (87.1%) | 23 (92.0%) | 4 (66.7%) | 0.159 |
| Prior use of docetaxel, N (%) | | | | |
| Yes | 5 (16.1%) | 4 (16.0%) | 1 (16.7%) | |
| No | 26 (83.9%) | 21 (84.0%) | 5 (83.3%) | 0.999 |
| Presence of bone metastases, N (%) | | | | |
| Yes | 24 (77.4%) | 19 (76.0%) | 5 (83.3%) | |
| No | 7 (22.6%) | 6 (24.0%) | 1 (16.7%) | 0.999 |
| Number of bone metastases, N (%) | | | | |
| Yes | 17 (54.8%) | 15 (60.0%) | 2 (33.3%) | |
| No | 14 (45.2%) | 10 (40.4%) | 4 (66.7%) | 0.370 |
| Presence of visceral metastases, N (%) | | | | |
| Yes | 8 (25.8%) | 8 (32.0%) | 0 (0%) | |
| No | 23 (74.2%) | 17 (68.0%) | 6 (100%) | 0.298 |

TABLE 2-continued

| Baseline Characteristic | All Patients (N = 31) | AR-V7 Negative (N = 25) | AR-V7 Positive (N = 6) | P-value* |
|---|---|---|---|---|
| ECOG performance status score, N (%) | | | | |
| 0 | 25 (80.6%) | 22 (88.0%) | 3 (50.0%) | |
| 1 or 2 | 6 (19.4%) | 3 (12.0%) | 3 (50.0%) | 0.069 |
| Baseline PSA (ng/mL) | | | | |
| Median (range) | 37.8 (2.2-2045.0) | 31.4 (2.2-262.2) | 86.9 (19.4-2045.0) | 0.084 |
| Baseline alkaline phosphatase (U/L) | | | | |
| Median (range) | 118 (59-1348) | 109 (59-524) | 263 (71-1348) | 0.063 |
| Baseline AR-FL level (copy number) | | | | |
| Median (range) | 3 (0-609) | 1 (0-173) | 216 (8-609) | 0.002 |

*P-value is based on Fisher's Exact test and Wilcoxon Mann-Whitney test for categorical and continuous variables, respectively.

In the enzalutamide cohort, AR-V7-positive patients were more likely to have higher AR-FL levels, higher PSA levels, ECOG performance status ≥1, visceral metastases, ≥6 bone metastases, prior docetaxel treatment, and prior abiraterone treatment (Table 2). Among patients previously receiving abiraterone, 55% (11/20) had detectable AR-V7 compared to 9% (1/11) in abiraterone-naïve men. Table 3 reports clinical outcomes separately for abiraterone-pretreated and abiraterone-naïve patients.

TABLE 3

| | No previous abiraterone (n = 11) | | | Previous abiraterone (n = 20) | | |
|---|---|---|---|---|---|---|
| Outcome | AR-V7 [+] (n = 1) | AR-V7 [−] (n = 10) | P value | AR-V7 [+] (n = 11) | AR-V7 [−] (n = 9) | P value |
| PSA Response | 0% (0/1) | 80% (8/10) | 0.273 | 0% (0/11) | 22% (2/9) | 0.189 |
| PFA-PFS | HR (95% CI) not estimable | | 0.005 | HR 3.34 (95% CI, 1.14-9.80) | | 0.0121 |
| PFS | HR (95% CI) not estimable | | 0.005 | HR 2.93 (95% CI, 0.96-8.90) | | 0.048 |

In the abiraterone cohort, AR-V7-positive patients were more likely to have higher AR-FL levels, higher PSA levels, higher alkaline phosphatase levels, ECOG status ≥1, more prior hormonal therapies, and prior enzalutamide treatment (Table 2). Among patients previously receiving enzalutamide, 50% (2/4) had detectable AR-V7 compared to 14.8% (4/27) in enzalutamide-naïve men. Table 4 reports clinical outcomes separately for enzalutamide-pretreated and enzalutamide-naïve patients, while Table 5 reports clinical outcomes according to prior exposure to abiraterone/enzalutamide.

TABLE 4

| | No previous enzalutamide (n = 27) | | | Previous enzalutamide (n = 4) | | |
|---|---|---|---|---|---|---|
| Outcome | AR-V7 [+] (n = 4) | AR-V7 [−] (n = 23) | P value | AR-V7 [+] (n = 2) | AR-V7 [−] (n = 2) | P value |
| PSA Response | 0% (0/4) | 74% (17/23) | 0.012 | 0% (0/2) | 0% (0/2) | N/A |
| PFA-PFS | HR 41.0 (95% CI, 4.5-376.8) | | <0.001 | HR (95% CI) not estimable | | N/A |
| PFS | HR 28.2 (95% CI, 3.1-255.8) | | <0.001 | HR (95% CI) not estimable | | N/A |

TABLE 5

| | No prior abiraterone/ enzalutamide (n = 38) | | | Prior abiraterone/enzalutamide (n = 24) | | |
|---|---|---|---|---|---|---|
| Outcome | AR-V7 [+] (n = 5) | AR-V7 [−] (n = 33) | P value | AR-V7 [+] (n = 13) | AR-V7 [−] (n = 11) | P value |
| PSA Response | 0% (0/5) | 76% (25/33) | 0.003 | 0% (0/13) | 18% (2/11) | 0.199 |
| PFA-PFS | HR 55.9 (95% CI, 6.4-488.5) | | <0.001 | HR 2.91 (95% CI, 1.10-7.72) | | 0.023 |
| PFS | HR 45.2 (95% CI, 5.1-398.1) | | <0.001 | HR 2.65 (95% CI, 0.97-7.25) | | 0.048 |

4. Primary Endpoint

Figure 4A:
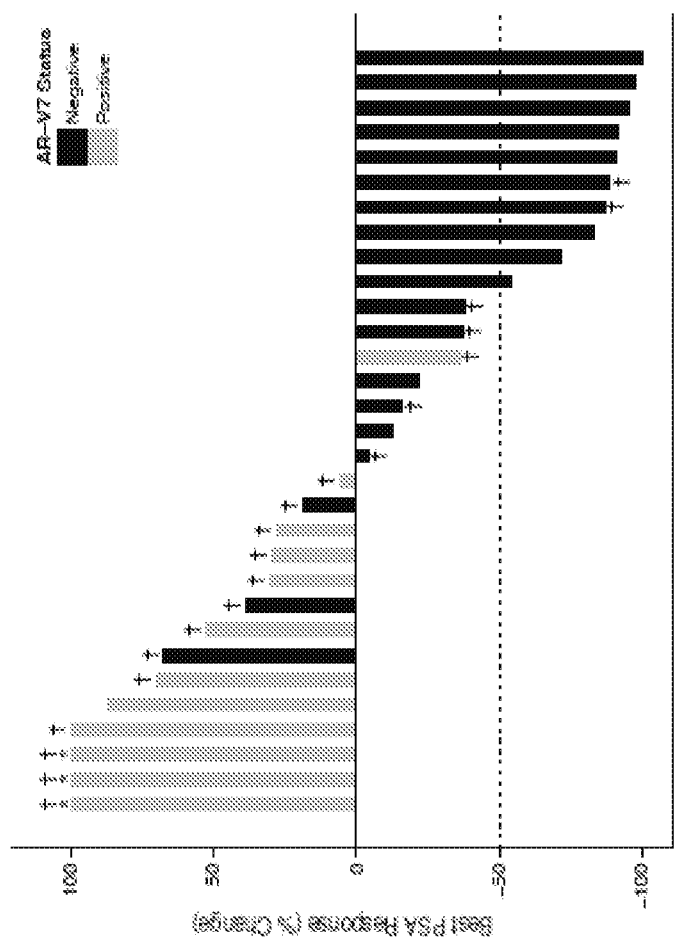
FIGS. 4A and 4B show representative waterfall plots depicting best PSA responses according to CTC AR-V7 status in 31 enzalutamide-treated patients (4A) and 31 abiraterone-treated patients (4B). The 'asterisk' marks (*) indicate clipped bars. The dotted line shows the threshold for defining a PSA response (≥50% PSA reduction from baseline). Patients in the enzalutamide cohort who had previously received abiraterone, and patients in the abiraterone cohort who had previously received enzalutamide, are denoted with 'dagger' marks (†) Among enzalutamide-treated patients (A) that achieved a PSA response, 0% (0/10 men; 95% CI, 0-31.2%) were AR-V7-positive; while in those patients without a PSA response, 57.1% (12/21 men; 95% CI, 34.3-78.1%) were AR-V7-positive. Among abiraterone-treated patients (B) that achieved a PSA response, 0% (0/17 men; 95% CI, 0-20.2%) were AR-V7-positive; while in patients without a PSA response, 42.9% (6/14 men; 95% CI, 18.3-71.2%) were AR-V7-positive.

The overall proportion of patients who achieved a PSA response on enzalutamide was 32.3% (10/31 men; 95% CI, 17.1-51.2%). Among enzalutamide-treated men, PSA response rates were 0% (0/12 men; 95% CI, 0-26.4%) in AR-V7-positive patients and 52.6% (10/19 men; 95% CI, 29.3-76.1%) in AR-V7-negative patients (P=0.004). Best PSA responses are depicted in FIG. 4A. In linear regression modeling, AR-V7 status remained predictive for PSA response after adjusting for AR-FL expression (P<0.001).

Referring to FIG. 4A, among enzalutamide-treated patients that achieved a PSA response, 0% (0/10 men; 95% CI, 0-31.2%) were AR-V7-positive; while in those patients without a PSA response, 57.1% (12/21 men; 95% CI, 34.3-78.1%) were AR-V7-positive. The 'asterisk' marks (*) indicate clipped bars. The dotted line shows the threshold for defining a PSA response (≥50% PSA reduction from baseline). Patients in the enzalutamide cohort who had previously received abiraterone are denoted with 'dagger' marks (†).

Figure 4B:
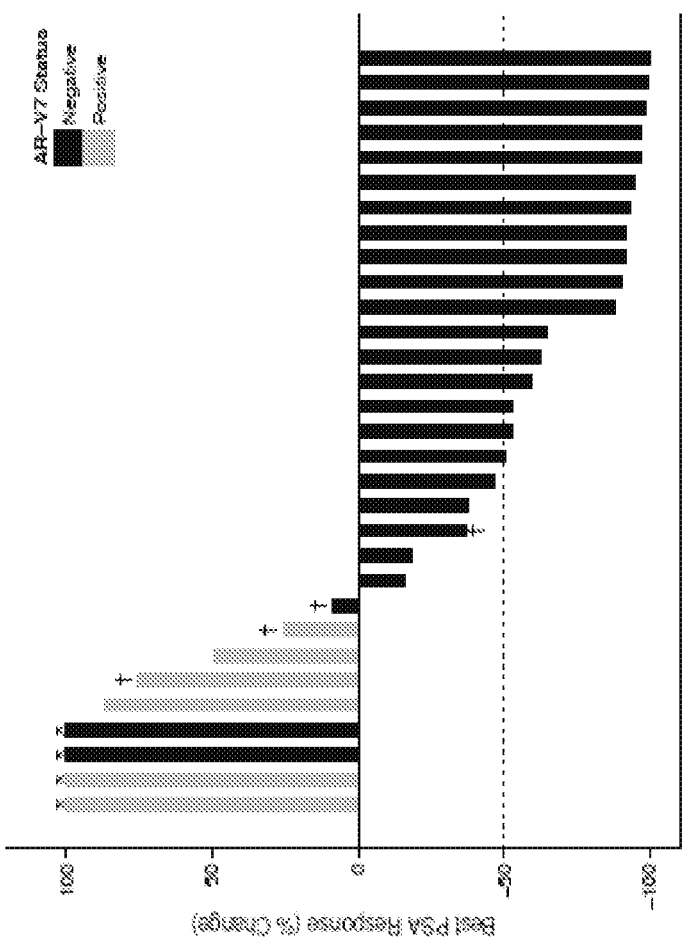

The overall proportion of patients who achieved a PSA response on abiraterone was 54.8% (17/31 men; 95% CI, 36.1-73.2%). Among abiraterone-treated men, PSA response rates were 0% (0/6 men; 95% CI, 0-46.4%) in AR-V7-positive patients and 68.0% (17/25 men; 95% CI, 46.3-85.1%) in AR-V7-negative patients (P=0.004). Best PSA responses are shown in FIG. 4B. Using linear regression, AR-V7 status remained predictive for PSA response after adjusting for AR-FL expression (P=0.018).

Referring to FIG. 4B, among abiraterone-treated patients (B) that achieved a PSA response, 0% (0/17 men; 95% CI, 0-20.2%) were AR-V7-positive; while in patients without a PSA response, 42.9% (6/14 men; 95% CI, 18.3-71.2%) were AR-V7-positive. The 'asterisk' marks (*) indicate clipped bars. The dotted line shows the threshold for defining a PSA response (≥50% PSA reduction from baseline). Patients in the abiraterone cohort who had previously received enzalutamide are denoted with 'dagger' marks (†).

5. Secondary Endpoints a. PSA-PFS

Figure 5B:
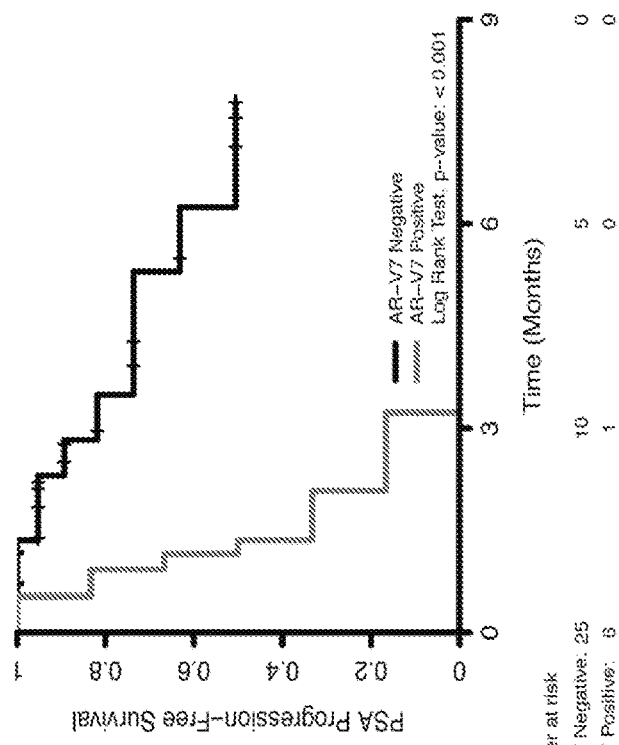
FIGS. 5A and 5B show representative data pertaining to Kaplan-Meier analysis of PSA-progression-free-survival [PSA-PFS] stratified by CTC AR-V7 status in either enzalumatide-treated patients (5A) or abiraterone-treated patients (5B). Median PSA-PFS in enzalutamide-treated patients (A) was 1.4 months (95% CI, 0.9—not reached) and 6.0 months (95% CI, 3.8—not reached) in AR-V7-positive and AR-V7-negative patients, respectively (HR 7.4, 95% CI 2.7-20.6, log-rank P<0.001). Median PSA-PFS in abiraterone-treated patients (B) was 1.3 months (95% CI, 0.9—not reached) and >5.3 months (95% CI, 5.3—not reached) in AR-V7-positive and AR-V7-negative patients, respectively (HR 16.1, 95% CI 3.9-66.0, log-rank P<0.001).
Figure 5A:
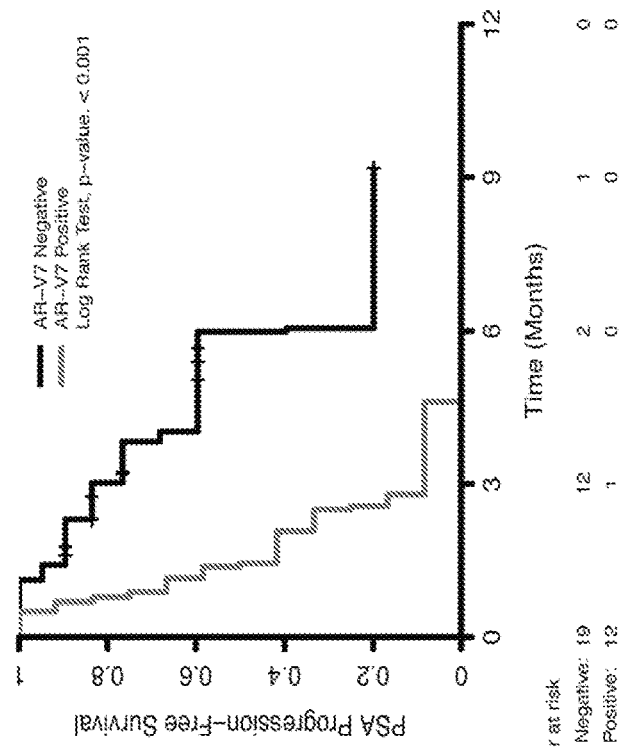

Among enzalutamide-treated patients, PSA-progression-free-survival (PSA-PFS) was inferior in men with baseline detectable (versus undetectable) AR-V7 transcripts (univariate P<0.001) (FIG. 5A). In a multivariable Cox model adjusting for AR-FL expression and prior abiraterone use, AR-V7 presence remained independently predictive of PSA-PFS (HR 3.1, 95% CI 1.0-9.2, P=0.046); AR-FL levels were also predictive of PSA-PFS (HR 1.4, 95% CI 1.0-1.9, P=0.051), but not previous abiraterone use (HR 2.5, 95% CI 0.4-14.5, P=0.294). Results of the propensity score weighted multivariable model are shown in Table 6.

Referring to FIG. 5A, the median PSA-PFS in enzalutamide-treated patients was 1.4 months (95% CI, 0.9—not reached) and 6.0 months (95% CI, 3.8—not reached) in AR-V7-positive and AR-V7-negative patients, respectively (HR 7.4, 95% CI 2.7-20.6, log-rank P<0.001).

TABLE 6

| Variable | Hazard Ratio (HR) | 95% Confidence Interval (95% CI) | P value |
| --- | --- | --- | --- |
| AR-V7 Positive | 3.40 | (1.43-8.08) | 0.006 |
| AR-FL Level (log) | 1.33 | (1.03-1.72) | 0.029 |
| Prior use of Abiraterone | 2.66 | (0.72-9.86) | 0.145 |

Among abiraterone-treated patients, PSA-PFS was inferior in men with baseline detectable (versus undetectable) AR-V7 levels (univariate P<0.001) (FIG. 5B). In a multivariable Cox model adjusting for AR-FL expression and prior enzalutamide use, AR-V7 detection was the only independent predictor of PSA-PFS (HR 15.7, 95% CI 2.1-117.5, P=0.007); neither AR-FL levels (HR 1.0, 95% CI 0.8-1.2, P=0.817) nor previous enzalutamide use (HR 0.9, 95% CI 0.1-5.2, P=0.869) were predictive of PSA-PFS. The propensity score weighted multivariable model is shown in Table 7.

Referring to FIG. 5B, the median PSA-PFS in abiraterone-treated patients was 1.3 months (95% CI, 0.9—not reached) and >5.3 months (95% CI, 5.3—not reached) in AR-V7-positive and AR-V7-negative patients, respectively (HR 16.1, 95% CI 3.9-66.0, log-rank P<0.001).

TABLE 7

| Variable | Hazard Ratio (HR) | 95% Confidence Interval (95% CI) | P value |
| --- | --- | --- | --- |
| AR-V7 Positive | 17.51 | (3.53-87.03) | <0.002 |
| AR-FL Level (log) | 1.05 | (0.87-1.25) | 0.629 |
| Prior use of Abiraterone | 0.61 | (0.17-2.19( | 0.445 | b. PFS

Among enzalutamide-treated patients, clinical/radiographic-progression-free-survival (PFS) was inferior in men with baseline detectable AR-V7 (univariate P<0.001) (FIG. 5C). In a multivariable Cox model adjusting for AR-FL expression and prior abiraterone use, AR-V7 presence remained predictive of PFS (HR 3.0, 95% CI 0.9-9.6, P=0.064); AR-FL levels were also predictive of PFS (HR 1.7, 95% CI 1.1-2.6, P=0.017), but not previous abiraterone use (HR 2.6, 95% CI 0.2-27.6, P=0.433). Table 8 shows the propensity score weighted multivariable model.

Referring to FIG. 5C, the median PFS in enzalutamide-treated patients was 2.1 months (95% CI, 2.0—not reached) and 6.1 months (95% CI, 4.7—not reached) in AR-V7-positive and AR-V7-negative patients, respectively (HR 8.5, 95% CI 2.8-25.5, log-rank P<0.001).

TABLE 8

| Variable | Hazard Ratio (HR) | 95% Confidence Interval (95% CI) | P value |
| --- | --- | --- | --- |
| AR-V7 Positive | 3.38 | (1.35-8.46) | 0.009 |
| AR-FL Level (log) | 1.64 | (1.14-2.35) | 0.007 |
| Prior use of Abiraterone | 1.54 | (0.31-7.79) | 0.602 |

Among abiraterone-treated patients, PFS was inferior in men with baseline detectable AR-V7 (univariate P<0.001) (FIG. 5D). In a multivariable Cox model adjusting for AR-FL expression and prior enzalutamide use, AR-V7 detection was the only factor that was independently predictive of PFS (HR 7.6, 95% CI 1.0-57.6, P=0.050); AR-FL levels (HR 1.1, 95% CI 0.9-1.5, P=0.387) and previous enzalutamide use (HR 1.9, 95% CI 0.4-10.0, P=0.439) were not predictive of PFS. Table 9 shows the propensity score weighted multivariable model.

Referring to FIG. 5D, the median PFS in abiraterone-treated patients was 2.3 months (95% CI, 1.4—not reached) and >6.3 months (95% CI, 6.3—not reached) in AR-V7-positive and AR-V7-negative patients, respectively (HR 16.5, 95% CI 3.3 82.9, log-rank P<0.001).

TABLE 9

| Variable | Hazard Ratio (HR) | 95% Confidence Interval (95% CI) | P value |
| --- | --- | --- | --- |
| AR-V7 Positive | 5.25 | (1.09-25.21) | 0.038 |
| AR-FL Level (log) | 1.36 | (0.97-1.90) | 0.075 |
| Prior use of Abiraterone | 1.72 | (0.50-5.92) | 0.392 | c. OS

A preliminary survival analysis was conducted after 10 deaths in the enzalutamide-treated cohort (32% maturity; median follow-up 8.4 months) and after 5 deaths in the abiraterone-treated cohort (16% maturity; median follow-up 9.3 months). OS was inferior in men with baseline detectable AR-V7 both in the enzalutamide cohort (HR 6.9, 95%

CI 1.7-28.1, log-rank P=0.002) (FIG. 5E) and in the abiraterone cohort (HR 12.7, 95% CI 1.3-125.3, log-rank P=0.006) (FIG. 5F). Due to the small number of events in each cohort, multivariable models were not constructed.

Referring to FIG. 5E, the median OS in enzalutamide-treated patients was 5.5 months (95% CI, 3.9—not reached) and not reached (95% CI, not reached-not reached) in AR-V7-positive and AR-V7-negative patients, respectively (HR 6.9, 95% CI 1.7-28.1, log-rank P=0.002).

Referring to FIG. 5F, the median OS in abiraterone-treated patients was 10.6 months (95% CI, 8.5—not reached) and >11.9 months (95% CI, 11.9—not reached) in AR-V7-positive and AR-V7-negative patients, respectively (HR 12.7, 95% CI 1.3-125.3, log-rank P=0.006).

6. Combined Analysis

As an exploratory analysis, PSA responses were evaluated, PSA-PFS, PFS and OS using the combined patient population including all 62 subjects. Without wishing to be bound by theory, these data indicate that the impact of AR-V7 status on these outcomes remained significant (FIG. 6A-D).

Figure 6A:
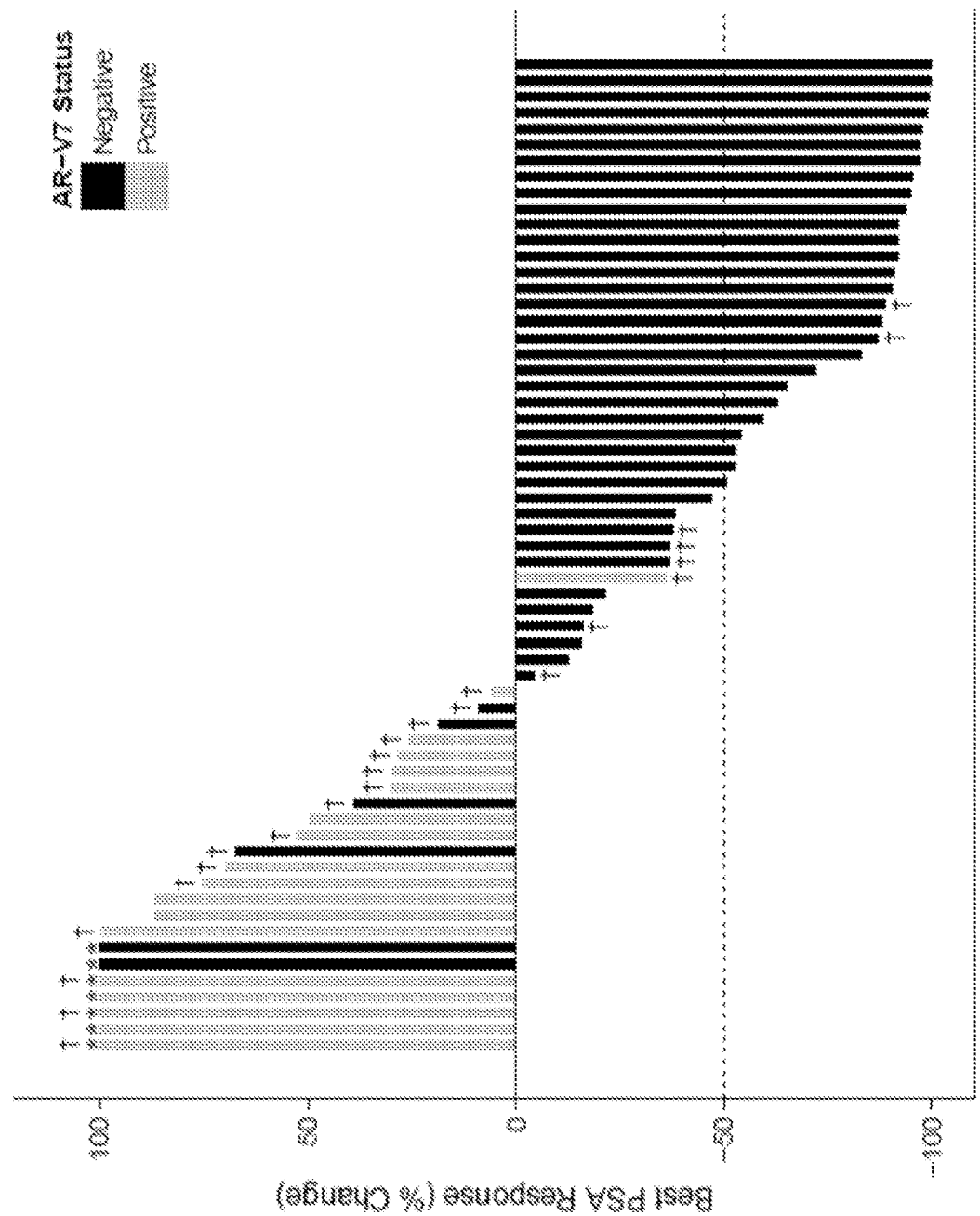
FIGS. 6A-D show representative data pertaining to the combined analysis of patient outcome by AR-V7 status.

Referring to FIG. 6A, a waterfall plot showing best PSA responses according to CTC AR-V7 status for all 62 patients is shown. The 'asterisk' marks (*) indicate clipped bars.

The dotted line shows the threshold for defining a PSA response. Men who had previously received abiraterone and enzalutamide (in the enzalutamide and abiraterone cohorts, respectively) are denoted with 'dagger' marks (†). The overall proportion of patients who achieved a PSA response to either therapy was 44% (27/62 men; 95% CI, 31-57%). PSA response rates were 0% (0/18 men; 95% CI, 0-19%) in AR-V7-positive patients and 61% (27/44 men; 95% CI, 45-76%) in AR-V7-negative patients (P<0.001). Considered alternatively, among patients achieving a PSA response, 0% (0/27 men; 95% CI, 0-13%) were AR-V7-positive; while in patients not achieving a PSA response, 51% (18/35 men; 95% CI, 34-69%) were AR-V7-positive. In linear regression modeling, AR-V7 status remained predictive for PSA response after adjusting for AR-FL expression levels (P<0.001).

Figure 6B:
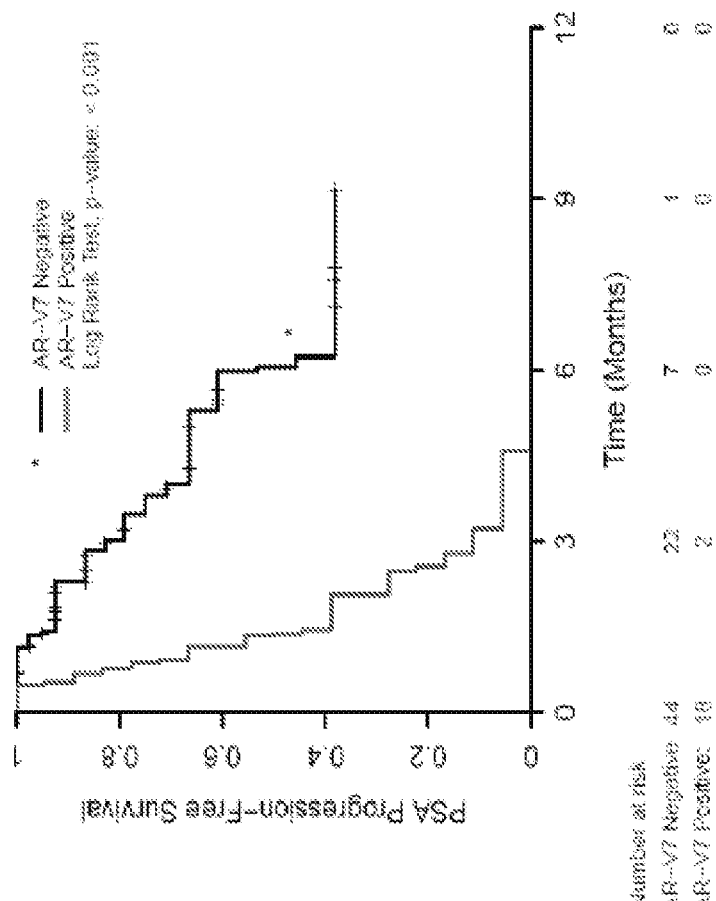

Referring to FIG. 6B, Kaplan-Meier curves showing PSA-progression-free-survival [PSA-PFS] stratified by CTC AR-V7 status in all 62 patients are shown. Median PSA-PFS was 1.4 months (95% CI, 0.9-2.6) and 6.1 months (95% CI, 5.3—not reached) in AR-V7-positive and AR-V7-negative patients, respectively (HR 10.5, 95% CI 4.7-23.6, log-rank P<0.001). In multivariable Cox regression analysis stratified by treatment type, AR-V7 detection remained independently predictive of PSA-PFS (HR 8.2, 95% CI 2.7-24.9, P<0.001). Presence of visceral metastases (P=0.033) and more prior hormonal therapies (P=0.031) were also predictive of PSA-PFS; while AR-FL level (P=0.120), prior use of enzalutamide/abiraterone (P=0.068), and baseline PSA level (P=0.064) were not predictive.

Figure 6C:
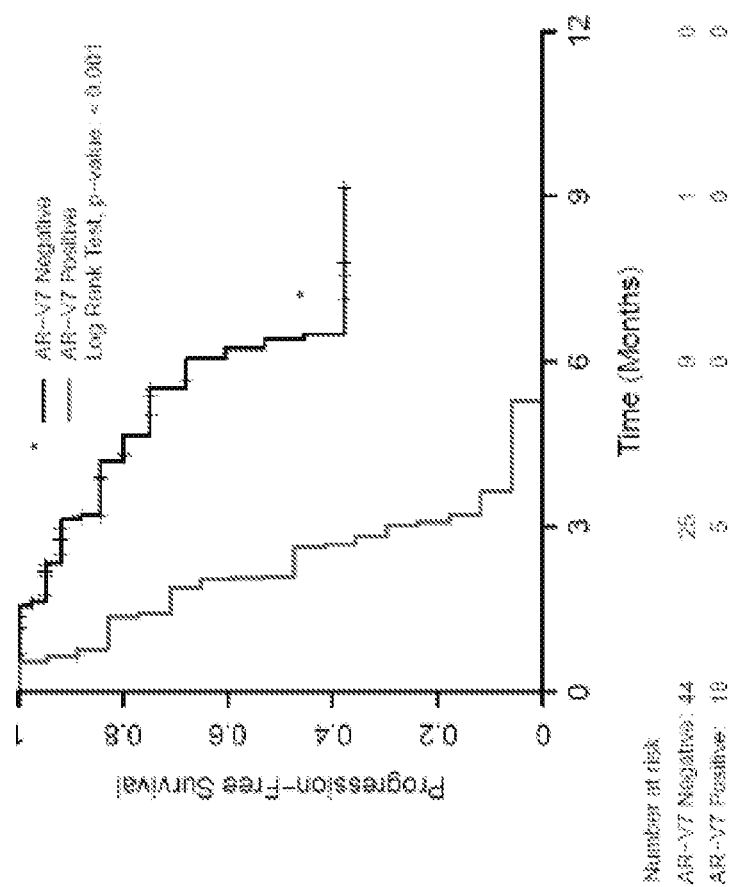

Referring to FIG. 6C, Kaplan-Meier curves showing clinical/radiographic-progression-free-survival [PFS] stratified by CTC AR-V7 status in all 62 patients are shown. Median PFS was 2.1 months (95% CI, 1.9-3.1) and 6.4 months (95% CI, 6.1—not reached) in AR-V7-positive and AR-V7-negative patients, respectively (HR 12.7, 95% CI 5.1-31.9, log-rank P<0.001). In multivariable Cox regression analysis stratified by treatment type, AR-V7 detection remained independently predictive of PFS (HR 4.9, 95% CI 1.7-13.8, P=0.003). AR-FL levels (P=0.023), more prior hormonal therapies (P=0.037) and prior use of enzalutamide/abiraterone (P=0.014) were also predictive of PFS; while baseline PSA level (P=0.088), and presence of visceral metastases (P=0.422) were not predictive.

Figure 6D:
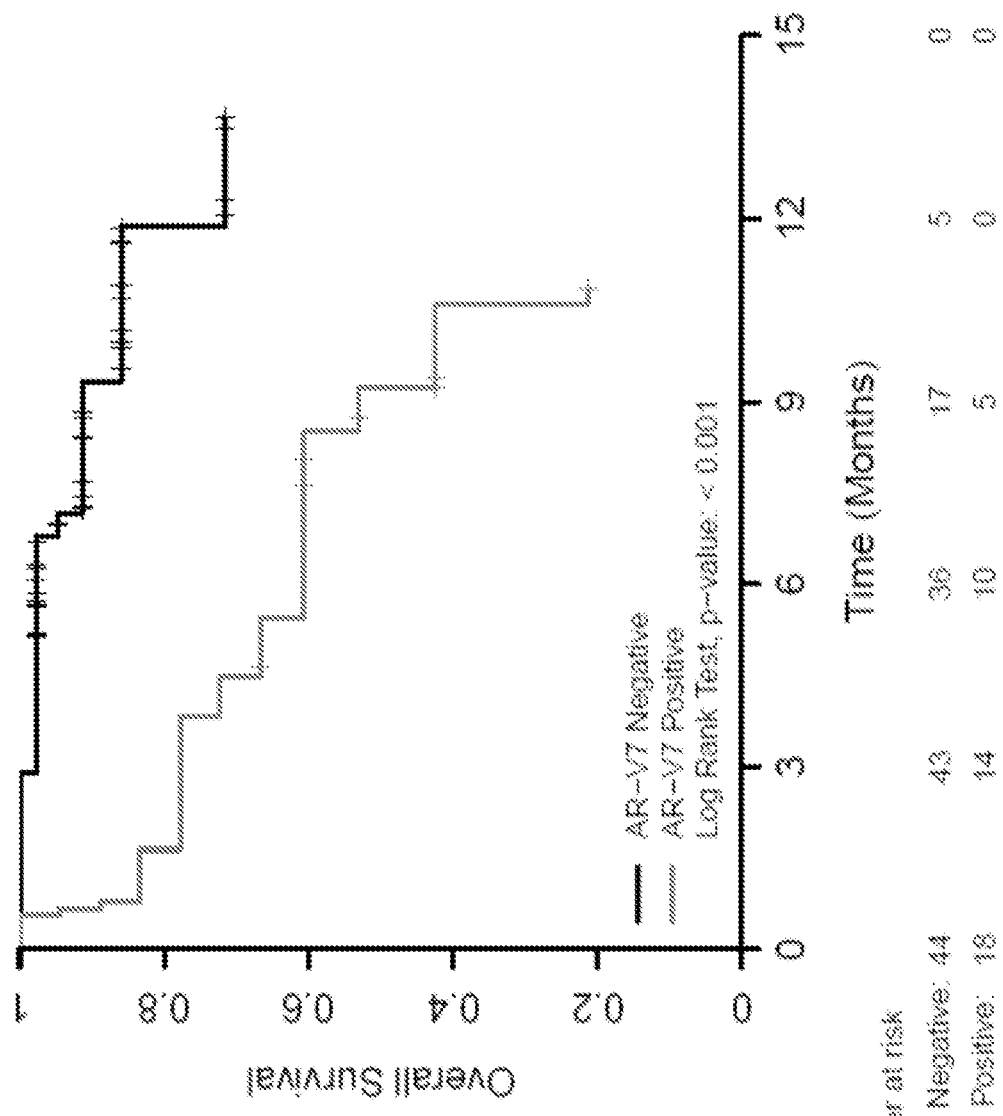

Referring to FIG. 6D, Kaplan-Meier curves showing overall survival [OS] stratified by CTC AR-V7 status in all 62 patients are shown. Median OS was 9.2 months (95% CI, 4.5—not reached) and >11.9 months (95% CI, 11.9—not reached) in AR-V7-positive and AR-V7-negative patients, respectively (HR 8.3, 95% CI 2.5-27.4, log-rank P<0.001). In multivariable Cox regression analysis stratified by treatment type, AR-V7 detection remained independently predictive of OS (HR 5.0, 95% CI 1.3-19.8, P=0.021). Prior use of enzalutamide/abiraterone was also predictive of OS (P=0.027), while AR-FL level was not predictive (P=0.524).

7. AR-V7 'Conversions'

Among men with initially undetectable AR-V7 and ≥1 additional follow-up sample (n=42), six patients (4 on enzalutamide, 2 on abiraterone) subsequently 'converted' to AR-V7-positive during the course of treatment, while all 16 patients with initially detectable AR-V7 (with ≥1 follow-up sample) remained AR-V7-positive during treatment. Clinical outcomes for these patients are summarized in Table 10. Changes in AR-V7 expression levels during the course of treatment are summarized in FIGS. 7A and 7B.

It should be noted that the timing of the subsequent sample collection has not been taken into account, and time-dependent covariate analysis or landmark analysis were not performed to adjust for this. Therefore, the clinical outcomes in each group cannot be formally compared with each other, and are provided for descriptive purposes only.

Figure 7A:
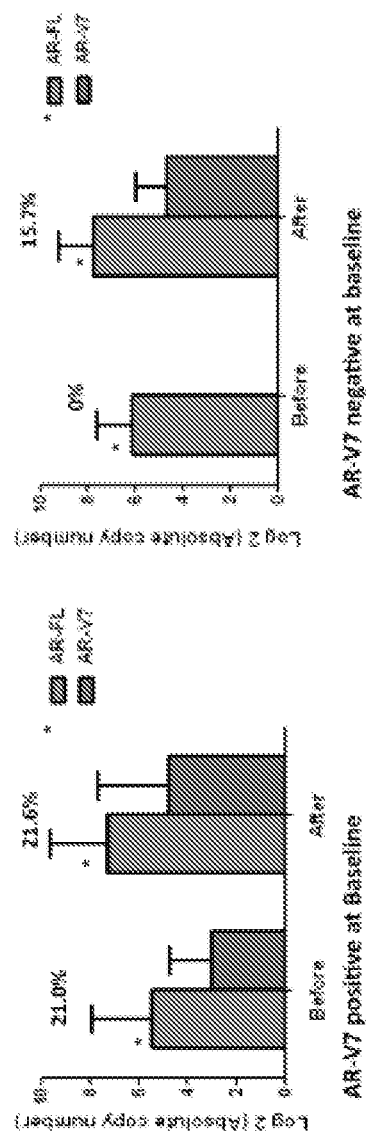
FIGS. 7A and 7B show representative data pertaining to changes in AR-V7 and AR-FL transcript copy numbers detected in CTCs before and after treatment with enzalutamide and abiraterone.

Referring to FIG. 7A, alterations in AR-FL and AR-V7 transcript copy numbers before and after enzalutamide/abiraterone treatment are shown in patients with baseline detectable AR-V7 (n=16, with paired samples available) (left panel) and in patients who converted from initially undetectable to later detectable AR-V7 (n=6) (right panel). Higher copy numbers for both AR-FL and AR-V7 were detected in CTC samples collected after treatment (at the time of resistance to therapy) compared to baseline (pre-treatment) samples. Note that the AR-V7/AR-FL ratio is similar between samples collected before and after treatment in patients with baseline detectable AR-V7 (~21%), and that an average AR-V7/AR-FL ratio of 15.7% was detected in patients who converted from initially undetectable to later detectable AR-V7. In patients who converted from initially undetectable to later detectable AR-V7, copy number values for AR-V7 were generated from the last follow-up CTC samples (see FIG. 7B, below).

Figure 7B:
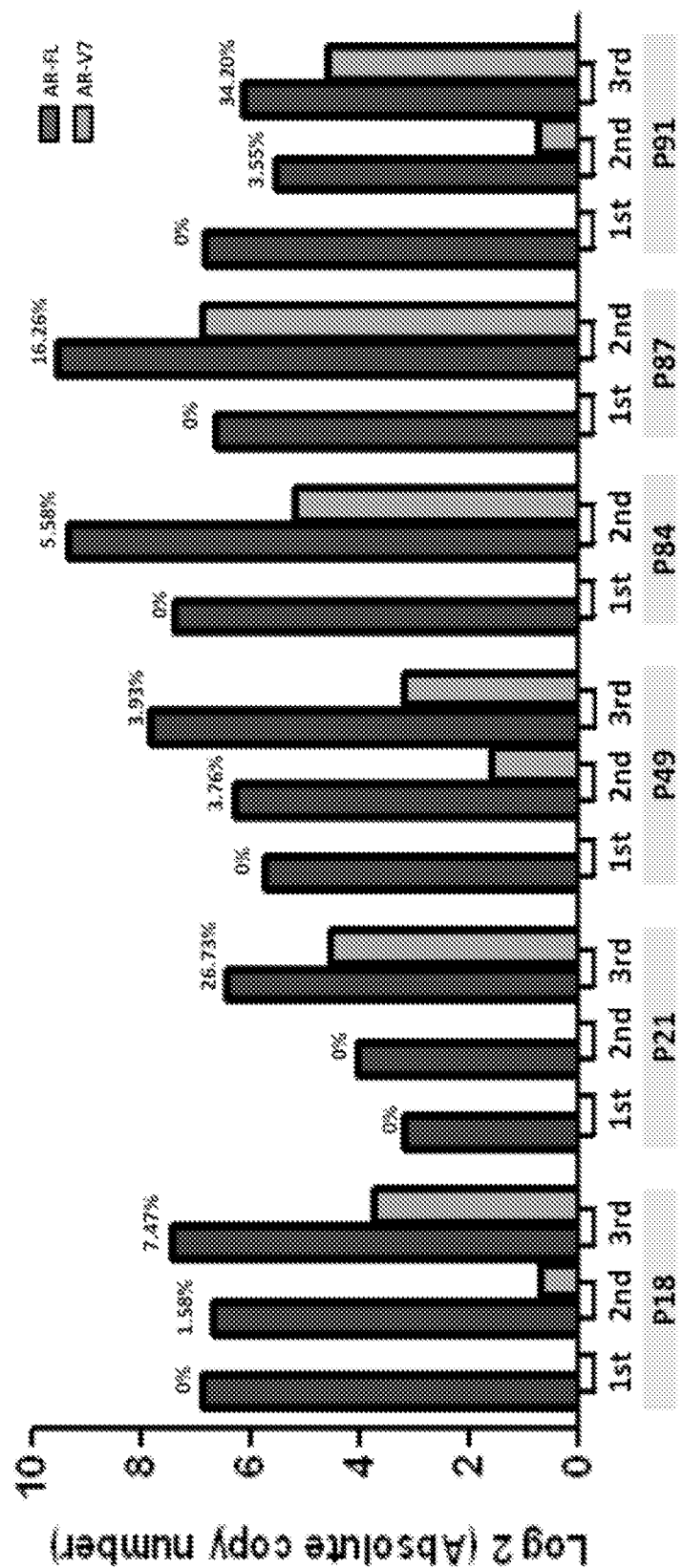

Referring to FIG. 7B, AR transcript copy numbers detected in the 6 patients whose AR-V7 status was negative at baseline but converted to positive during treatment are shown. Absolute transcript copy numbers for AR-FL and AR-V7 are shown for each of the 6 patients before, during, and after treatment with enzalutamide or abiraterone (1st: before treatment; 2nd: during treatment; 3rd: at the time of progression). The percentage values represent the ratio of the absolute copy number of AR-V7 to AR-FL in CTCs. As shown, absolute AR-V7 levels (and AR-V7/AR-FL ratios) increased with time in all 6 cases. Patients P18, P21, P49 and P87 were treated with enzalutamide. Patients P84 and P91 were treated with abiraterone.

TABLE 10

| Outcome | AR-V7[−] → AR-V7[−] (n = 36) | AR-V7[−] → AR-V7[+] (n = 6) | AR-V7[+] → AR-V7[+] (n = 16) |
| --- | --- | --- | --- |
| PSA Response | 68% (95% CI, 52-81%) | 17% (95% CI, 4-58%) | 0% (95% CI, 0-19%) |
| PFA-PFS | 6.1 months (95% CI, 5.9 mo-NA) | 3.0 months (95% CI, 2.3 mo-NA) | 1.4 months (95% CI, 0.9-2.6 mo) |
| PFS | 6.5 months (95% CI, 6.1 mo-NA) | 3.2 months (95% CI, 3.1 mo-NA) | 2.1 months (95% CI, 1.9-3.1 mo) |

[a]Of the 44 patients who were AR-V7 - negative at baseline, 42 had at least one follow-up sample collected; 36 of these men (86%) remained AR-V7 - negative at follow-up (AR-V7[−] → AR-V7[−]), while 6 of these men (14%) converted to AR-V7 - positive at follow-up (AR-V7[−] → AR-V7[+]). Of the 18 patients who were AR-V7 - positive at baseline, 16 had at least one follow-up sample collected; all of these men remained AR-V7 - positive at follow-up (AR-V7[+] → AR-V7[+]). The clinical outcomes of these patients are also shown.

8. Tissue-Based Analyses

Figure 8:
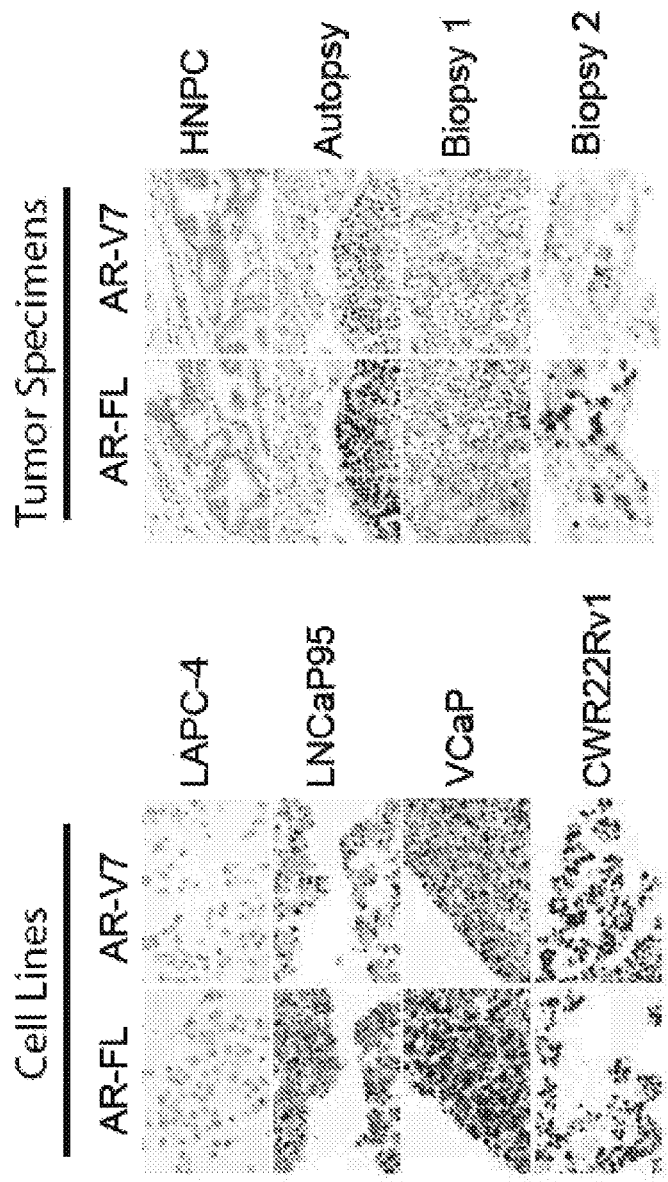
FIG. 8 shows representative data pertaining to the detection of AR-V7 transcripts in metastatic prostate cancer tissues. In situ detection of AR-FL and AR-V7 mRNA in cell lines with known expression of AR-FL and AR-V7 (left panel), and in prostate cancer tumor specimens (right panel). Three of the prostate cancer cell lines shown (LNCaP95, VCaP and CWR22Rv1) express AR-FL as well as AR-V7, while the LAPC-4 line is positive only for AR-FL but negative for AR-V7, as visualized using RNA-ISH analysis. The tumor tissue specimens shown include a hormone-naïve radical prostatectomy specimen that lacks AR-V7 expression (HNPC; not one of the patients enrolled in this study), an autopsy-derived liver metastasis from a patient with positive AR-V7 in CTCs (Autopsy), and core-needle biopsy specimens from patients with negative (Biopsy 1) and positive (Biopsy 2) AR-V7 in CTCs. All the tumor specimens shown on the right panel demonstrate expression of AR-FL.
Figure 9:
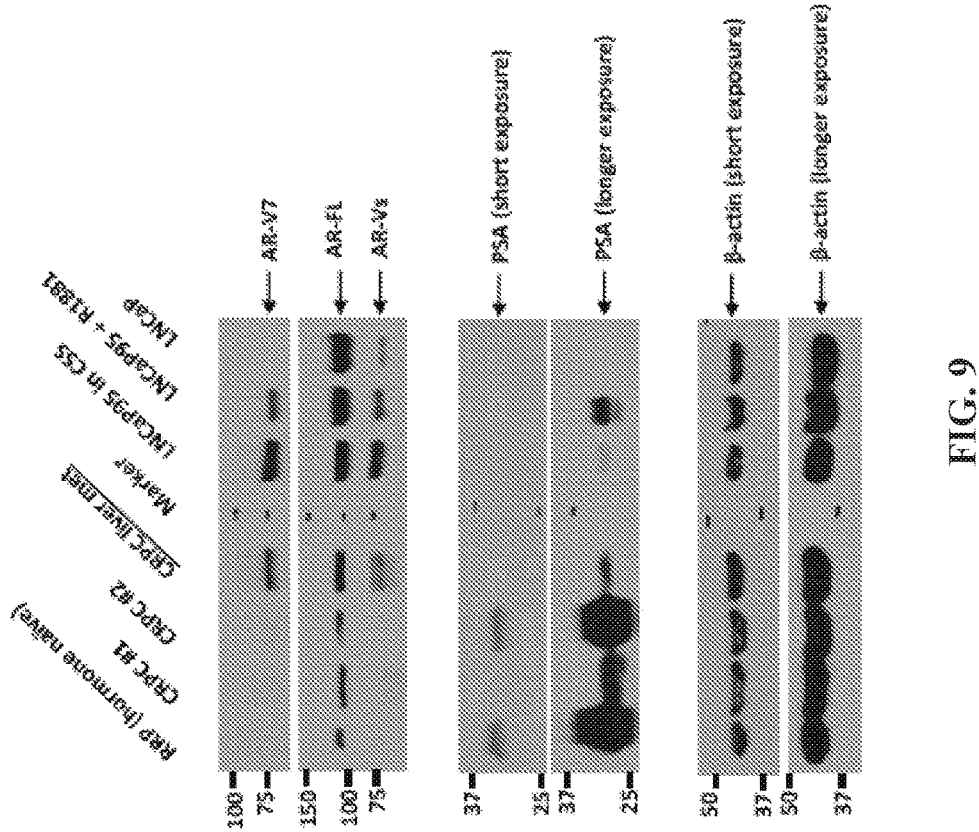
FIG. 9 provides graphical depiction showing detection of AR-V7 at the protein level using Western blot analysis in patients with detectable AR-V7 transcripts in CTCs.

Seven patients consented to additional tissue-based studies: 5 underwent metastatic tumor biopsies, and 2 allowed research autopsies after their death. Three of the seven patients had detectable AR-V7 from CTCs; these three patients also had detectable AR-V7 in metastatic tumor tissue using qRT-PCR and RNA-ISH analysis (FIG. 8). In addition, AR-V7 (and AR-FL) was detected at the protein level using Western blot analysis in these patients (FIG. 9). Conversely, none of the 4 patients with undetectable AR-V7 in CTCs had detectable AR-V7 by RNA-ISH in metastatic tissue, suggesting good concordance. Finally, sequencing of the AR transcript using RNA-Seq in metastatic lesions from two AR-V7-positive patients (autopsy specimens) did not identify AR mutations that could explain resistance, but did confirm the presence of AR-V7 splice junctions in both patients (FIGS. 10A and 10B).

Referring to FIG. 8, in situ detection of AR-FL and AR-V7 mRNA in cell lines with known expression of AR-FL and AR-V7 (left panel), and in prostate cancer tumor specimens (right panel) are shown. Three of the prostate cancer cell lines shown (LNCaP95, VCaP and CWR22Rv1) express AR-FL as well as AR-V7, while the LAPC-4 line is positive only for AR-FL but negative for AR-V7, as visualized using RNA-ISH analysis. The tumor tissue specimens shown include a hormone-naïve radical prostatectomy specimen that lacks AR-V7 expression (HNPC; not one of the patients enrolled in this study), an autopsy-derived liver metastasis from a patient with positive AR-V7 in CTCs (Autopsy), and core-needle biopsy specimens from patients with negative (Biopsy 1) and positive (Biopsy 2) AR-V7 in CTCs. All the tumor specimens shown on the right panel demonstrate expression of AR-FL.

Referring to FIG. 9, detection of AR-V7 protein expression in a representative tissue sample, in this case from a liver metastasis from an AR-V7-positive patient (underlined label), is shown. Whole protein extractions were prepared from cryosections using RIPA buffer with protease inhibitors and phosphatase inhibitors. 40 μg of protein from each sample was separated on a 10% SDS-PAGE precast gel and blotted with anti-AR-V7, anti-AR (N20) (for detection of both AR-FL and AR-Vs), anti-PSA, and anti-β-actin antibodies. The LNCaP cell line served as the negative control for AR-V7; the LNCaP95 cell line (in the presence or absence of synthetic androgen, R1881) served as the positive control for AR-V7. Also shown for comparison are samples from a hormone-naïve radical prostatectomy specimen (RRP), and two metastatic tissue samples from AR-V7-negative patients (CRPC #1 and CRPC #2). Molecular weight marks are indicated to the left of the blots.

Figure 10A:
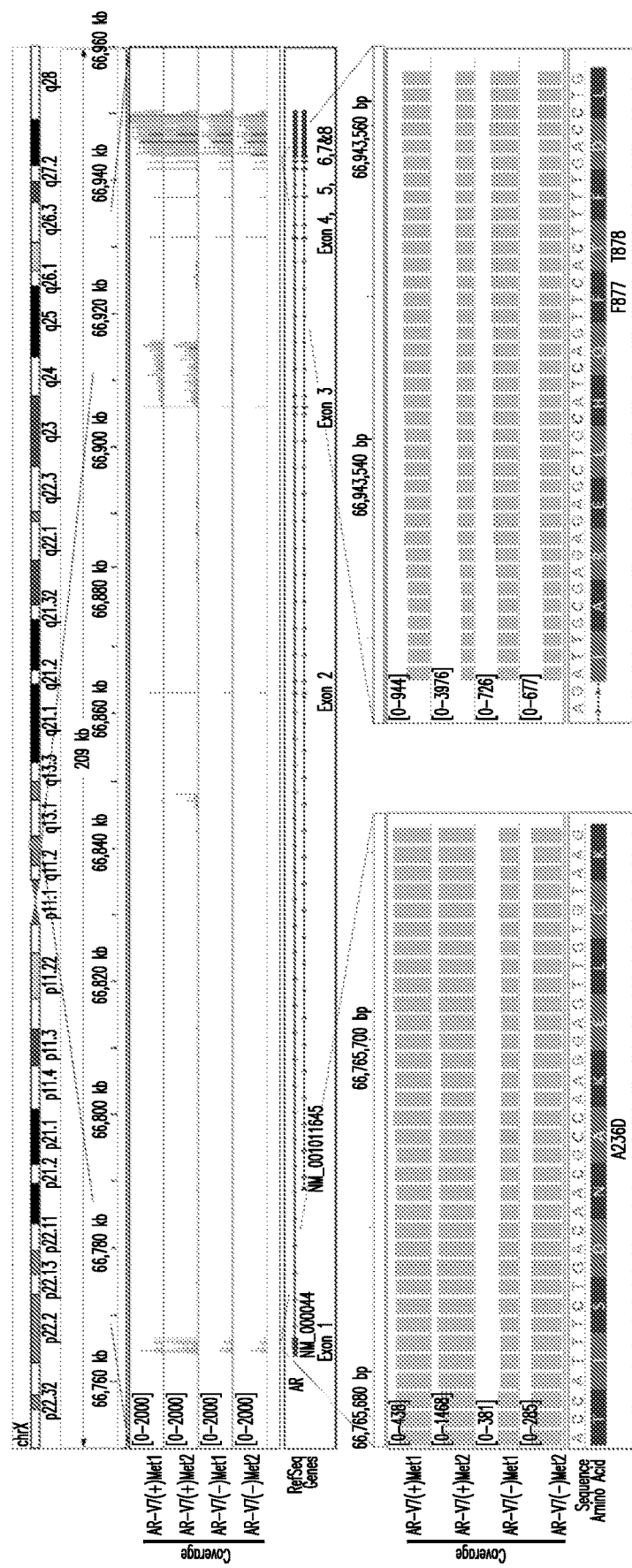
FIGS. 10A-B provide RNA-Seq analysis of the AR transcript in two AR-V7-positive patients and two AR-V7-negative patients.
Figure 10B:
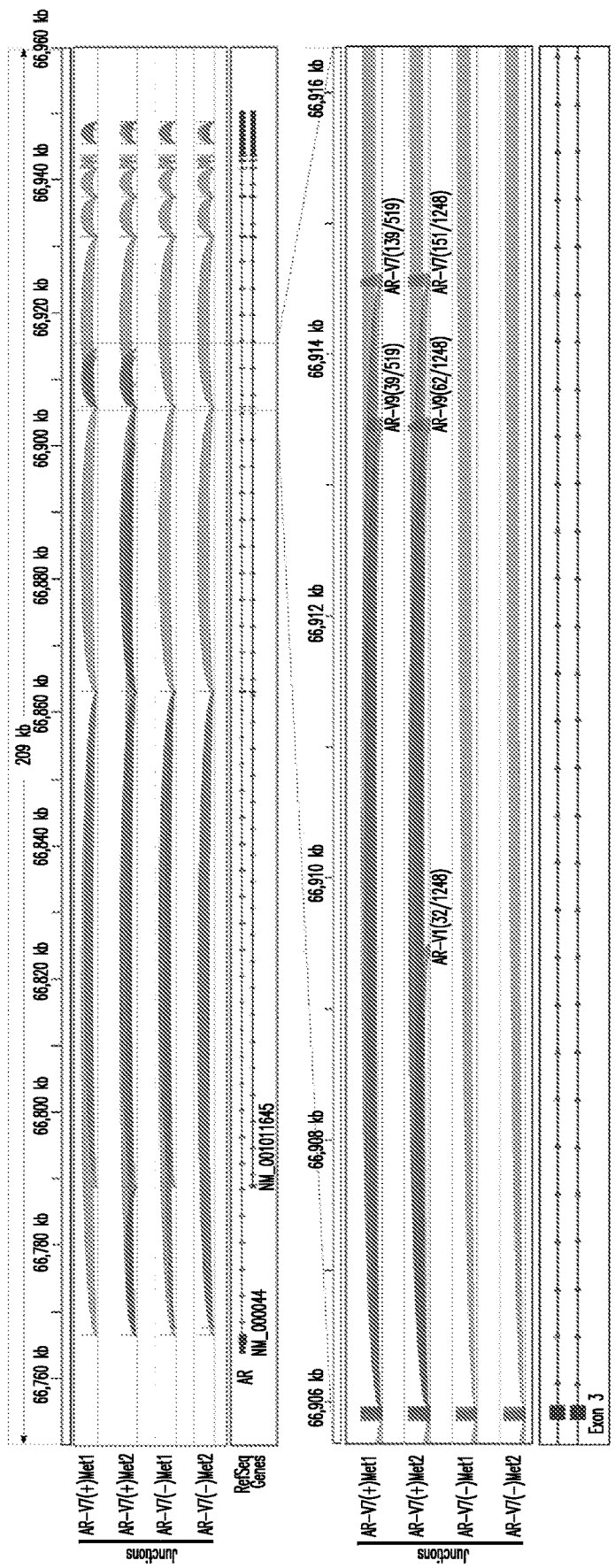

Referring to FIG. 10A, read coverage is shown along the AR gene, with the enlarged view showing a novel AR mutation (A236D) in exon 1 (of unknown significance), but a lack of known AR ligand-binding domain (LBD) mutations F876L and T877A previously implicated in castration resistance and enzalutamide resistance (note: due to Refseq sequence changes, the numbering of amino acid positions have increased by one).

Referring to FIG. 10B, AR RNA splice junction tracks depicting sequence reads connecting canonical and cryptic AR exons are shown (junctions supported by a read depth of at least 20 are shown in the figure). The enlarged region spanning exon 3 and intron 3 shows positively identified AR-V7 variants (along with AR-VI and AR-V9) in the tissue samples from the two AR-V7-positive patients. Numbers in parentheses indicate the number of variant-specific reads over the number of AR-FL-specific reads. The AR-V7/AR-FL ratios were 26.8% and 12.1%, for AR-V7(+) Met1 and AR-V7(+) Met2, respectively.

9. AR Signaling Alterations

Figure 11:
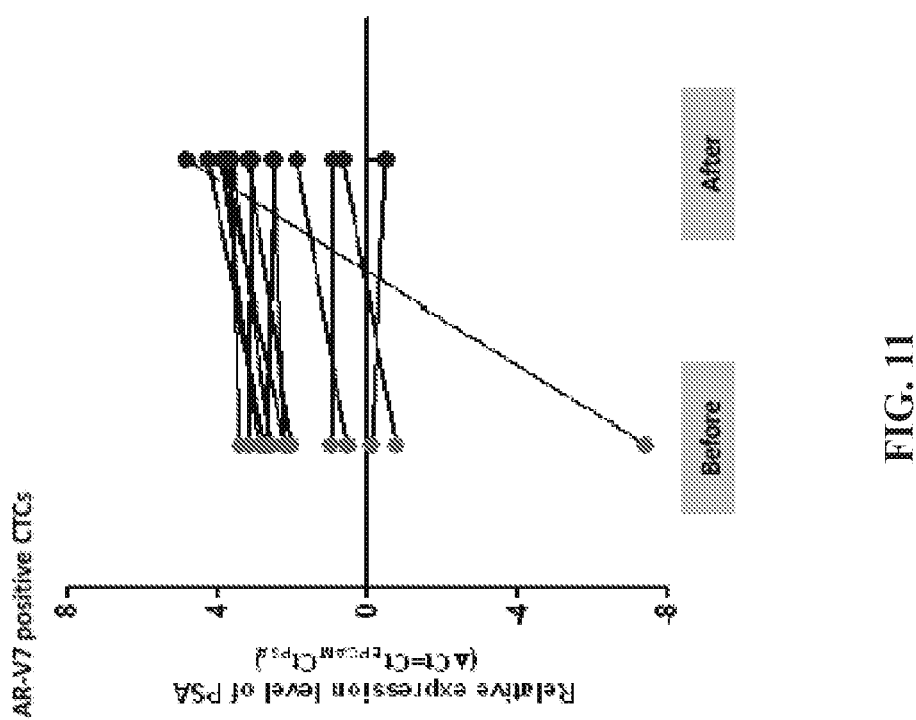
FIG. 11 provides a graph showing changes in expression of the PSA transcript before and after therapy with enzalutamide or abiraterone in men with baseline detectable AR-V7.

In all patients with detectable AR-V7, AR-FL was also expressed and at higher levels (with one exception); increased expression of AR-V7 was generally (but not always) coupled with that of AR-FL (FIG. 3A-C). While expression of PSA (an indicator of canonical-AR signaling) was generally suppressed in AR-V7-negative patients during treatment with enzalutamide/abiraterone, PSA expression did not decrease in post-treatment CTC samples from men with baseline detectable AR-V7 (FIG. 11). Without wishing to be bound by theory, these data suggest a resistance mechanism independent of AR-FL, the intended drug target. In addition, genome-wide comparisons of two AR-V7-negative and two AR-V7-positive metastatic tumor samples by Gene Set Enrichment Analysis of RNA-Seq data (FIGS. 10A, 10B, and 12), or by targeted analysis of a set of canonical-AR-regulated genes (Table 11), both revealed alterations consistent with a shift toward AR-V7-driven transcription in AR-V7-positive samples.

Referring to FIG. 11, PSA expression changes in CTC samples from AR-V7-positive patients before and after treatment with enzalutamide/abiraterone (n=14), as assessed by qRT-PCR are shown. Results are shown as the difference in Ct value between EPCAM and PSA expression ($Ct_{EPCAM}-Ct_{PSA}$). As depicted, PSA expression was generally increased during treatment with enzalutamide/abiraterone in AR-V7-positive patients, suggesting that canonical AR signaling (as indicated by levels of PSA mRNA normalized to those of EPCAM) was not inhibited by enzalutamide/abiraterone in the presence of AR-V7.

Figure 12A:
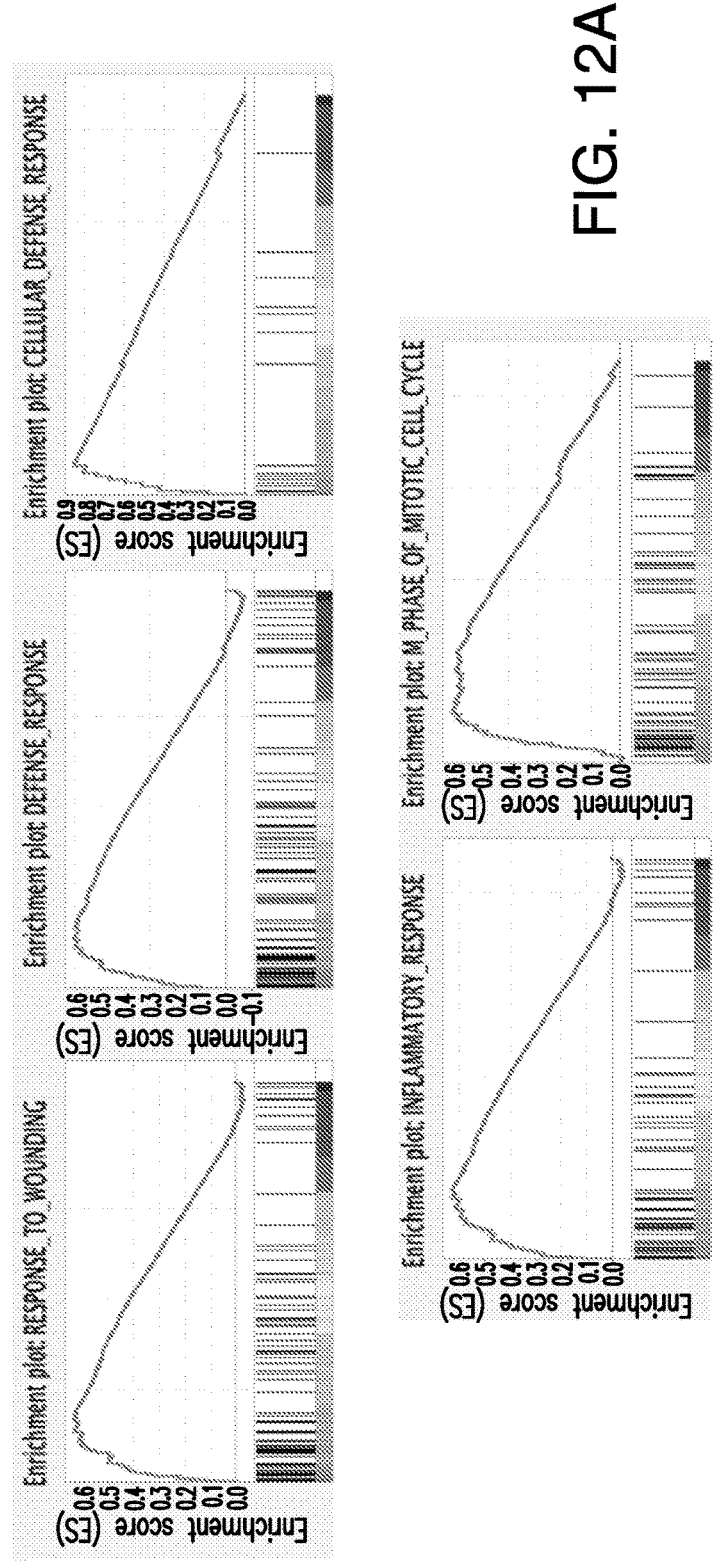
FIG. 12 provides gene set enrichment analysis of metastatic tumors from AR-V7-positive and AR-V7-negative patients.

Referring to FIG. 12, top ranked 'biological processes' enriched in genes differentially expressed between AR-V7-positive and AR-V7-negative metastatic prostate cancer tissues are shown. Genes are pre-ranked based on fold expression changes.

Consistent with the 'AR-V7 up' and 'AR-FL up' gene signatures previously reported (Hu, R., et al. (2012) *Cancer Res* 72, 3457-3462), cell cycle genes are enriched for increased expression in AR-V7-positive samples and genes involved in Golgi activities are downregulated.

Referring to FIG. 13, Table 11, expression profiles are provided for AR-regulated genes in AR-V7-negative metastatic tumors. A total of 34 canonical AR regulated genes were identified by combined analysis of downloaded expression data reported in two published studies (Hu, R., et al. 2009) *Cancer Res* 69, 16-22; Norris, J. D., et al. (2009) *Molecular cell* 36, 405-416). The AR gene did not make the selection but was added for reference. For each of the 35 genes, the number of raw RNA-Seq reads and sequencing reads normalized by "Reads Per Kilo Gene Size Per Million of Total Reads" (RPKM=number of raw counts/(genelength/1000)/(total-reads/1,000,000) in each of the four tumor samples, as well as the log fold expression change between AR-V7-positive and AR-V7-negative tumors calculated from RPKM-normalized data, are displayed. Annexed to the RNA-Seq data are previously published expression microarray data (Hu, R., et al. (2012) *Cancer Res* 72, 3457-3462) characterizing AR-V7-versus AR-FL-driven transcriptional programs (downloaded from GEO accession number GSE36549). Fold expression changes in AR-V7-positive samples when compared to AR-V7-negative tumors (log FC) are significantly correlated (P<0.001) with fold expression changes induced by AR-V7 in the absence of AR-FL activation (log FC by ARV7), on the basis of a correlation coefficient of 0.68, but not significantly correlated (p>0.05, with correlation coefficient of 0.23) with fold expression changes induced by AR-FL activation (log FC by ARFL).

DISCUSSION

Enzalutamide and abiraterone, two new AR-directed therapies, represent significant advances in the management of CRPC (Scher, H. I., et al. (2010) *Lancet* 375, 1437-1446; Scher, H. I., et al. (2012) *New England Journal of Medicine* 367, 1187-1197; Ryan, C. J., et al. (2013) *New England Journal of Medicine* 368, 138-148; de Bono, J. S., et al. (2011) *New England Journal of Medicine* 364, 1995-2005). However, a proportion of men do not benefit from these agents, and a clearer understanding of the mechanisms underlying resistance to these drugs would facilitate selection of alternative therapies (e.g. chemotherapies) for such patients. Without wishing to be bound by theory, the data provided herein suggest that AR-V7 can be reliably detected from CTCs, and that detection of AR-V7 in tumor cells may be associated with resistance to both enzalutamide and abiraterone. This conceptually simple model is biologically plausible since AR-V7 lacks the AR ligand-binding domain (the direct target of enzalutamide, and the indirect target of abiraterone), while remaining constitutively active as a transcription factor in a ligand-independent manner (Hu, R., et al. (2009) *Cancer Res* 69, 16-22; Guo, Z., et al. (2009) *Cancer Research* 69, 2305-2313). Remarkably, no AR-V7-positive patient had any appreciable clinical benefit to enzalutamide or abiraterone in this study. Moreover, while AR-V7 detection was associated with higher AR-FL expression, the prognostic impact of AR-V7 was maintained after adjusting for AR-FL levels. Finally, although prior treatment with abiraterone/enzalutamide increased the incidence of AR-V7 positivity, AR-V7 status remained prognostic after adjusting for this factor.

Since the discovery of AR splice variants 5 years ago, there has been an evolving appreciation of their role in prostate cancer biology. Preclinical studies have demonstrated that AR-Vs are found much more commonly in CRPC than in hormone-sensitive prostate cancer (Hu, R., et al. (2009) *Cancer Res* 69, 16-22), that they represent one potential mechanism driving the emergence of the castration-resistant phenotype (Nadiminty, N., et al. (2013) *Molecular cancer therapeutics* 12, 1629-1637), and that they may be responsible for CRPC progression (Hu, R., et al. (2012) *Cancer Res* 72, 3457-3462). In patients with CRPC, AR-Vs are often expressed in metastases (Hörnberg, E., et al. (2011) *PLoS ONE* 6, e19059; Zhang, X., et al. (2011) *PLoS ONE* 6, e27970), and high AR-V levels in metastatic tissues are associated with faster disease progression and shorter cancer-specific survival (Hu, R., et al. (2009) *Cancer Res* 69, 16-22; Guo, Z., et al. (2009) *Cancer Research* 69, 2305-2313; Hörnberg, E., et al. (2011) *PLoS ONE* 6, e19059). Notably, all such studies have been retrospective in nature, and none have collected serial specimens across time or investigated the clinical significance of AR-Vs in patients receiving enzalutamide or abiraterone. Importantly, several studies have shown that even though AR-Vs are constitutively-active, their function may be dependent on the activity of full-length-AR (Watson, P. A., et al. (2010) *Proceedings of the National Academy of Sciences*), although this notion has also been challenged (Nadiminty, N., et al. (2013) *Molecular cancer therapeutics* 12, 1629-1637; Hu, R., et al. (2012) *Cancer Res* 72, 3457-3462). Therefore, despite the fact that AR-Vs cannot be targeted directly by currently-available drugs, it has been hypothesized that inhibition of AR-FL by enzalutamide or abiraterone could partially reverse AR-V-mediated resistance. However, without wishing to be bound by theory, these data did not indicate any PSA responses in men harboring AR-V7 (even though all of these patients also expressed AR-FL). An alternative treatment approach for AR-V7-positive patients would be to design agents targeting the AR N-terminal domain (Sadar, M. D. (2011) *Cancer Res* 71, 1208-1213; Ravindranathan, P., et al. (2013) *Nat Commun.* 4, 1923; Andersen, R. J., et al. (2010) *Cancer cell* 17, 535-546), which would theoretically inhibit both AR-FL and AR-Vs. Indeed, such N-terminal AR inhibitors are in early stages of drug development (Ravindranathan, P., et al. (2013) *Nat Commun* 4, 1923; Andersen, R. J., et al. (2010) *Cancer cell* 17, 535-546).

In addition to the presence of AR-Vs, there may be additional explanations for primary or acquired resistance to enzalutamide and abiraterone. For instance, overexpression of CYP17 (or other steroidogenic enzymes) leading to increased intracrine/paracrine androgen synthesis has been shown to occur in patients receiving these agents (Mitsiades, N., et al. (2012) *Cancer Res* 72, 6142-6152; Efstathiou, E., et al. (2011) *ASCO Meeting Abstracts* 29, 4501; Efstathiou, E., et al. (2012) *Journal of clinical oncology: official journal of the American Society of Clinical Oncology* 30, 637-643; Chang, K. H., et al. (2013) *Cell* 154, 1074-1084). Additionally, point mutations in the AR ligand-binding domain conferring agonistic activity to enzalutamide have been described (Balbas, M. D., et al. (2013) *eLife* 2; Joseph, J. D., et al. A (2013) *Cancer Discovery*). Furthermore, expression of androgen-regulated genes may be driven by alternative steroid receptors, such as the glucocorticoid or progesterone receptors (Yu, Y., et al. (2013) *The Journal of clinical endocrinology and metabolism* 98, 2887-2896; Sahu, B., et al. (2013) *Cancer Res* 73, 1570-1580; Arora, V. K., et al. (2013) *Cell* 155, 1309-1322). Finally, AR inhibition may lead to reciprocal upregulation of other oncogenic pathways, such as the PI3K-AKT pathway (Carver, B. S., et al. (2011) *Cancer cell* 19, 575-586). Without wishing to be bound by theory, these data suggest a strong association between AR-V7 detection and enzalutamide/abiraterone resistance, and provide insight into a potentially causal mechanistic role for AR-V7 that needs to be substantiated in future studies.

Without wishing to be bound by theory, these data suggest that detection of AR-V7 in CTCs from patients with CRPC indicate resistance to both enzalutamide and abiraterone, and could have immediate clinical implications. AR-V7 status may therefore serve as a biomarker to predict resistance to enzalutamide and abiraterone, facilitate treatment selection, and fuel the development of novel agents targeting the AR N-terminal domain.

Example 2

Androgen Receptor Splice Variant-7, AR-V7, and Efficacy of Taxane Chemotherapy in Patients with Metastatic Castration-Resistant Prostate Cancer This example shows that AR-V7-positive patients retained sensitivity to taxanes, and that AR-V7 status would have a differential impact on taxane-treated men versus enzalutamide/abiraterone-treated men.

Methods.

CTCs (circulating tumor cells) were examined for AR-V7 in prospectively-enrolled patients with metastatic CRPC initiating taxane chemotherapy. A prespecified statistical plan required a sample-size of 36 taxane-treated men. Associations were evaluated between AR-V7 status and PSA-response rates, PSA-progression-free-survival (PSA-PFS), and clinical/radiographic-progression-free-survival (PFS). After incorporating updated data from Example 1 in 62 enzalutamide/abiraterone-treated patients, the interaction between AR-V7 status and treatment type was evaluated.

Results.

Thirty-seven taxane-treated patients were enrolled; 17/37 (45.9%) had detectable AR-V7. PSA responses were achieved in both AR-V7-positive and AR-V7-negative men (41% vs 65%, P=0.194). Similarly, median PSA-PFS and PFS were comparable in AR-V7-positive and AR-V7-negative patients. A significant interaction was observed between AR-V7 status and treatment type (P<0.001). In AR-V7-positive patients, PSA responses were higher in taxane-treated versus enzalutamide/abiraterone-treated men (41% vs 0%, P<0.001), and median PSA-PFS and PFS were longer in taxane-treated men (HR 0.19 for PSA-PFS, P=0.001; HR 0.21 for PFS, P=0.003).

Conclusion.

Detection of CTC-derived AR-V7 in men with CRPC is not associated with primary resistance to taxanes. In AR-V7-positive men, taxanes appear more efficacious than enzalutamide/abiraterone, but not in AR-V7-negative men. AR-V7 may represent a treatment-selection biomarker in CRPC There are currently 6 available therapies for the treatment of castration-resistant prostate cancer (CRPC), all of which have produced survival improvements.[1] These therapies fall into four classes: androgen receptor (AR)-directed therapies (abiraterone,[2] enzalutamide[3]), taxane chemotherapies (docetaxel,[4] cabazitaxel[5]), immunotherapies (sipuleucel-T[6]) and bone-targeting radiopharmaceuticals (radium-223).[7] Of these, the most widely used are the AR-targeting therapies and the chemotherapies. However, mechanisms of response and resistance to these therapies remain poorly understood.[8,9] Further, predictive biomarkers aiding in treatment selection (i.e. selecting for or against a particular therapy) are still lacking, while prognostic markers are abundant.[10]

AR splice-variants, in particular AR-variant-7 (AR-V7), are strongly associated with primary resistance to abiraterone and enzalutamide in men with CRPC.[11] AR-variants (AR-Vs) are alternatively-spliced isoforms of the AR that encode a truncated AR protein lacking the C-terminal ligand-binding domain but retaining the transactivating N-terminal domain.[12-14] Although these AR-Vs are unable to bind ligand (e.g. dihydrotestosterone), they are constitutively active and capable of promoting transcription of target genes.[14-16] To investigate the clinical relevance of AR-Vs in CRPC, a circulating tumor cell (CTC)-based assay was developed to interrogate AR-V7 in men undergoing therapy with abiraterone (an androgen-synthesis inhibitor) or enzalutamide (an AR antagonist). Detection of AR-V7 in CTCs from such patients was associated with lack of a PSA response, and that AR-V7-positive patients had shorter progression-free-survival and overall-survival than AR-V7-negative men.[11]

Recent preclinical data have emerged suggesting that taxane chemotherapies may exert their antitumor activity in CRPC (at least partially) by impairing AR signaling along the microtubule network, thereby sequestering AR in the cytoplasm.[17-20] Additionally, it has been shown that in taxane-sensitive patients, treatment produces microtubule bundling resulting in exclusion of the AR from the nucleus. Conversely, AR often remains capable of trafficking into the nucleus despite therapy in taxane-resistant patients.[19,21] Furthermore, in specific xenograft mouse models it has been suggested that certain AR splice-variants may promote resistance to taxane chemotherapies while others may be compatible with taxane sensitivity.[22] However, the clinical significance of AR-Vs in patients receiving taxanes is unknown.

This example aimed to prospectively evaluate, for the first time, the predictive impact of AR-Vs in men with CRPC undergoing taxane chemotherapy. It was hypothesized that men with detectable CTC-derived AR-V7 would retain sensitivity to taxanes, and that AR-V7 status would have a differential effect on taxane-treated men versus enzalutamide/abiraterone-treated men. This Example shows that detection of AR-V7 is not associated with primary resistance to taxane chemotherapy, and that taxanes may have superior efficacy compared to AR-targeting agents in AR-V7-positive men.

METHODS

Patients

The study enrolled men with metastatic CRPC who were beginning standard-of-care treatment with docetaxel or cabazitaxel. Patients were required to have histologically-confirmed prostate adenocarcinoma, progressive disease despite "castration levels" of serum testosterone (<50 ng/dL), and documented radiographic metastases on computed tomography (CT) or technetium-99 bone scans. Patients had to have ≥3 rising serum PSA values taken ≥2 weeks apart with the last value being ≥2.0 ng/mL, consistent with the Prostate Cancer Working Group (PCWG2) guidelines.[23] Patients were excluded if they planned to receive additional concurrent anticancer therapies (standard or investigational) during the course of taxane treatment. Prior treatment with abiraterone and/or enzalutamide was permitted, as was previous treatment with docetaxel among men starting cabazitaxel (consistent with the labeled indication[5]).

The study was approved by the Johns Hopkins University IRB, and was conducted according to Good Clinical Practice guidelines. Patients provided written informed consent.

Study Design

This was a prospective study evaluating the ability of baseline AR-V7 status to predict sensitivity or resistance to taxane agents. Patients who were about to begin docetaxel or cabazitaxel chemotherapy were enrolled, and underwent peripheral-blood CTC sampling at up to 3 time-points: at baseline, at the time of a clinical/biochemical response (if a response occurred), and at the time of clinical/radiographic progression. Docetaxel was administered at a dose of 75 mg/m$^2$ intravenously every-3-weeks, and cabazitaxel was given at a dose of 25 mg/m$^2$ intravenously every-3-weeks (both with prednisone 5 mg twice-daily).

Follow-up was prospectively-defined: patients had PSA measurements every 1-2 months, as well as CT (chest/abdomen/pelvis) and technetium-99 bone scans every 2-4 months. Therapy with docetaxel or cabazitaxel was continued until PSA-progression or clinical/radiographic-progression, or until patients developed unmanageable drug-related toxicities.

CTC Analysis for AR-V7

CTC analyses were conducted using a modification of the commercially-available Alere™ AdnaTest platform (Alere Inc, Waltham, Mass.), as previously described.[11] Briefly, isolation and enrichment of CTCs was performed using the ProstateCancerSelect kit, and mRNA expression analyses were performed using the ProstateCancerDetect kit with multiplexed reverse-transcription polymerase-chain-reaction (qRT-PCR) primers to establish the presence or absence of CTCs (this platform is not compatible with CTC enumeration). Custom primers were then used to detect the full-length AR (AR-FL) and AR-V7 at the mRNA level, as previously described.[11] The relative abundance of AR-V7 was determined by calculating the ratio of AR-V7 transcript to AR-FL transcript.

Clinical Outcomes

The primary endpoint was the PSA response rate: the proportion of patients who achieved a ≥50% PSA decline from baseline at any time-point post-therapy (and maintained for ≥3 weeks). Secondary endpoints included PSA-progression-free-survival (PSA-PFS) and clinical/radiographic-progression-free-survival (PFS). Overall-survival (OS) was an exploratory endpoint. PSA progression was defined as a ≥25% increase in PSA from nadir (and by ≥2 ng/mL), requiring confirmation ≥3 weeks later (PCWG2 criteria).[23] Clinical/radiographic progression was defined as symptomatic progression (worsening disease-related symptoms or new cancer-related complications), or radiologic progression (on CT scan: ≥20% enlargement in sum diameter of soft-tissue target lesions [RECIST criteria[24]]; on bone scan: ≥2 new bone lesions), or death, whichever occurred first.[23] OS was defined as the time to death from any cause.

Statistical Analysis

Sample size was determined based on the primary endpoint of PSA response, assuming that 30% of men would be AR-V7-positive at baseline. In the prior study,[11] enzalutamide/abiraterone-treated patients showed a difference in PSA response rates between AR-V7-positive and AR-V7-negative patients of 61% (95% CI, 43%-80%). Because it was hypothesized here that the impact of AR-V7 status would be smaller in the context of taxane-treated patients compared to enzalutamide/abiraterone-treated patients, a much smaller difference in PSA response rates was used such that the upper bound of the 95% CI for the difference was <61% (the point estimated from the previous study). Accordingly, a sample size of 36 patients produced a 2-sided 95% CI for the difference in PSA response rates between AR-V7-positive and AR-V7-negative patients with an upper bound of 60%, when the observed absolute difference is 30% (45% PSA response rate in AR-V7-negative men and 15% in AR-V7-positive men).

Clinical outcomes in taxane-treated men were compared between AR-V7-positive and AR-V7-negative patients. PSA response rates were compared using Fisher's exact test. Time-to-event outcomes (PSA-PFS, PFS, OS) were evaluated using Kaplan-Meier analysis, and survival-time differences were compared using the log-rank test. Univariate and multivariable logistic regressions (for PSA response) and Cox regressions (for time-to-event endpoints) were used to assess the effect of AR-V7 status in predicting clinical outcomes. Due to the small sample size and limited number of events, each multivariable model included only 3 covariates (AR-V7 status, AR-FL expression levels, and prior use of abiraterone and/or enzalutamide). These 3 variables were strongly associated with clinical outcomes in our prior study of AR-V7.[11]

Updated data on PSA responses, PSA-PFS, PFS and OS from our prior study of enzalutamide/abiraterone-treated patients (n=62) was incorporated in order to compare the impact of AR-V7 status (i.e. its ability to differentiate poor-prognosis from good-prognosis patients) within the context of taxane chemotherapy versus AR-directed therapy. Specifically tested was the interaction between AR-V7 status (positive or negative) and treatment type (taxane or enzalutamide/abiraterone) with respect to PSA responses, PSA-PFS, PFS and OS. Univariate and multivariable Cox regressions were used to assess the interaction of AR-V7 status and treatment type with respect to the time-to-event outcomes; each multivariable model included 6 covariates (AR-V7 status, treatment type, AR-FL expression levels, prior use of chemotherapy, prior use of enzalutamide/abiraterone, and the interaction of AR-V7 status and treatment type).

After observing significant results from the interaction tests, subgroup analyses were performed to evaluate the efficacy of different treatment types (taxane versus abiraterone/enzalutamide) in AR-V7-positive and AR-V7-negative men separately. Univariate and multivariable Cox regressions were used to assess the independent effect of treatment type within each AR-V7 subgroup. Multivariable models (constructed separately for each AR-V7 subgroup) included 3 covariates: treatment type, AR-FL expression levels, and prior use of enzalutamide/abiraterone.

All statistical tests were two-sided, and P-values ≤0.05 were considered significant. Statistical analyses were performed using the R software (version 2.15.1).

The clinical investigators were blinded to the AR-V7 data. The laboratory investigators were blinded to the clinical information when determining AR-V7 status. The study statisticians were the first to unblind the data, after ≥36 patients had been enrolled.

RESULTS

Patient Characteristics

Figure 14:
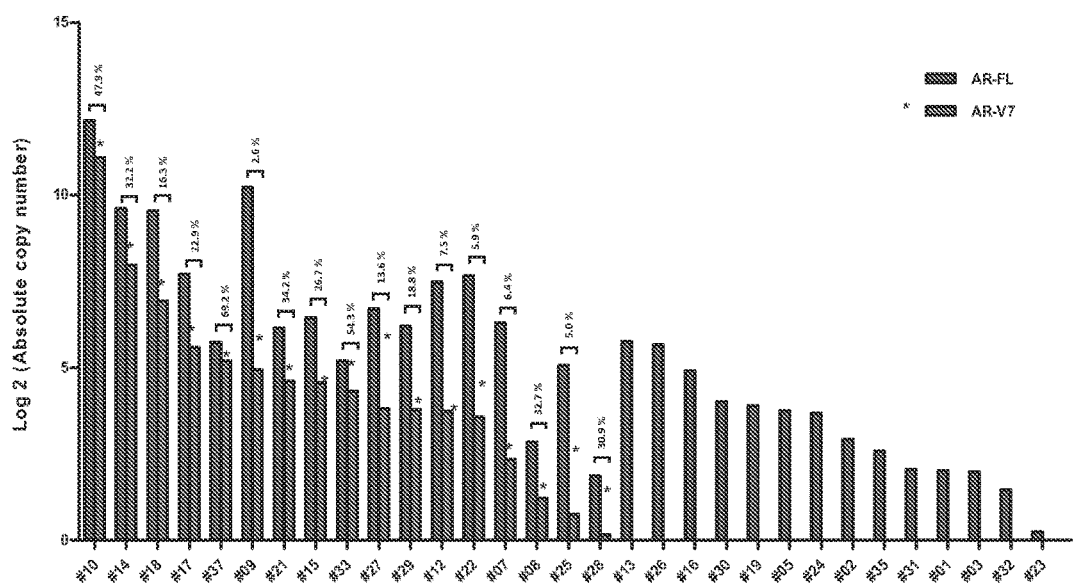
FIG. 14 is a graph showing quantification of AR-FL and AR-V7 transcript levels in CTCs from metastatic CRPC patients initiating treatment with taxane chemotherapy. Absolute transcript copy numbers of AR-FL and AR-V7 detected in circulating tumor cells (CTCs) are shown for the 17 taxane-treated patients who were positive for AR-V7 at baseline (i.e. in their pretreatment CTC samples). Ratios of AR-V7/AR-FL are expressed as percentages above each bar.

37 CTC-positive patients were enrolled: 30 received docetaxel and 7 received cabazitaxel. 43 patients were screened to identify 37 men with detectable CTCs (86% yield; CTC-negative patients were excluded from further analysis). At the data cutoff date (Sep. 1, 2014), median follow-up among all taxane-treated patients was 7.7 (range, 0.7-19.0) months. 45.9% of men (17/37) had detectable AR-V7 mRNA in their baseline CTC samples. In these patients, the median AR-V7/AR-FL ratio was 22.9% (range, 2.6-69.2%) (FIG. 14).

The prevalence of AR-V7 was influenced by use of prior enzalutamide/abiraterone: in men who had not previously received enzalutamide or abiraterone, AR-V7 was detected in 50% of cases (7/14); and in men who had received both enzalutamide and abiraterone, AR-V7 was detected in 53% of cases (8/15).

Table 11 showed baseline characteristics for the taxane-treated population as a whole, and separated by AR-V7 status. AR-V7-positive men were more likely to have younger age, Gleason score ≥8, prior abiraterone/enzalutamide treatment, ≥6 bone metastases, higher PSA levels, higher alkaline phosphatase levels, and higher AR-FL levels (although most of these differences were not statistically significant).

TABLE 11

Baseline characteristics of the 37 taxane-treated patients.

| Baseline Characteristic | All Patients (N = 37) | AR-V7 Negative (N = 20) | AR-V7 Positive (N = 17) | P-value* |
|---|---|---|---|---|
| Age (years) | | | | |
| median (range) | 67 (46-82) | 68 (46-82) | 64 (50-77) | 0.106 |
| Race, N (%) | | | | |
| white | 32 (86.5%) | 16 (80.0%) | 16 (94.1%) | |
| non-white | 5 (13.5%) | 4 (20.0%) | 1 (5.9%) | 0.348 |
| Time since diagnosis (years) | | | | |
| median (range) | 5 (1-12) | 5 (1-12) | 4 (1-11) | 0.602 |
| Tumor stage at diagnosis, N (%) | | | | |
| T1/T2 | 14 (37.8%) | 7 (35.0%) | 7 (41.2%) | |
| T3/T4 | 23 (62.2%) | 13 (65.0%) | 10 (58.8%) | 0.745 |
| Gleason sum at diagnosis, N (%) | | | | |
| ≤7 | 6 (17.1%) | 4 (22.2%) | 2 (11.8%) | |
| ≥8 | 29 (82.9%) | 14 (77.8%) | 15 (88.2%) | 0.658 |
| Type of local treatment, N (%) | | | | |
| surgery | 14 (37.8%) | 7 (35.0%) | 7 (41.2%) | |
| radiation | 9 (24.4%) | 5 (25.0%) | 4 (23.5%) | |
| none | 14 (37.8%) | 8 (40.0%) | 6 (35.3%) | 0.999 |
| Current taxane therapy, N (%) | | | | |
| docetaxel | 30 (81.1%) | 15 (75.0%) | 15 (88.2%) | |
| cabazitaxel | 7 (18.9%) | 5 (25.0%) | 2 (11.8%) | 0.416 |
| Number of prior hormonal therapies | | | | |
| median (range) | 4 (2-7) | 4 (2-7) | 4 (2-6) | 0.924 |
| Prior use of abiraterone, N (%) | | | | |
| yes | 29 (78.4%) | 14 (70.0%) | 15 (88.2%) | |
| no | 8 (21.6%) | 6 (30.0%) | 2 (11.8%) | 0.246 |
| Prior use of enzalutamide, N (%) | | | | |
| yes | 15 (40.5%) | 7 (35.0%) | 8 (47.1%) | |
| no | 22 (59.5%) | 13 (65.0%) | 9 (52.9%) | 0.516 |
| Prior use of docetaxel, N (%) | | | | |
| yes | 7 (18.9%) | 5 (25.0%) | 2 (11.8%) | |
| no | 30 (81.1%) | 15 (75.0%) | 15 (88.2%) | 0.416 |
| Presence of bone metastases, N (%) | | | | |
| yes | 35 (94.6%) | 18 (90.0%) | 17 (100.0%) | |
| no | 2 (5.4%) | 2 (10.0%) | 0 (0.0%) | 0.489 |
| Number of bone metastases, N (%) | | | | |
| ≤5 | 6 (16.2%) | 5 (25.0%) | 1 (5.9%) | |
| ≥6 | 31 (83.8%) | 15 (75.0%) | 16 (94.1%) | 0.189 |
| Presence of visceral metastases, N (%) | | | | |
| yes | 13 (35.1%) | 7 (35.0%) | 6 (35.3%) | |
| no | 24 (64.9%) | 13 (65.0%) | 11 (64.7%) | 0.999 |
| ECOG performance status, N (%) | | | | |
| 0 | 20 (54.1%) | 8 (40.0%) | 12 (70.6%) | |
| 1 or 2 | 17 (45.9%) | 12 (60.0%) | 5 (29.4%) | 0.099 |
| Baseline PSA (ng/mL) | | | | |
| median (range) | 126 (0.1-2270) | 102 (5-534) | 189 (0.1-2270) | 0.074 |

TABLE 11-continued

Baseline characteristics of the 37 taxane-treated patients.

| Baseline Characteristic | All Patients (N = 37) | AR-V7 Negative (N = 20) | AR-V7 Positive (N = 17) | P-value* |
|---|---|---|---|---|
| Baseline alkaline phosphatase (U/L) | | | | |
| median (range) | 161 (53-1243) | 111 (53-930) | 291 (53-1243) | 0.070 |
| Baseline AR-FL level (copy number) | | | | |
| median (range) | 16 (0-4567) | 4 (0-55) | 88 (4-4567) | <0.001 |

*P-values are based on Fisher's Exact test and Wilcoxon Mann-Whitney test for categorical and continuous variables, respectively.

Table 12 compared baseline characteristics of the 37 taxane-treated patients and the 62 enzalutamide/abiraterone-treated patients from the prior study.[11] In this updated analysis, median follow-up among all enzalutamide/abiraterone-treated patients was 13.0 (range, 1.4-19.8) months. 29.0% of these men (18/62) had detectable AR-V7 at baseline. Compared to taxane-treated patients, enzalutamide/abiraterone-treated men were more likely to have Gleason scores ≤7, less prior hormonal therapies, ≤5 bone metastases, ECOG performance status of 0, lower PSA levels, lower alkaline phosphatase levels, and lower AR-FL levels (although not all of these differences were statistically significant).

TABLE 12

Comparison of baseline characteristics of the 37 taxane-treated patients and the 62 enzalutamide/abiraterone-treated patients.

| Baseline Characteristic | Taxane-Treated Patients (N = 37) | Enzalutamide/abiraterone-Treated Patients (N = 62) | P-value* |
|---|---|---|---|
| Age (years) | | | |
| median (range) | 67 (46-82) | 69 (48-84) | 0.321 |
| Race, N (%) | | | |
| white | 32 (86.5%) | 51 (82.3%) | |
| non-white | 5 (13.5%) | 11 (17.7%) | 0.779 |
| Time since diagnosis (years) | | | |
| median (range) | 5 (1-12) | 5 (1-21) | 0.593 |
| Tumor stage at diagnosis, N (%) | | | |
| T1/T2 | 14 (37.8%) | 29 (46.8%) | |
| T3/T4 | 23 (62.2%) | 33 (53.2%) | 0.410 |
| Gleason sum at diagnosis, N (%) | | | |
| ≤7 | 6 (17.1%) | 20 (33.3%) | |
| ≥8 | 29 (82.9%) | 40 (66.7%) | 0.101 |
| Type of local treatment, N (%) | | | |
| surgery | 14 (37.8%) | 27 (43.5%) | |
| radiation | 9 (24.4%) | 17 (27.4%) | |
| none | 14 (37.8%) | 18 (29.1%) | 0.675 |
| Number of prior hormonal therapies | | | |
| median (range) | 4 (2-7) | 3 (2-6) | 0.001 |
| Prior enzalutamide/abiraterone, N (%) | | | |
| yes | 29 (78.4%) | 24 (38.7%) | |
| no | 8 (21.6%) | 38 (61.3%) | <0.001 |
| Prior use of docetaxel, N (%) | 7 (18.9%) | 25 (40.3%) | 0.045 |
| yes | 30 (81.1%) | 37 (59.7%) | |
| no | | | |
| Presence of bone metastases, N (%) | | | |
| yes | 35 (94.6%) | 52 (83.9%) | |
| no | 2 (5.4%) | 10 (16.1%) | 0.201 |
| Number of bone metastases, N (%) | | | |
| ≤5 | 6 (16.2%) | 37 (59.7%) | |
| ≥6 | 31 (83.8%) | 25 (40.3%) | <0.001 |
| Presence of visceral metastases, N (%) | | | |
| yes | 13 (35.1%) | 18 (29.0%) | |
| no | 24 (64.9%) | 44 (71.0%) | 0.655 |

TABLE 12-continued

Comparison of baseline characteristics of the 37 taxane-treated patients and the 62 enzalutamide/abiraterone-treated patients.

| Baseline Characteristic | Taxane-Treated Patients (N = 37) | Enzalutamide/abiraterone-Treated Patients (N = 62) | P-value* |
|---|---|---|---|
| ECOG performance status, N (%) | | | |
| 0 | 20 (54.1%) | 47 (75.8%) | |
| 1 or 2 | 17 (45.9%) | 15 (24.2%) | 0.029 |
| Baseline PSA (ng/mL) | | | |
| median (range) | 126 (0.1-2270) | 42 (2.2-3204) | 0.008 |
| Baseline alkaline phosphatase (U/L) | | | |
| median (range) | 161 (53-1243) | 111 (58-1348) | 0.038 |
| Baseline AR-FL level (copy number) | | | |
| median (range) | 16 (0-4567) | 7 (0-734) | 0.051 |

*P-values are based on Fisher's Exact test and Wilcoxon Mann-Whitney test for categorical and continuous variables, respectively Clinical Outcomes in Taxane-Treated Patients According to AR-V7 Status PSA Responses.

The overall proportion of patients who achieved a PSA response on taxane treatment was 54% (20/37 men; 95% CI, 37-71%), and there was no significant difference according to AR-V7 status. PSA-response rates were 41% (7/17 men; 95% CI, 18-67%) in AR-V7-positive patients and 65% (13/20 men; 95% CI, 41-85%) in AR-V7-negative patients, a non-significant difference of 24% (P=0.194, 95% CI for the difference, −13-60/0). Best PSA responses according to AR-V7 status are depicted in FIG. 15. In multivariable logistic regression modeling, AR-V7 status remained non-predictive for PSA response (OR 0.39, 95% CI 0.06-2.32, P=0.307) after adjusting for AR-FL expression and previous use of enzalutamide/abiraterone.

PSA-PFS.

Figure 16A:
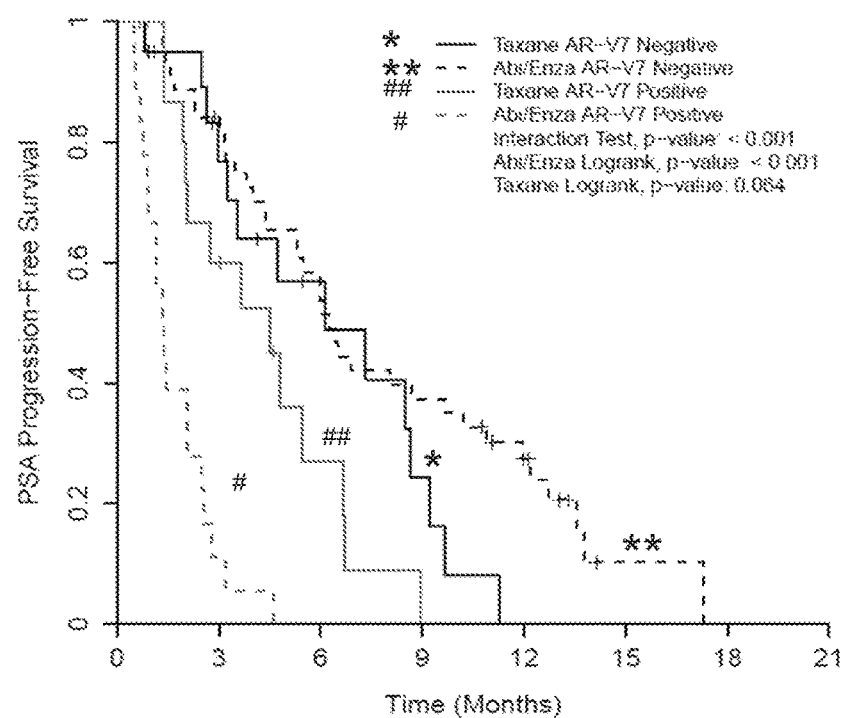

PSA-progression-free-survival (PSA-PFS) did not differ significantly according to AR-V7 status. Median PSA-PFS was 4.5 months in AR-V7-positive men and 6.2 months in AR-V7-negative men (HR 2.1, 95% CI 0.9-4.9, P=0.064) (FIG. 16A, solid lines). In a multivariable Cox model adjusting for AR-FL expression and prior enzalutamide/abiraterone use, AR-V7 status remained non-significant in its ability to predict PSA-PFS (HR 1.7, 95% CI 0.6-5.0, P=0.324); AR-FL levels (HR 1.0, 95% CI 0.9-1.2) and previous enzalutamide/abiraterone use (HR 1.4, 95% CI 0.4-4.2) were also non-predictive of PSA-PFS in this multivariable analysis.

PFS.

Figure 16B:
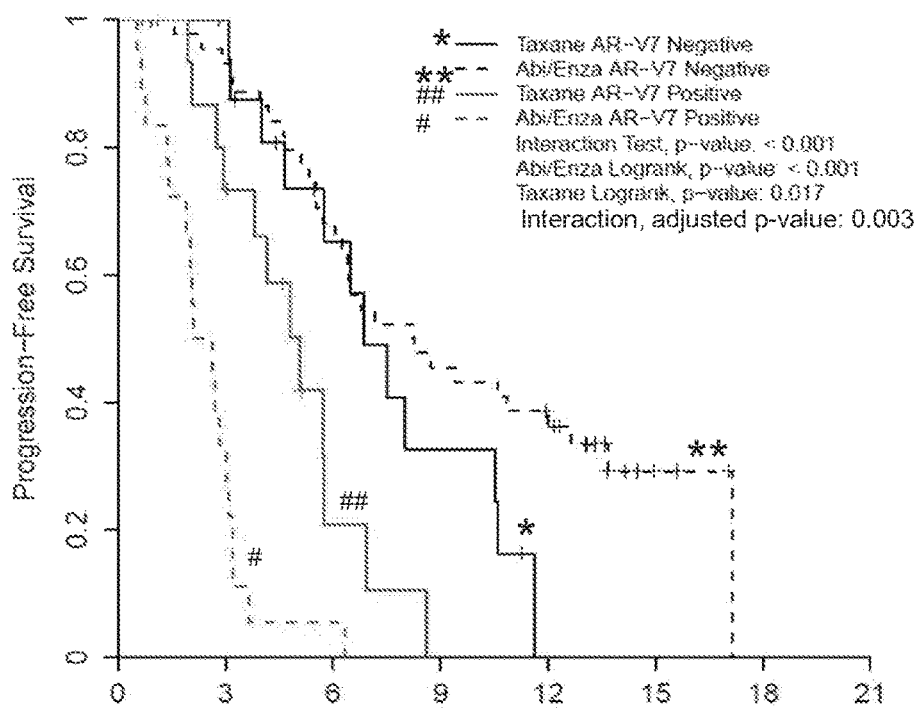

Clinical/radiographic-progression-free survival (PFS) also did not differ significantly depending on AR-V7 status. Median PFS was 5.1 months in AR-V7-positive men and 6.9 months in AR-V7-negative men (HR 2.8, 95% CI 1.2-6.9, P=0.017) (FIG. 16B, solid lines). Although this difference appeared significant, in a multivariable Cox model adjusting for AR-FL expression and prior enzalutamide/abiraterone use, AR-V7 status lost its ability to predict PFS (HR 2.7, 95% CI 0.8-8.8, P=0.110); AR-FL levels (HR 1.0, 95% CI 0.9-1.1) and previous enzalutamide/abiraterone use (HR 1.7, 95% CI 0.5-6.2) were also non-predictive of PFS.

OS (Exploratory).

Figure 16C:
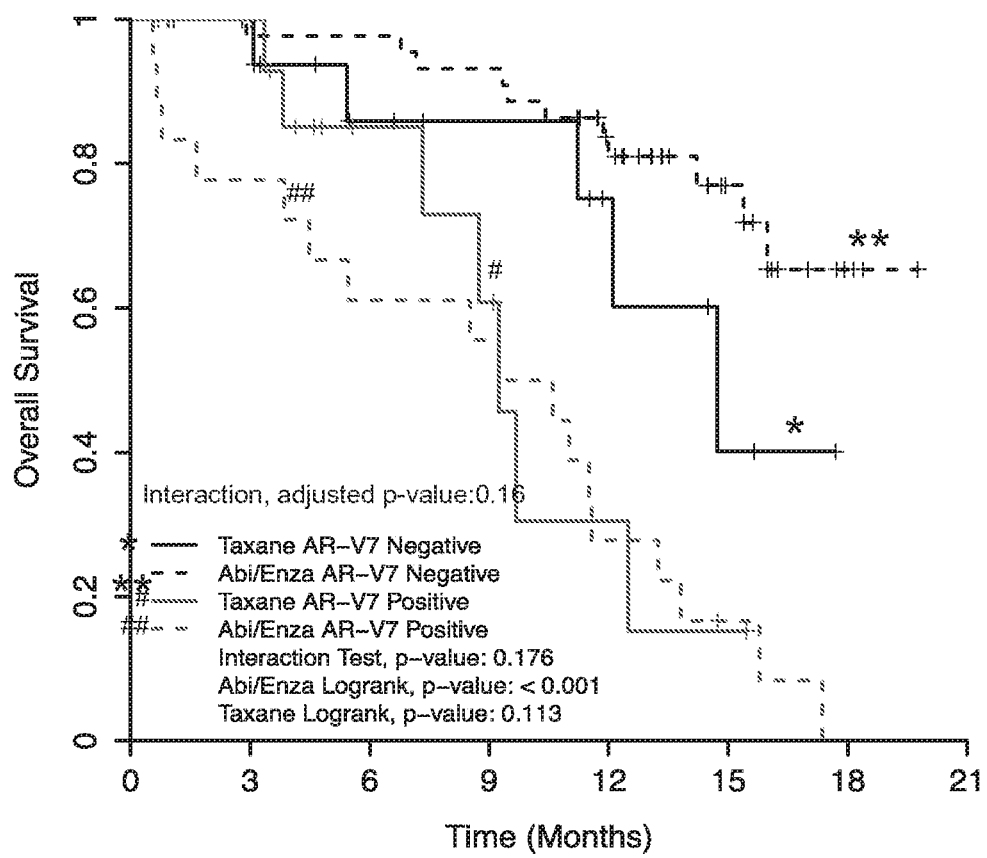

Overall-survival (OS) also did not differ significantly according to AR-V7 status. Median OS was 9.2 months in AR-V7-positive men and 14.7 months in AR-V7-negative men (HR 2.5, 95% CI 0.8-8.1, P=0.113) (FIG. 16C, solid lines). In a multivariable Cox model adjusting for AR-FL expression, AR-V7 status remained non-significant in its ability to predict OS (HR 0.7, 95% CI 0.1-3.8, P=0.657); AR-FL levels were also non-predictive of OS (HR 1.3, 95% CI 0.9-1.8).

Differential Effect of AR-V7 in Men Treated with Taxanes Versus AR-Directed Therapies PSA Responses.

A significant interaction between AR-V7 status and treatment type was observed in the unadjusted linear model (P=0.002). In an adjusted model also accounting for AR-FL levels, prior chemotherapy use, and prior enzalutamide/abiraterone use, the interaction remained significant (P=0.006).

PSA-PFS.

A significant interaction between AR-V7 status and treatment type was observed in the unadjusted Cox model (P<0.001) (FIG. 16A). In an adjusted model also accounting for AR-FL levels, prior chemotherapy, and prior enzalutamide/abiraterone, the interaction remained significant (P=0.001).

PFS.

A significant interaction between AR-V7 status and treatment type was observed in the unadjusted Cox model (P<0.001) (FIG. 16B). In the adjusted model, the interaction remained significant (P=0.003).

OS (Exploratory).

A significant interaction between AR-V7 status and treatment type was not observed either in the unadjusted Cox model (P=0.176) (FIG. 16C), or the adjusted model (P=0.157).

Clinical Outcomes with Taxanes Versus AR-Directed Therapies According to AR-V7 Status AR-V7-Positive Patients.

Treatment with taxanes appeared superior to AR-directed therapy in AR-V7-positive men. PSA responses were 41% (7/17) in taxane-treated patients and 0% (0/18) in enzalutamide/abiraterone-treated patients (P<0.001). In a multivariable linear model adjusting for AR-FL level, prior chemotherapy, and prior enzalutamide/abiraterone, treatment with taxanes remained superior to enzalutamide/abiraterone (P<0.001). Moreover, median PSA-PFS was longer in taxane-treated men compared to enzalutamide/abiraterone-treated men (HR 0.22, 95% CI 0.09-0.53, P<0.001) (FIG. 16A, #/##). In a multivariable Cox model adjusting for AR-FL level and prior enzalutamide/abiraterone, taxane therapy remained superior to AR-directed therapy (HR 0.19, 95% CI 0.07-0.52, P=0.001). Similarly, median PFS was longer in taxane-treated compared to enzalutamide/abiraterone-treated men (HR 0.26, 95% CI 0.11-0.59, P=0.001) (FIG. 16B, #/##). In a multivariable Cox model adjusting for AR-FL level and prior enzalutamide/abiraterone, taxane therapy remained superior (HR 0.21, 95% CI 0.07-0.59, P=0.003). Finally, median OS (exploratory) was numerically superior in taxane-treated compared to enzalutamide/abiraterone-treated patients (HR 0.83, 95% CI 0.34-2.00, P=0.764) (FIG. 16C, #/##). In a multivariable Cox model adjusting for AR-FL level and prior enzalutamide/abiraterone, there was a trend towards superior survival with taxane therapy (HR 0.28, 95% CI 0.07-1.00, P=0.059).

AR-V7-Negative Patients.

There were no significant differences between taxane treatment and AR-directed therapy with respect to any clinical outcomes in AR-V7-negative men. PSA responses were 65% (13/20) in taxane-treated patients and 64% (28/44) in enzalutamide/abiraterone-treated patients (P=0.604); this difference remained non-significant after adjusting for AR-FL level, prior chemotherapy, and prior enzalutamide/abiraterone in a multivariable linear model (P=0.361). Median PSA-PFS was not significantly different in taxane-treated patients compared to enzalutamide/abiraterone-treated patients (HR 1.61, 95% CI 0.84-3.06, P=0.149) (FIG. 16A, */**), even after adjusting for AR-FL level and prior enzalutamide/abiraterone in the multivariable Cox model (HR 1.09, 95% CI 0.51-2.31, P=0.828). Similarly, median PFS was not significantly different in taxane-treated compared to enzalutamide/abiraterone-treated patients (HR 1.68, 95% CI 0.84-3.33, P=0.142) (FIG. 16B, */**), even after adjusting for AR-FL and prior enzalutamide/abiraterone in multivariable Cox analysis (HR 1.02, 95% CI 0.46-2.25, P=0.959). Finally, median OS (exploratory) was not significantly different between the two treatment groups, either in the univariate (HR 2.26, 95% CI 0.78-6.62, P=0.134) (FIG. 16C, */**) or the multivariable (HR 1.55, 95% CI 0.49-4.95, P=0.459) analyses.

AR-V7 Conversions at Taxane Progression

Twenty-one taxane-treated patients had paired CTC samples collected at baseline and at the time of progression that were evaluable for AR-V7. Among men with initially undetectable AR-V7 (n=9), 1 patient (11%) subsequently converted to AR-V7-positive during the course of taxane treatment while 8 patients (89%) remained AR-V7-negative at progression. Conversely, among men with detectable AR-V7 at baseline (n=12), 7 patients (58%) converted to AR-V7-negative during taxane therapy while 5 patients (42%) remained AR-V7-positive at progression. The clinical significance of these conversions in AR-V7 status is currently unknown.

DISCUSSION

While there are multiple available therapies for men with metastatic CRPC, there are currently no molecular biomarkers to help guide optimal treatment choices in these patients. We have previously shown that detection of AR-V7 is associated with primary resistance to abiraterone and enzalutamide, as manifested by inferior PSA responses, shorter PFS, and shorter OS.[11] Here we show that men with detectable AR-V7 retain sensitivity to taxane chemotherapies, that the impact of AR-V7 is more significant in the context of AR-directed therapies than with chemotherapies, and that taxanes may have superior efficacy to enzalutamide/abiraterone in AR-V7-positive men (but not in AR-V7-negative men). The current study represents the first prospective analysis of AR-V7 in patients receiving taxane chemotherapy, and the summation of our data suggests that AR-V7 may be a treatment-selection marker in CRPC.

Although the principle mechanism-of-action of taxane agents is the disruption of microtubules inducing mitotic arrest, it is increasingly understood that taxanes may also mediate their antitumor effects in CRPC by disrupting cytoplasmic-to-nuclear trafficking of AR along the microtubule network,[17-20] while other mechanisms have also been postulated.[25,26] Therefore, some degree of cross-resistance has been suggested between AR-targeting therapies and taxanes chemotherapies, although this cross-resistance may be less significant with cabazitaxel than with docetaxel.[27] Recently, work on a particular mouse model of CRPC has also suggested that certain AR-Vs may be associated with sensitivity to taxanes while others may mediate taxane resistance.[22] To this end, AR-V7 was shown to result in taxane resistance in at least one preclinical model, due to deletion of the AR hinge region that is thought to be necessary for microtubule binding.[22] However, the clinical data do not recapitulate the observations from this mouse model. In fact, herein was shown that in AR-V7-positive patients, PSA response rates are 41% and median PFS is 5.1 months. While clinical outcomes to taxanes may appear inferior in AR-V7-positive compared to AR-V7-negative men, these differences were not statistically significant after multivariable adjustments. More importantly, we demonstrate that AR-V7 detection is not associated with primary resistance to taxane agents (as observed with abiraterone and enzalutamide[11]).

An observation from this example was the suggestion that taxane therapy may be more efficacious than AR-directed therapy for men with AR-V7-positive CRPC. Conversely, clinical outcomes did not appear to differ significantly based on the type of therapy used among AR-V7-negative patients. If these results are confirmed by additional prospective biomarker-stratified clinical trials, this observation might suggest that AR-V7-positive men may fare better with taxane chemotherapies rather than AR-targeting therapies, while in AR-V7-negative men both treatment approaches might be reasonable. There may be limitations. Due to the small sample size, comprehensive multivariable analysis was not performed to determine the independent contribution of AR-V7 status on prognosis, and subpopulations were not defined in which the utility of the biomarker may be greatest. AR-V7 may be a marker of more advanced disease or higher disease burden. Second, the comparison of clinical outcomes between taxane-treated and enzalutamide/abiraterone-treated patients may be effected by the fact that treatment selection was not randomly assigned, and baseline patient characteristics (including numbers and types of prior therapies received) were different in the two cohorts. Confirmation of these findings can be determined in larger biomarker-driven studies randomizing patients to taxane chemotherapy versus AR-directed therapy. This will be pursued in the PRIMCAB study (NCT02379390), a multi-center randomized phase-2 trial of abiraterone/enzalutamide versus cabazitaxel in men with primary resistance to prior enzalutamide/abiraterone.

A finding was the fact that certain patients with detectable AR-V7 at baseline converted to AR-V7-negative during the course of taxane therapy. AR-V7 in enzalutamide/abiraterone-treated patients, all men with detectable AR-V7 at baseline remained AR-V7-positive throughout treatment with abiraterone and enzalutamide.[11] Biologically, a conversion from AR-V7-positive to negative might imply decreased selection pressure on the AR axis exerted by taxanes, allowing a resumption of canonical AR signaling and a lack of requirement for aberrant AR-V-mediated signaling. An alternative hypothesis was that effective taxane therapy may have decreased the burden of circulating tumor cells, thereby making it more difficult to detect AR-V7 present in low abundance. The clinical significance of these AR-V7 conversions is the subject of ongoing investigations.

Findings here suggest that detection of AR-V7 in CTCs from patients with CRPC was not associated with primary resistance to taxane chemotherapy, and that AR-V7-positive patients may respond better to taxanes than AR-targeting drugs. AR-V7 status provides the first treatment-selection biomarker for CRPC.

What is claimed is:

1. A method comprising:
   determining the expression level of an androgen receptor variant 7 (AR-V7) in a sample from a prostate cancer patient by amplifying both full-length androgen receptor ("AR-FL") and AR-V7 transcripts, wherein the sample is enriched for circulating tumor cells.

2. The method of claim 1, wherein the determining involves (a) amplification with a polymerase chain reaction ("PCR"); (b) multiplex PCR; or (c) quantitative reverse-transcription polymerase chain reaction ("qRT-PCR").

3. The method of claim 2, wherein the PCR utilizes primers whose sequences are or comprise: SEQ ID NOS: 1-2 (AR-V7 (forward) 5'-CCATCTTGTCGTCTTCG-GAAATGTTA-3' SEQ ID NO: 1; AR-V7 (reverse) 5'-TT-GAATGAGGCAAGTCAGC-CTTTCT-3' SEQ ID NO:2) and/or SEQ ID NOS: 3-4 (AR-FL (forward) 5'-CAGCCT-ATTGCGAGAGAGCTG-3' SEQ ID NO:3; AR-FL (reverse) 5'-GAAAGGATCTTGGGCACTTGC-3' SEQ ID NO:4).

4. The method of claim 1, wherein the patient is a castration-resistant prostate cancer patient ("CRPC").

5. The method of claim 4, wherein the patient is treated with an AR signaling inhibitor or a CYP17 inhibitor.

6. The method of claim 1, further comprising a step of: repeating the determination on multiple samples, each of which was obtained at a different time point following diagnosis of prostate cancer.

7. The method of claim 6, wherein at least one time point is a baseline time point, at a moment of clinical or biochemical response, or at a moment of clinical or radiographic progression.

8. The method of claim 7, wherein the clinical or biochemical response is or comprises measurement of prostate specific antigen.

9. The method of claim 1, further comprising a step of: administering an alternative therapy to therapy with abiraterone or enzalutamide when AR-V7 is detected.

10. The method of claim 9, wherein the alternative therapy comprises administration of an antineoplastic agent selected from the group consisting of Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole;

Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer; and combinations thereof.

11. The method of claim 9, wherein the alternative therapy comprises administration of an agent selected from the group consisting of antineoplastic agents, alkylating agents, antimetabolites, anthracyclines, plant alkaloids, topoisomerase inhibitors, monoclonal antibodies, terpenoids, vinca alkaloids, taxanes, antitumor antibiotics, hormonal therapy, and combinations thereof.

12. The method of claim 1, wherein the step of determining comprises utilizing a hybridization assay.

13. The method of claim 12, wherein the hybridization assay is in situ hybridization of fresh or autopsy tumor samples.

14. The method of claim 1, wherein the step of determining comprises PCR to determine the amount of AR-V7 compared to the amount of AR-FL.

15. The method of claim 1, wherein the prostate cancer patient is receiving a course of treatment and the step of determining is repeated at a plurality of time points over the course of treatment.

16. The method of claim 15, wherein the AR-V7 is initially undetectably in a first determining step and is greater than or equal to 1 in at least one subsequent determining step performed at a later time point over the course of treatment.

17. The method of claim 15, wherein each determining step comprises determining the ratio of absolute copy number of AR-V7 to AR-FL.

18. The method of claim 9, wherein the alternative therapy inhibits both AR-FL and AR-V7.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
cagcctattg cgagagagct g                                      21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
gaaaggatct tgggcacttg c                                      21

<210> SEQ ID NO 3
<211> LENGTH: 26
<212> TYPE: DNA
<213> ORGANISM: Artificial Sequence
<220> FEATURE:
<223> OTHER INFORMATION: Synthetic primer

<400> SEQUENCE: 3
ccatcttgtc gtcttcggaa atgtta                                 26

<210> SEQ ID NO 4
<211> LENGTH: 25
<212> TYPE: DNA
<213> ORGANISM: Artificial Sequence
<220> FEATURE:
<223> OTHER INFORMATION: Synthetic primer

<400> SEQUENCE: 4
ttgaatgagg caagtcagcc tttct                                  25
```